United States Patent
Xie et al.

(10) Patent No.: US 11,505,534 B2
(45) Date of Patent: Nov. 22, 2022

(54) HIGHLY DIASTEREOSELECTIVE CONSTRUCTION OF THE 4,5-SPIROCYCLE VIA PALLADIUM-CATALYZED INTRAMOLECULAR ALKENYLATION

(71) Applicant: The University of Chicago, Chicago, IL (US)

(72) Inventors: Jiaxin Xie, Chicago, IL (US); Guangbin Dong, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 16/614,155

(22) PCT Filed: May 16, 2018

(86) PCT No.: PCT/US2018/032964
§ 371 (c)(1),
(2) Date: Nov. 15, 2019

(87) PCT Pub. No.: WO2018/213442
PCT Pub. Date: Nov. 22, 2018

(65) Prior Publication Data
US 2020/0079749 A1    Mar. 12, 2020

Related U.S. Application Data

(60) Provisional application No. 62/506,882, filed on May 16, 2017.

(51) Int. Cl.
*C07D 307/94* (2006.01)
*B01J 31/22* (2006.01)
*C07D 307/83* (2006.01)

(52) U.S. Cl.
CPC ........ *C07D 307/94* (2013.01); *B01J 31/2239* (2013.01); *C07D 307/83* (2013.01)

(58) Field of Classification Search
CPC .. C07D 307/94; C07D 307/83; B01J 31/2239; A61P 37/00
(Continued)

(56) References Cited

U.S. PATENT DOCUMENTS 4,847,414 A     7/1989  Glamkowski et al.
2010/0061982 A1 3/2010  Ayral-Kaloustian et al.
(Continued)

FOREIGN PATENT DOCUMENTS

WO    WO 2015/149068 A1    10/2015

OTHER PUBLICATIONS

International Search Report corresponding to International Patent Application No. PCT/US2018032964 dated Jul. 25, 2018.
(Continued)

*Primary Examiner* — Taylor V Oh
(74) *Attorney, Agent, or Firm* — Jenkins, Wilson, Taylor & Hunt, P.A.

(57) ABSTRACT

A diastereoselective method of preparing benzofuran-based 4,5-spirocycles via metal catalyzed alkenylation is described. The method can be used to provide compounds containing the benzofuranone-4,5-spirocyclic motif of the phainanoids, a class a natural products having immunosuppressive activity. Synthetic analogs of phainanoids, e.g., compounds that mimic the structure of the "western" part of the structure of the phainanoids and that contain the benzofuranone-4,5-spirocycle are described, as well as their synthetic intermediates, and their methods of synthesis.

30 Claims, 5 Drawing Sheets

X-ray for DNP-hydrazone of 7 (16)

(58) Field of Classification Search
USPC .......................................................... 549/330
See application file for complete search history.

(56) References Cited

U.S. PATENT DOCUMENTS

| 2014/0080823 A1 | 3/2014 | Varasi et al. |
| 2014/0288091 A1 | 9/2014 | Minidis et al. |
| 2016/0168163 A1 | 6/2016 | Forsman et al. |
| 2016/0272600 A1 | 9/2016 | Cacatian et al. |

OTHER PUBLICATIONS

Written Opinion of the International Searching Authority corresponding to International Patent Application No. PCT/US2018032964 dated Jul. 25, 2018.

International Preliminary Report on Patentability corresponding to International Patent Application No. PCT/US2018032964 dated Nov. 19, 2019.

Xie et al., "Synthetic Study of Phainanoids. Highly Diastereoselective Construction of the 4,5-Spirocycle via Palladium-Catalyzed Intramolecular Alkenylation," Organic Letters, vol. 19, Iss. 11 pp. 3017-3020 (2017).

Steroid Total Synthesis: New Transition Metal-Catalyzed Methods for Closure of the Steroid B-Ring, Feb. 8, 2015, Modern Steroid Science, Blog Archive Feb. 2015, pp. 1-7.

On the Biosynthesis of the Phainanoids, A New Class of Immunosuppressive Steroid, Feb. 17, 2015, Modern Steroid Science, Blog Archive Feb. 2015, pp. 1-7.

Iwasaki et al., "Simple, Chemoselective Hydrogenation with Thermodynamic Stereocontrol," J. Am. Chem. Soc., vol. 136, pp. 1300-1303 (2014).

Hayashi et al., "Synthesis of a-and/or y-benzoyloxy-a, β-enones from α-halo-α,β-enones," Tett. Lett. vol. 46 pp. 681-685 (2005).

Marenich et al., "Universal Solvation Model Based on Solute Electron Density and on a Continuum Model of the Solvent Defined by the Bulk Dielectric Constant and Atomic Surface Tensions," J. Phys. Chem. B, vol. 113 pp. 6378-6396 (2009).

Zhao and Truhlar, "The M06 suite of density functionals for main group thermochemistry, thermochemical kinetics, noncovalent interactions, excited states, and transition elements: two new functionals and systematic testing of four M06-class functionals and 12 other functionals," Theor. Chem. Acc., 120, pp. 215-241 (2008).

Ankner et al., "Palladium- and Nickel-Catalyzed Alkenylation of Enolates," Chem. Eur. J., vol. 19, pp. 1858-1871 (2013).

Chen et al., "Cu(I)-Catalyzed Intramolecular C—C Coupling of Activated Methylene Compounds with Vinyl Halides: Efficient Synthesis of Functionalized Alkylidenecyclobutanes," Org. Lett., vol. 10, No. 22, pp. 5285-5288 (2008).

Fan et al., "Phainanoids A-F, A New Class of Potent Immunosuppressive Triterpenoids with an Unprecedented Carbon Skeleton from Phyllanthus hainanensis," J. Am. Chem. Soc., vol. 137, pp. 138-141 (2015).

Grigalunas et al., "Palladium-Catalyzed Alkenylation of Ketone Enolates under Mild Conditions," Org. Lett., vol. 16, pp. 3970-3973 (2014).

Grigalunas et al., "Ni-Catalyzed Alkenylation of Ketone Enolates under Mild Conditions: Catalyst Identification and Optimization," J. Am. Chem. Soc., vol. 137, No. 22, 7019-7022 (2015).

Keinan et al. "Highly Chemoselective Palladium-Catalyzed Conjugate Reduction of α,β-Unsaturated Carbonyl Compounds with Silicon Hydrides and Zinc Chloride Cocatalyst," J. Am. Chem. Soc., vol. 108, No. 23, pp. 7314-7325 (1986).

Kwon et al., "A Series of Novel Terpyridine-Skeleton Molecule Derivants Inhibit Tumor Growth and Metastasis by Targeting Topoisomerases," J. Med. Chem., vol. 58, pp. 1100-1122 (2015).

Lipshutz et al., "1,4-Reductions of α,β-Unsaturated Ketones and Aldehydes via in situ Generated Hydridocuprates," Synlett, pp. 64-66 (1989).

Magnus et al., "Conjugate reduction of α,β-unsaturated ketones using an MnIII catalyst, phenylsilane and isopropyl alcohol," Tett. Lett., vol. 41, pp. 9731-9733 (2000).

Moser et al., "CuH-Catalyzed Enantioselective 1,2-Reductions of a,β-Unsaturated Ketones," J. Am. Chem. Soc., vol. 132, No. 23, pp. 7852-7853 (2010).

Rajendar et al. "A Systematic Study of Functionalized Oxiranes as Initiating Groups for Cationic Polycyclization Reactions," J. Am. Chem. Soc., vol. 137, No. 17, pp. 5837-5844 (2015).

Shneider et al., "Oxidative Umpolung α-Alkylation of Ketones," Org. Lett., vol. 17, pp. 282-285 (2015).

Still et al., "Direct Synthesis of Z-Unsaturated Esters. A Useful Modification of the Horner-Emmons Olefination," Tetrahedron Lett., vol. 24, No. 41, pp. 4405-4408 (1983).

Zhao et al. "Density Functionals with Broad Applicability in Chemistry," Acc. Chem. Res., vol. 41, No. 2, pp. 157-167 (2008a).

Zhao et al., "Indium tribromide-promoted arene-terminated epoxy olefin cyclization," Chemical Communications, pp. 1353-1355 (2008c).

HIGHLY DIASTEREOSELECTIVE CONSTRUCTION OF THE 4,5-SPIROCYCLE VIA PALLADIUM-CATALYZED INTRAMOLECULAR ALKENYLATION

RELATED APPLICATIONS

This application is a 35 U.S.C. Section 371 national phase application of PCT International Application Serial No. PCT/US2018/032964, filed May 16, 2018, which claims the benefit of U.S. Provisional Patent Application Ser. No. 62/506,882, filed May 16, 2017; the disclosure of which is incorporated herein by reference in its entirety.

TECHNICAL FIELD

The presently disclosed subject matter relates to the synthesis of compounds comprising a benzofuranone 4,5-spirocycle using a metal catalyzed intramolecular alkenylation. Such compounds include novel analogs of the natural product immunosuppressive phainanoid class of compounds. The presently disclosed subject matter further relates to the phainanoid analogs themselves and to their synthetic intermediates.

ABBREVIATIONS

° C.=degrees Celsius
%=percentage
μl=microliter
μM=micromolar
DCM=dichloromethane
DFT=density functional theory
DMF=dimethylformamide
g=gram
h=hour
HMDS=hexamethyldisilamide
$IC_{50}$=fifty percent inhibitory concentration
K=potassium
kg=kilogram
Li=lithium
M=molar
Me=methyl
mg=milligram
min=minute
mL=milliliter
mM=millimolar
mmol=millimole
mol=mole
Ni=nickel
nm=nanometer
nM=nanomolar
nmol=nanomoles
NMR=nuclear magnetic resonance
OAc=acetate
O$^t$Bu=tert-butoxide
OTf=triflate
Pd=palladium
Pd(OAc)$_2$=palladium acetate
Ph=phenyl
PhMe=toluene
Pt=platinum
QPhos=1,2,3,4,5-pentaphenyl-1'-(di-tert-butylphosphino)ferrocene
rt=room temperature
$^t$Bu=tert-butyl
Tf=trifyl
THF=tetrahydrofuran

BACKGROUND

The development of efficacious immunosuppressive agents, for use, for example, during organ transplant or in the treatment of autoimmune and/or inflammatory diseases, is challenging. The use of current immunosuppressive agents (e.g., cyclosporin A, FK 506 and rapamycin) is frequently complicated by adverse events, such as organ toxicities and increased risk of infection and/or cancer, limiting their clinical utility.

Phainanoids, recently isolated from *Phyllanthus hainanensis*, a shrub native to Hainan Island, are a class of novel triterpenoids that exhibit potent immunosuppressive activities. See Fan et al., J. Am. Chem. Soc., 2015, 137, 138. For example, they inhibit proliferation of T and B lymphocytes in vitro with $IC_{50}$ values as low as 2.04 and 1.60 nM respectively.

From a structural perspective, phainanoids possess a complex polycyclic skeleton including 10 ring moieties and at least 13 chiral centers. In particular, they all contain a unique benzofuranone-based 4,5-spirocycle with a strained exocyclic olefin. A gross structure-activity relationship analysis further reveals that such a structural motif can be important for the immunosuppressive activities of the phainanoids. See Fan et al., J. Am. Chem. Soc., 2015, 137, 138. However, the amount of phainanoids available in nature is relatively low, i.e., about 5-20 milligrams (mg) per 5 kilograms (kg) of dry plant material. Synthetic studies of phainanoids have not been reported to date.

Accordingly, there is an ongoing need to provide additional immunosuppressive agents and/or method for preparing such agents. For example, there is a need to develop effective methods of synthesizing phainanoids and structurally related compounds.

SUMMARY

In some embodiments, the presently disclosed subject matter provides a method of preparing a phainanoid analog, the method comprising: (a) providing a compound of Formula (I) or Formula (II):

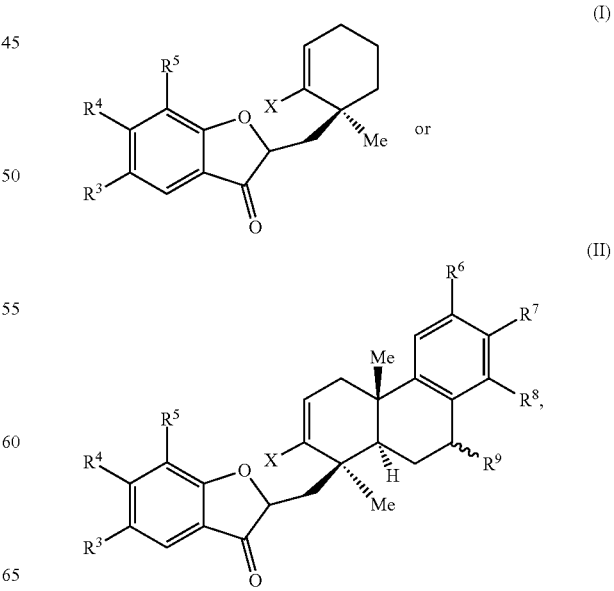

wherein: X is a leaving group, optionally wherein X is selected from the group comprising a halide and —O—S(=O)$_2$—R, wherein R is selected from alkyl, substituted alkyl, aryl, and substituted aryl, optionally wherein R is —CF$_3$, —CH$_3$, —C$_6$H$_4$CH$_3$, or —C$_n$F$_{2n+1}$, where n is an integer between 2 and 12, optionally where n is an integer between 2 and 6; R$^3$, R$^4$, and R$^5$ are each independently selected from the group comprising H, alkyl, substituted alkyl, aryl, substituted aryl, alkoxy, aryloxy, amino, and acetamido; R$^6$, R$^7$, and R$^8$ are each independently selected from the group comprising H, alkyl, substituted alkyl, aryl, substituted aryl, alkoxy, aryloxy, amino, acetamido, and nitro; and R$^9$ is selected from the group comprising H, hydroxyl, and alkoxy; and (b) contacting the compound of Formula (I) or Formula (II) with a metal compound, a ligand precursor, and a non-nucleophilic base to perform an intramolecular ketone alkenylation reaction, optionally wherein the metal compound is a palladium (Pd), nickel (Ni), or platinum (Pt) compound and wherein the ligand precursor is a N-heterocyclic carbene (NHC) precursor or a phosphine; thereby providing a phainanoid analog having a structure of Formula (III) or Formula (IV):

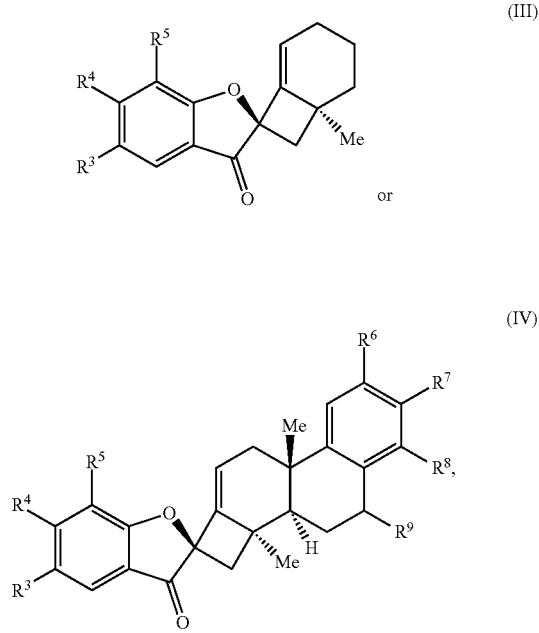

wherein R$^3$-R$^9$ are as defined for the compounds of Formulas (I) and (II). In some embodiments, X is —O—S(=O)$_2$—CF$_3$ (—OTf).

In some embodiments, the metal compound is a Pd compound, optionally wherein the Pd compound is a Pd(II) compound, further optionally wherein the Pd(II) compound is palladium acetate (Pd(OAc)$_2$). In some embodiments, the contacting is performed using between about 5 mole percent (mol %) and about 10 mol % of the metal compound as compared to an amount of the compound of Formula (I) or Formula (II), optionally wherein the contacting is performed using about 5 mol % of the metal compound.

In some embodiments, the ligand precursor is a phosphine, optionally wherein the phosphine is a dialkylarylphosphine, further optionally wherein the dialkylarylphosphine comprises one or both of a ferrocenyl group and a tert-butyl group. In some embodiments, the phosphine is 1,2,3,4,5-pentaphenyl-1'-(di-tert-butylphosphino)ferrocene (QPhos). In some embodiments, the contacting is performed using between about 10 mol % and about 20 mol % of the ligand precursor as compared to the compound of Formula (I) or Formula (II), optionally wherein the contacting is performed using about 10 mol % of the ligand precursor.

In some embodiments, the base is selected from the group comprising lithium hexamethyldisilamide (LiHMDS), potassium hexamethyldisilamide (KHMDS), sodium hexamethyldisilamide (NaHMDS), cesium carbonate (Cs$_2$CO$_3$), lithium tert-butoxide (LiO$^t$Bu), potassium tert-butoxide (KO$^t$Bu), and sodium tert-butoxide (NaO$^t$Bu). In some embodiments, the base is LiO$^t$Bu. In some embodiments, the contacting is performed using about 150 mol % of the base compared to an amount of the compound of Formula (I) or Formula (II).

In some embodiments, the method comprises providing a compound of Formula (I), and the compound of Formula (I) is contacted with a Pd compound, a phosphine, and the non-nucleophilic base in the presence of an ether solvent, optionally wherein the ether solvent is tetrahydrofuran (THF). In some embodiments, the contacting is performed at about room temperature.

In some embodiments, the method comprises providing a compound of Formula (II), and the compound of Formula (II) is contacted with a Pd compound, a phosphine, and the non-nucleophilic base in the presence of an aromatic solvent, optionally wherein the aromatic solvent is toluene. In some embodiments, the contacting is performed at a temperature between about 40 degrees Celsius (° C.) and about 80° C., optionally at about 60° C.

In some embodiments, the contacting is performed for between about 12 hours and about 80 hours, optionally wherein the contacting is performed for between about 24 hours and about 60 hours. In some embodiments, the compound of Formula (III) or Formula (IV) is provided in a yield of about 65% or more and/or with a diastereomeric ratio of about 20:1 or greater. In some embodiments, the compound of Formula (III) or Formula (IV) is selected from the group comprising:

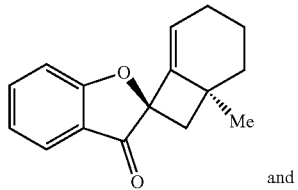

and

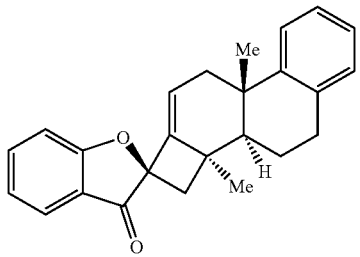

In some embodiments, the presently disclosed subject matter provides a compound of one of Formulas (V) or (VI):

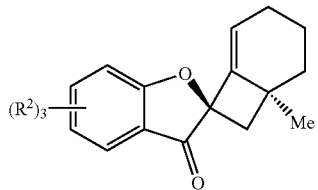
(V)

or

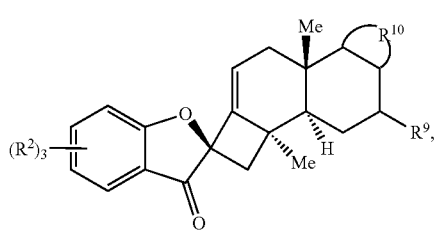
(VI)

wherein: each $R^2$ is independently selected from the group comprising H, alkyl, substituted alkyl, aryl, substituted aryl, alkoxy, aryloxy, amino, and acetamido; $R^9$ is selected from the group comprising H, =O, hydroxyl, protected hydroxyl, and alkoxy; and $R^{10}$ forms a substituted or unsubstituted monocyclic or bicyclic aromatic ring structure, optionally wherein the aromatic ring structure is selected from the group comprising benzene, indole, furan, pyrrole, and benzofuran.

In some embodiments, $R^{10}$ forms a substituted or unsubstituted benzene ring structure, and wherein the compound of Formula (VI) is a compound of Formula (VIa):

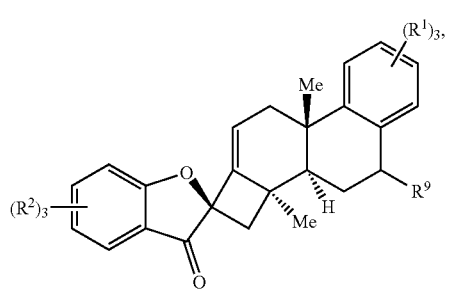
(VIa)

wherein: each $R^1$ is independently selected from the group comprising H, alkyl, substituted alkyl, aryl, substituted aryl, alkoxy, aryloxy, amino, acetamido, and nitro; each $R^2$ is independently selected from the group comprising H, alkyl, substituted alkyl, aryl, substituted aryl, alkoxy, aryloxy, amino, and acetamido; and $R^9$ is selected from the group comprising H, =O, hydroxyl, protected hydroxyl, and alkoxy.

In some embodiments, the compound of Formula (V) or Formula (VI) is a compound of Formula (III) or Formula (IV):

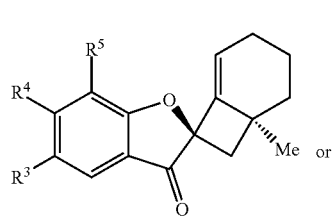
(III)

or

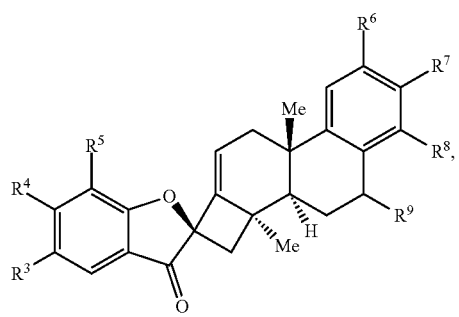
(IV)

wherein: $R^3$, $R^4$, and $R^5$ are each independently selected from the group comprising H, alkyl, substituted alkyl, aryl, substituted aryl, alkoxy, aryloxy, amino, and acetamido; $R^6$, $R^7$, and $R^8$ are each independently selected from the group comprising H, alkyl, substituted alkyl, aryl, substituted aryl, alkoxy, aryloxy, amino, acetamido, and nitro; and $R^9$ is selected from the group comprising H, =O, hydroxyl, protected hydroxyl, and alkoxy.

In some embodiments, $R^9$ is =O and the compound of Formula (IV) is a compound of Formula (IVb):

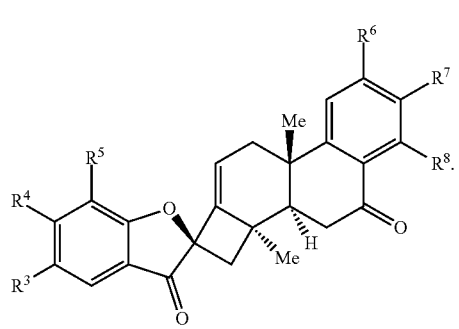
(IVb)

In some embodiments, $R^9$ is selected from H, hydroxyl, protected hydroxyl, and alkoxy, and the compound of Formula (IV) is a compound of Formula (IVa):

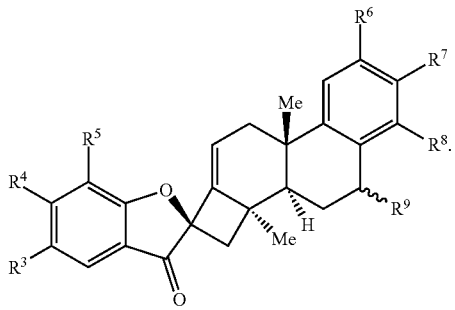

(IVa)

In some embodiments, $R^9$ is H.

In some embodiments, $R^3$, $R^4$, and $R^5$ are each H. In some embodiments, $R^6$, $R^7$, and $R^8$ are each H.

In some embodiments, the compound is selected from the group comprising:

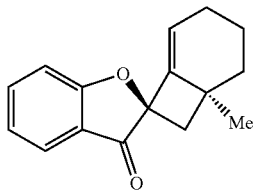

and

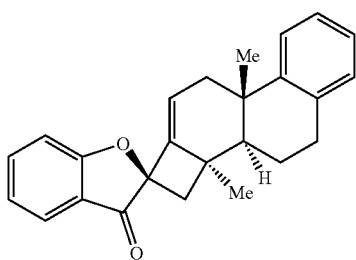

In some embodiments, the presently disclosed subject matter provides a pharmaceutical composition comprising a compound of one of Formulas (III), (IV), (IVa), (IVb), (V), (VI), or (VIa).

In some embodiments, the presently disclosed subject matter provides a method of treating a treating a disease characterized by an aberrant immune response in a subject in need of treatment thereof, wherein the method comprises administering a pharmaceutical composition comprising a compound of one of Formulas (III), (IV), (IVa), (IVb), (V), (VI), or (VIa), optionally wherein the disease characterized by an aberrant immune response is an autoimmune disorder or a inflammatory disease.

In some embodiments, the presently disclosed subject matter provides a compound of one of Formulas (I'), (II') or (II"):

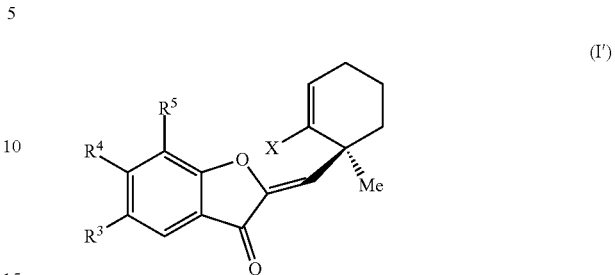

(I')

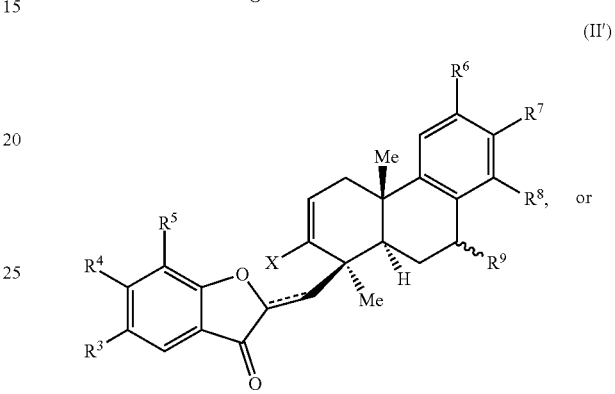

(II')

or

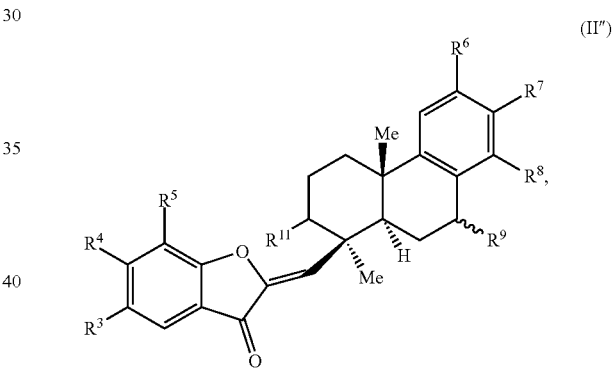

(II")

wherein: ═══ is a double or single bond; X is selected from the group comprising a halide and —O—S(═O)$_2$—R, wherein R is selected from the group comprising alkyl, substituted alkyl, aryl, and substituted aryl, optionally wherein R is —CF$_3$, —CH$_3$, —C$_6$H$_4$CH$_3$, or —C$_n$F$_{2n+1}$, wherein n is an integer between 2 and 12, optionally wherein n is an integer between 2 and 6; $R^3$, $R^4$, and $R^5$ are each independently selected from the group comprising H, alkyl, substituted alkyl, aryl, substituted aryl, alkoxy, aryloxy, amino, and acetamido; $R^6$, $R^7$, and Fe are each independently selected from the group comprising H, alkyl, substituted alkyl, aryl, substituted aryl, alkoxy, aryloxy, amino, acetamido, and nitro; $R^9$ is selected from the group comprising H, hydroxyl, and alkoxy; and $R^{11}$ is selected from the group comprising ═O, hydroxyl, and protected hydroxyl.

In some embodiments, $R^9$ is H. In some embodiments, X is —O—S(═O)$_2$—CF$_3$ (—OTf). In some embodiments, $R^3$, $R^4$, and $R^5$ are each H. In some embodiments, $R^6$, $R^7$, and $R^8$ are each H.

In some embodiments, the compound is selected from the group comprising:

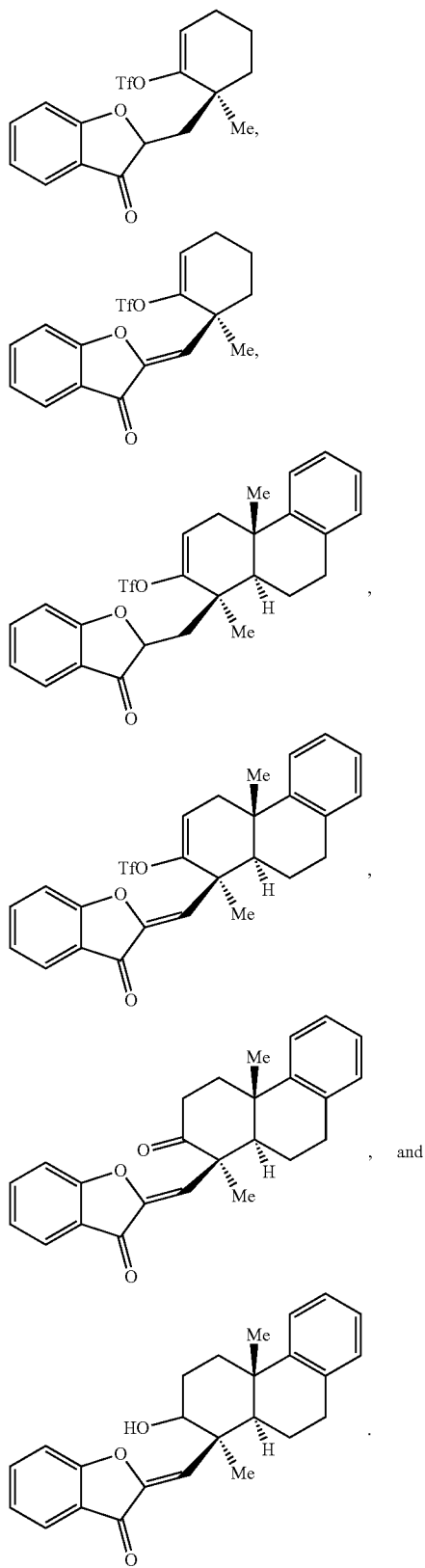

, and

.

In some embodiments, the presently disclosed subject matter provides a method of preparing a phainanoid or a synthetic intermediate thereof, wherein the method comprises: (a) providing a compound comprising a moiety having the structure:

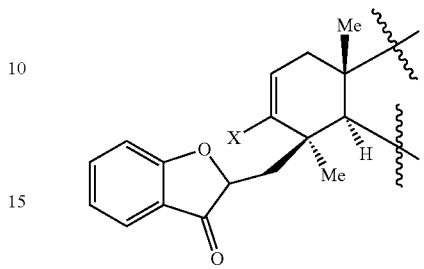

wherein X is a leaving group, optionally wherein X is selected from the group comprising a halide and —O—S(=O)$_2$—R, wherein R is selected from alkyl, substituted alkyl, aryl, and substituted aryl, optionally wherein R is —CF$_3$, —CH$_3$, —C$_6$H$_4$CH$_3$, or —C$_n$F$_{2n+1}$, wherein n is an integer between 2 and 12, optionally wherein n is an integer between 2 and 6; and (b) contacting the compound provided in step (a) with a metal compound, a ligand precursor, and a non-nucleophilic base to perform an intramolecular ketone alkenylation, optionally wherein the metal compound is a palladium (Pd), nickel (Ni) or platinum (Pt) compound and wherein the ligand precursor is a N-heterocyclic carbene (NHC) precursor or a phosphine; thereby providing a synthetic intermediate of a phainanoid. In some embodiments, X is —O—S(=O)$_2$—CF$_3$ (—OTf).

In some embodiments, the metal compound is a Pd compound, optionally wherein the Pd compound is a Pd(II) compound, further optionally wherein the Pd(II) compound is palladium acetate (Pd(OAc)$_2$). In some embodiments, the contacting is performed using between about 5 mole percent (mol %) and about 10 mol % of the metal compound as compared to an amount of the compound provided in step (a), optionally wherein the contacting is performed using about 5 mol % of the metal compound.

In some embodiments, the ligand precursor is a phosphine, optionally wherein the phosphine is a dialkylarylphosphine, further optionally wherein the dialkylarylphosphine comprises one or both of a ferrocenyl group and a tert-butyl group. In some embodiments, the phosphine is 1,2,3,4,5-pentaphenyl-1'-(di-tert-butylphosphino)ferrocene (QPhos). In some embodiments, the contacting is performed using between about 10 mol % and about 20 mol % of the ligand precursor as compared to an amount of the compound provided in step (a) optionally wherein the contacting is performed using about 10 mol % of the ligand precursor.

In some embodiments, the base is selected from the group comprising lithium hexamethyldisilamide (LiHMDS), potassium hexamethyldisilamide (KHMDS), sodium hexamethyldisilamide (NaHMDS), cesium carbonate (Cs$_2$CO$_3$), lithium tert-butoxide (LiO$^t$Bu), potassium tert-butoxide (KO$^t$Bu), and sodium tert-butoxide (NaO$^t$Bu). In some embodiments, the base is LiO$^t$Bu. In some embodiments, the contacting is performed using about 150 mol % of the base compared to an amount of the compound provided in step (a).

In some embodiments, the presently disclosed subject matter provides a compound of Formula (IX):

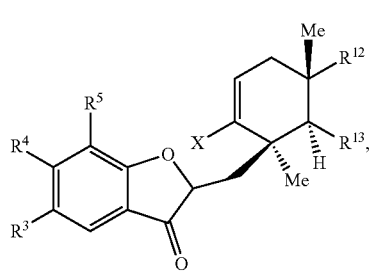

(IX)

wherein: X is selected from the group comprising a halide and —O—S(=O)$_2$—R, wherein R is selected from the group consisting of alkyl, substituted alkyl, aryl, and substituted aryl, optionally wherein R is —CF$_3$, —CH$_3$, —C$_6$H$_4$CH$_3$, or —C$_n$F$_{2n+1}$ where n is an integer between 2 and 12, optionally where n is an integer between 2 and 6; R$^3$, R$^4$, and R$^5$ are each independently selected from the group consisting of H, alkyl, substituted alkyl, aryl, substituted aryl, alkoxy, aryloxy, amino, and acetamido; R$^6$, R$^7$, and R$^8$ are each independently selected from the group consisting of H, alkyl, substituted alkyl, aryl, substituted aryl, alkoxy, aryloxy, amino, acetamido, and nitro; R$^{12}$ is selected from the group consisting of alkyl, substituted alkyl, aralkyl, and substituted aralkyl, and R$^{13}$ is alkyl or substituted alkyl; or where R$^{12}$ and R$^{13}$ together form an optionally substituted mono- or polycyclic structure.

Accordingly, it is an object of the presently disclosed subject matter to provide a method of synthesizing phainanoids and phainanoid analogs, as well as to provide the phainanoid analogs themselves, pharmaceutical compositions thereof, and methods of treating disease using the compositions.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

DETAILED DESCRIPTION

Figure 1:
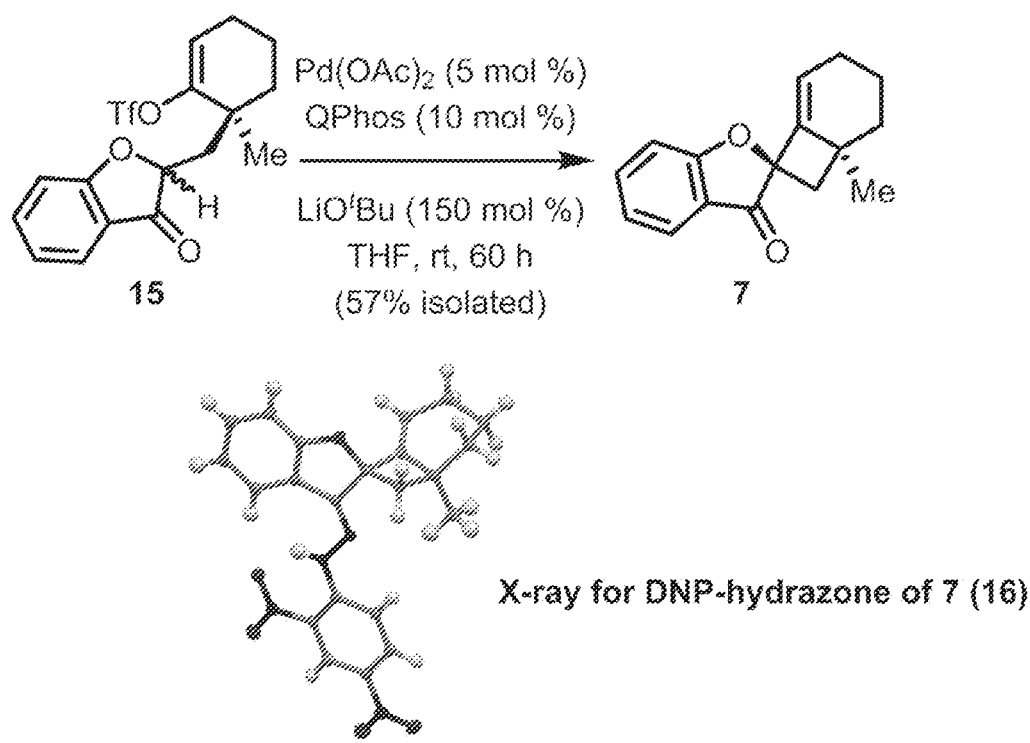
FIG. 1 is a schematic diagram showing: (top) exemplary reaction conditions for an intramolecular ketone alkenylation reaction transforming phainoid analog intermediate 15 into phainanoid analog 7; and (bottom) the structure of the 2,4-dinitrophenyl (DNP)-hydrazone derivative of phainanoid analog 7 (i.e., compound 16) as determined by X-ray crystallography. The reactions conditions for the exemplary reaction are: 5 mole percent (mol %) palladium acetate (Pd(OAc)$_2$), 10 mol % 1,2,3,4,5-pentaphenyl-1'-(di-tert-butylphosphino)-ferrocene (QPhos) and 150 mol % lithium tert-butoxide (LiO$^t$Bu) with 100 mol % compound 15 in tetrahydrofuran (THF) at room temperature (rt) for 60 hours, The exemplary reaction conditions provide phainanoid analog 7 in 57% yield.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist, unless otherwise indicated.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of yield, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

Numerical ranges recited herein by endpoints include all numbers and fractions subsumed within that range (e.g. 1 to 5 includes, but is not limited to, 1, 1.5, 2, 2.75, 3, 3.90, 4, and 5).

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—);

and ethylenedioxyl (—O—(CH$_2$)$_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

As used herein, the term "acyl" refers to an organic carboxylic acid group wherein the —OH of the carboxylic acid group has been replaced with another substituent. Thus, an acyl group can be represented by RC(=O)—, wherein R is an alkyl, substituted alkyl, aralkyl, substituted aralkyl, aryl or substituted aryl group as defined herein. As such, the term "acyl" specifically includes arylacyl groups, such as a phenacyl group. Specific examples of acyl groups include acetyl and benzoyl. "Cyclic" and "cycloalkyl" refer to a non-aromatic mono- or multi-cyclic ring system of about 3 to about 10 carbon atoms, e.g., 3, 4, 5, 6, 7, 8, 9, or 10 carbon atoms. The cycloalkyl group can be saturated or partially unsaturated. The cycloalkyl group also can be optionally substituted with an alkyl group substituent as defined herein. There can be optionally inserted along the cyclic alkyl chain one or more oxygen. Representative monocyclic cycloalkyl rings include cyclopentyl, cyclohexyl, and cycloheptyl. Multicyclic cycloalkyl rings include adamantyl, octahydronaphthyl, decalin, camphane, and noradamantyl.

"Alkoxyl" refers to an alkyl-O— group wherein alkyl is as previously described, including substituted alkyl. The term "alkoxyl" as used herein can refer to, for example, methoxyl, ethoxyl, propoxyl, isopropoxyl, butoxyl, t-butoxyl, and pentoxyl. The terms "alkoxy" and "oxyalkyl" can be used interchangably with "alkoxyl".

"Aryloxyl" and "aryloxy" refer to an aryl-O— group wherein the aryl group is as previously described, including a substituted aryl. The term "aryloxyl" as used herein can refer to phenyloxyl or hexyloxyl, and to alkyl, substituted alkyl, or alkoxyl substituted phenyloxyl or hexyloxyl.

"Aralkyl" refers to an aryl-alkyl- or an -alkyl-aryl group wherein aryl and alkyl are as previously described, and can include substituted aryl and substituted alkyl. Thus, "substituted aralkyl" can refer to an aralkyl group comprising one or more alkyl or aryl group substituents. Exemplary aralkyl groups include benzyl, phenylethyl, and naphthylmethyl.

"Aralkyloxyl," "aralkoxyl" and "alalkoxy" refer to an aralkyl-O— group wherein the aralkyl group is as previously described. An exemplary aralkyloxyl group is benzyloxyl. "Substituted aralkyoxyl" can refer to an aralkoxyl group wherein the alkyl and/or aryl portion of the aralkyl are substituted by one or more alkyl or aryl group substituents.

The term "olefin" as used herein refers to a compound or moiety comprising an alkenyl group, i.e., a carbon-carbon double bond, e.g., having the structure R$_2$C=CR$_2$, wherein each R group is independently selected from the group including H, alkyl, substituted alkyl, aralkyl, substituted aralkyl, aryl, substituted aryl, and monovalent alkyl group substituents (e.g., halo, arylamino, acyl, hydroxyl, aryloxyl, alkoxyl, alkylthio, arylthio, aralkyloxyl, aralkylthio, carboxyl, alkoxycarbonyl, and cycloalkyl).

The term "carbonyl" refers to the group —C(=O)—. The term "carbonyl carbon" refers to a carbon atom of a carbonyl group. Other groups such as, but not limited to, acyl groups, anhydrides, aldehydes, esters, lactones, amides, ketones, carbonates, and carboxylic acids, include a carbonyl group.

The term "oxo" refers to the =O group.

The term "aldehyde" can refer to the —C(=O)H group.

The term "ketone" can refer to the —R'—C(=O)—R group or the —C(=O)R group (i.e., when the —C(=O)R group is directly substituted on a carbon atom), wherein R is alkyl, substituted alkyl, aralkyl, substituted aralkyl, aryl, or substituted aryl and R' is optionally substituted alkylene or arylene.

The term "acetamido" can refer to the —NH—C(=O)CH$_3$ group.

The term "amine" refers to a molecule having the formula N(R)$_3$, or a protonated form thereof, wherein each R is independently H, alkyl, substituted alkyl, aryl, substituted aryl, aralkyl, substituted aralkyl, or wherein two R groups together form an alkylene or arylene group. The term "primary amine" refers to an amine wherein at least two R groups are H. The term "secondary amine" refers to an amine wherein only one R group is H. The term "alkylamine" can refer to an amine wherein two R groups are H and the other R group is alkyl or substituted alkyl. "Dialkylamine" can refer to an amine where two R groups are alkyl. "Arylamine" can refer to an amine wherein one R group is aryl. Amines can also be protonated, i.e., have the formula [NH(R)$_3$]$^+$.

The term "amino" refers to the group —N(R)$_2$ wherein each R is independently H, alkyl, substituted alkyl, aryl, substituted aryl, aralkyl, or substituted aralkyl. The terms "aminoalkyl" and "alkylamino" can refer to the group —N(R)$_2$ wherein each R is H, alkyl or substituted alkyl, and wherein at least one R is alkyl or substituted alkyl. "Arylamino" and "aminoaryl" refer to the group —N(R)$_2$ wherein each R is H, aryl, or substituted aryl, and wherein at least one R is aryl or substituted aryl, e.g., aniline (i.e., —NHC$_6$H$_5$).

The terms "halo", "halide", or "halogen" as used herein refer to fluoro, chloro, bromo, and iodo groups.

The terms "hydroxyl" and "hydroxy" refer to the —OH group.

The terms "carboxylate" and "carboxylic acid" can refer to the groups —C(=O)O$^-$ and —C(=O)OH, respectively. The term "carboxyl" can also refer to the —C(=O)OH group. In some embodiments, "carboxylate" or "carboxyl" can refer to either the —C(=O)O$^-$ or —C(=O)OH group.

The term "phosphine" as used herein refers to compound of the structure PR$_3$ group, where each R group is independently selected from H, alkyl, substituted alkyl, aralkyl, substituted aralkyl, aryl, and substituted aryl.

A solid line crossed or terminated by a wavy line, e.g., in the structure:

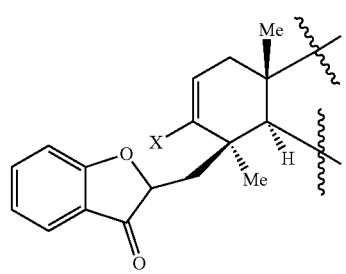

is used in the chemical formulas described herein to indicate the attachment site of the specified structure or substituent to another chemical group or structure.

A dashed line representing a bond in a chemical formula indicates that the bond can be either present or absent. For example, the chemical structure:

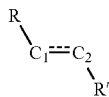

refers to compounds wherein $C_1$ and $C_2$ can be joined by either a single or double bond.

A wavy line representing a bond in a chemical structure, such as in the structure:

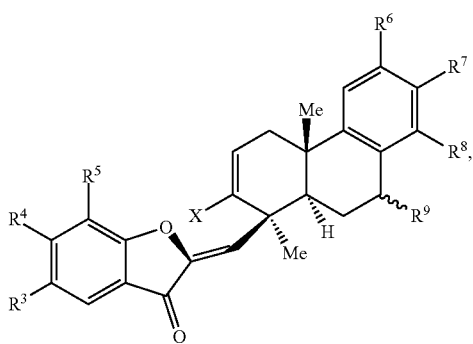

where $R^9$ is attached to a ring carbon atom via a wavy line, represents unspecified stereochemistry of the bond, wherein the compound can be a single stereoisomer or a mixture of the two possible stereoisomers. However, in some embodiments, a straight line representing a bond (i.e., a bond to a stereocenter) can also represent unspecified stereochemistry, wherein the compound can be a single stereoisomer or a mixture of two possible stereoisomers.

The term "monovalent" as used herein refers to a chemical moiety that has one site available for chemical bonding to another chemical moiety. Thus, a "monovalent moiety" can be a part of whole molecule that is attached to the remainder of the whole molecule via an attachment at one site on the monovalent moiety.

The term "bivalent" as used herein refers to a chemical moiety that has two sites available for chemical bonding to another chemical moiety or moieties.

The term "hydroxyl protecting group" refers to groups that are known in the art of organic synthesis for masking hydroxyl groups during chemical group transformations elsewhere in the molecule. Accordingly, hydroxyl protecting groups are groups that can replace the hydrogen atom of a hydroxy group on a molecule and that are stable and non-reactive to reaction conditions to which the protected molecule is to be exposed. Suitable hydroxyl protecting groups are described, for example, in Greene and Wuts, Protective Groups in Organic Synthesis, 3$^{rd}$ Edition; New York, John Wiley & Sons, Inc., 1999. Hydroxyl protecting groups include, but are not limited to, groups that can be reacted with hydroxyl groups to form ethers, such as silyl ethers (e.g., trimethylsilyl (TMS), triethylsilyl (TES), tert-butyldimethylsilyl (TBDMS, sometimes also referred to as TBS), t-butyldiphenylsilyl (TBDPS), or phenyldimethylsilyl ethers) substituted methyl ethers (e.g., methoxymethyl (MOM), benzyloxymethyl (BOM), tetrahydropyranyl (THP)), substituted ethyl ethers, benzyl ethers and substituted benzyl ethers; esters (e.g., acetate, formate, chloroacetate); and carbonates. The term "protected hydroxyl" can refer to the group —OR, wherein R is a hydroxyl protecting group.

The term "aprotic solvent" refers to a solvent molecule which can neither accept nor donate a proton. Examples of aprotic solvents include, but are not limited to, ethyl acetate; carbon disulphide; ethers, such as, diethyl ether, tetrahydrofuran (THF), ethylene glycol dimethyl ether, dibutyl ether, diphenyl ether, MTBE, and the like; aliphatic hydrocarbons, such as hexane, pentane, cyclohexane, and the like; aromatic hydrocarbons, such as benzene, toluene, naphthalene, anisole, xylene, mesitylene, and the like; and symmetrical halogenated hydrocarbons, such as carbon tetrachloride, tetrachloroethane, and dichloromethane. Additional aprotic solvents include, for example, acetone, acetonitrile, butanone, butyronitrile, chlorobenzene, chloroform, 1,2-dichloroethane, dimethylacetamide, N,N-dimethylformamide (DMF), dimethylsulfoxide (DMSO), and 1,4-dioxane.

The term "protic solvent" refers to a solvent molecule which contains a hydrogen atom bonded to an electronegative atom, such as an oxygen atom or a nitrogen atom. Typical protic solvents include, but are not limited to, carboxylic acids, such as acetic acid, alcohols, such as methanol and ethanol, amines, amides, and water.

The term "non-nucleophilic base" refers to an organic base that can remove a proton but that is only modestly or poorly nucleophilic (e.g., is unlikely to form a bond with an electron deficient group, such as a carbonyl carbon). Typically, non-nucleophilic bases are sterically hindered, i.e., comprising bulky substituents. Non-nucleophilic bases typically used in organic synthesis include, but are not limited to, amines and nitrogen heterocycles, such as diisopropylethylamine (DIPEA); sterically hindered alkoxides, such as lithium tert-butoxide (LiO$^t$Bu), sodium tert-butoxide (NaO$^t$Bu), and potassium tert-butoxide (KO$^t$Bu); anions, such as lithium diisopropylamide (LDA), silicon-based amides, such as sodium hexamethyldisilamide (NaHMDS), lithium hexamethyldisilamide (LiHMDS), or potassium hexamethyldisilamide (KHMDS); lithium tetramethyl piperidine (LiTMP); and hydrides (e.g., sodium hydride (NaH) or potassium hydride (KH).

The term "phainanoid" as used herein can refer to a compound having the structure of a triterpenoid natural product isolated from *Phyllanthus hainanensis*, such as one of compounds 1-6 shown in Scheme 1, below.

The terms "synthetic intermediate of a phainanoid" and "phainanoid synthetic intermediate" as used herein refer to a compound that can be used as an intermediate in a chemical synthesis of a phainanoid.

The term "phainanoid analog" as used herein refers to a synthetic product based on the chemical structure of (or part of the chemical structure of) a natural phainanoid compound, but that does not have the same chemical structure as one of the natural phainanoids. In some embodiments, the term "phainanoid analog" refers to a synthetic product that comprises a benzofuran-based-4,5-spirocycle moiety, such as a product that comprises a benzofuranone-4,5-spirocycle moiety and/or wherein the spirocycle group is a cyclobutane and/or wherein the spirocycle group further comprises an exocyclic olefin group, such as a strained exocyclic olefin group, optionally wherein the strained exocyclic olefin group is part of a ring structure (e.g., a cyclohexene).

II. Synthesis of Benzofuranone-4,5-Spirocycles

As described hereinabove, the recently discovered natural product phainanoid class of compounds exhibit potent immunosuppressive activities. However, they are found in nature in relatively low amounts. They also possess relatively complex structures, including 10 cyclic moieties and at least 13 chiral centers.

In some aspects, the presently disclosed subject matter provides a synthetic route to the "western" part of the phainanoid structure. Challenges to forming the "western" part of the phainanoid structure include: (a) forming a highly strained cyclobutane that also comprises a strained exocyclic olefin; and (b) controlling the diastereoselectivety during the ring closure step that forms the cyclobutane. Two phainanoid analogs based on the "western" part of the phainanoid structural skeleton were designed to provide model compounds for developing a synthetic route. See Scheme 1, below. More particularly, as shown in Scheme 1, phainanoid analogs 7 and 8 both include the benzofuranone-4,5-spirocycle motif of the natural phainanoids, and further comprise a strained exocyclic olefin present as part of a cyclohexene ring, thus mimicking the "western" part of the phainanoids.

Scheme 1. Phainanoids A-F (1-6) and phainanoid analog compounds 7 and 8.

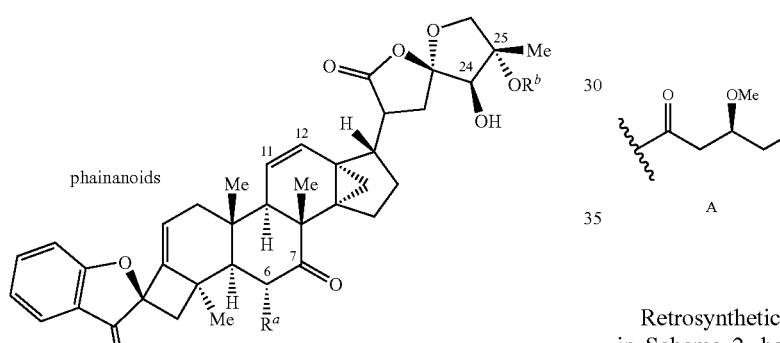

1 $R^a$ = H, $R^b$ = H
1 $R^a$ = OH, $R^b$ = H
3 $R^a$ = OH, $R^b$ = Me
4 $R^a$ = OH, $R^b$ = CO(CH$_2$)$_5$OH
5 $R^a$ = OH, $R^b$ = A, $R^c$ = OH
6 $R^a$ = OH, $R^b$ = A, $R^c$ = OMe

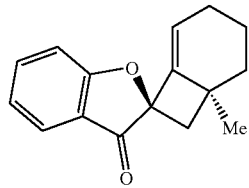

7

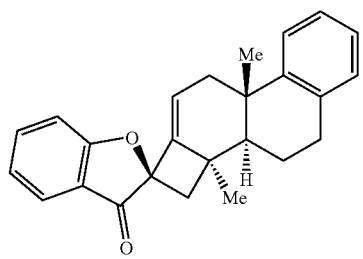

8

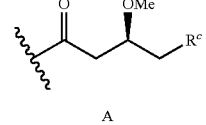

A

Retrosynthetic analysis of phainanoid analog 7 is shown in Scheme 2, below. In a final step of the synthesis, the cyclobutane ring is formed via intramolecular alkenylation of ketone intermediate 15. Ketone intermediate 15 includes a triflate (—OTf) group or other good leaving group at the vinylic position of the cyclohexene ring. Ketone 15 can be formed via aldol condensation and subsequent reduction of aldehyde 12 and benzofuran-3(2H)-one (3-coumaranone) 13. Aldehyde 12 can be accessed from commercially available β-ketoester 9.

Scheme 2. Retrosynthetic Analysis for Phainanoid Analog 7.

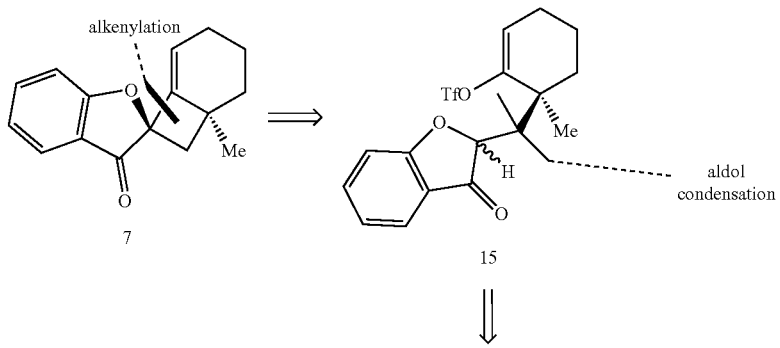

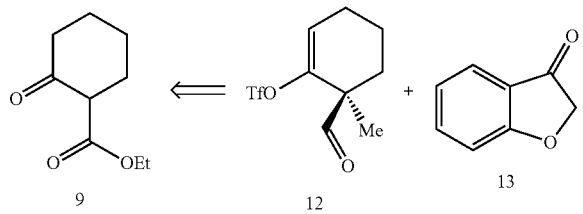

More particularly, the synthesis of ketone intermediate 15 is shown below in Scheme 3. As described further in the Examples, aldehyde 12 was prepared in four steps with high overall yields from β-ketoester 9 through a sequence of methylation (see Hayashi et al., Tett. Lett. 2005, 46, 681), triflation of the ketone, DIBAL-H reduction and Dess-Martin oxidation. The aldol condensation between 12 and 3-coumaranone 13 was found most efficient in the presence of basic alumina (see Kwon et al., J. Med. Chem. 2015, 58, 1100), which provided enone 14 in 84% yield with a complete Z-selectivity. Selective reduction of the trisubstituted enone olefin in compound 14 in the presence of a vinyl triflate moiety turned out to be somewhat challenging. See Example 3, below. Eventually, Pd/C-catalyzed hydrogenation was found to chemoselectively reduce the enone olefin to compound 15, e.g., in 91% yield when using toluene/DCM (50:1) as the optimal solvent combination.

Scheme 3. Synthesis of Phainanoid Analog Intermediate 15.

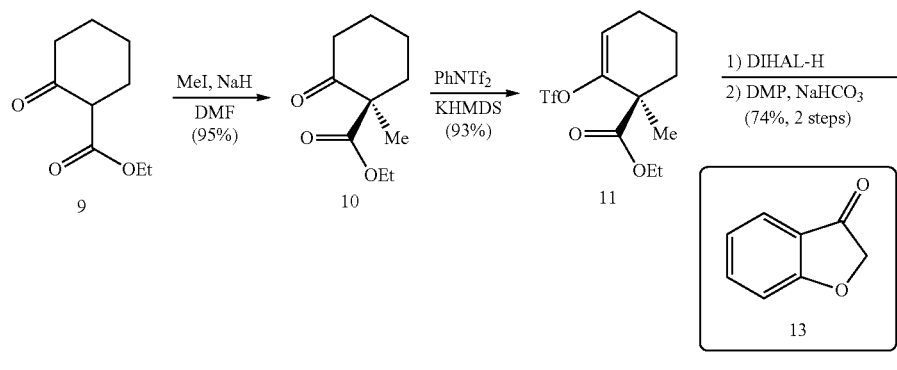

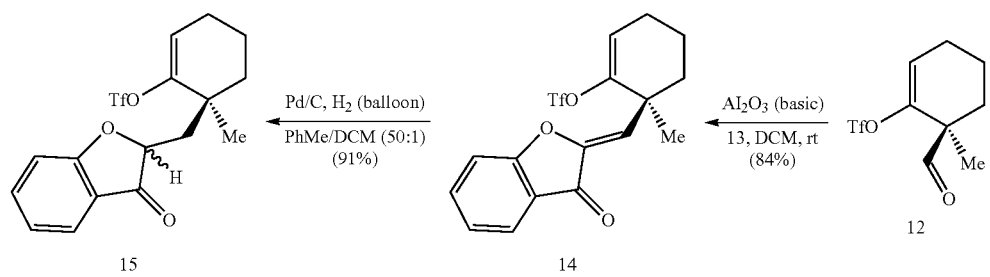

With compound 15 in hand, the stage was set to explore the intramolecular alkenylation for constructing the 4,5-spirocycle. While palladium-catalyzed ketone alkenylations have been well established (see Ankner et al., Chem. Eur. J. 2013, 19, 1858), use of an intramolecular alkenylation to access four-membered rings remains elusive. See Chen et al., Org. Lett. 2008, 10, 5285. The challenge is anticipated to come from the difficult reductive elimination step to form a highly strained ring. Reductive elimination can benefit from the use of sterically hindered ligands. For example, various tert-butyl-substituted phosphine ligands promote the palladium-catalyzed intermolecular alkenylation of ketones, with 1,2,3,4,5-pentaphenyl-1-(di-tert-butylphosphino)ferrocene (QPhos) being the most efficient phosphine. See Grigalunas et al., Org. Lett. 2014, 16, 3970. Intramolecular alkenylation of compound 15 using QPhos as the ligand was investigated. Alkenylation results using different conditions are shown in Table 1, below. Using LiHMDS as the base in room temperature THF as the solvent, the desired 4,5-spirocycle 7 was obtained albeit in 21% yield. See Table 1, entry 1. LiO$^t$Bu was later found to be the best base (see Table 1 entry 4) among all the bases examined. See Table 1, entries 1-7. Removing residual water in the reaction vessel by flame drying also significantly improved the yield to 60%. See Table 1, entry 8. Reactions carried out at higher concentrations resulted in incomplete conversions of 15. See Table 1, entries 9-10. Using toluene instead of THF resulted in poor product formation. See Table 1, entry 12. The optimal conditions were established to be 5 mol % of Pd(OAc)$_2$, 10 mol % of QPhos and 1.5 equiv of LiO$^t$Bu in THF, which provided phainanoid analog 7 in 65% (57% isolated) yield. See Table 1, entry 11. The structure of phainanoid analog 7 was unambiguously confirmed by X-ray crystallography of the corresponding DNP-hydrazone derivative. See FIG. 1.

TABLE 1

Palladium-Catalyzed Intramolecular Alkenylation of Ketone 15[a]

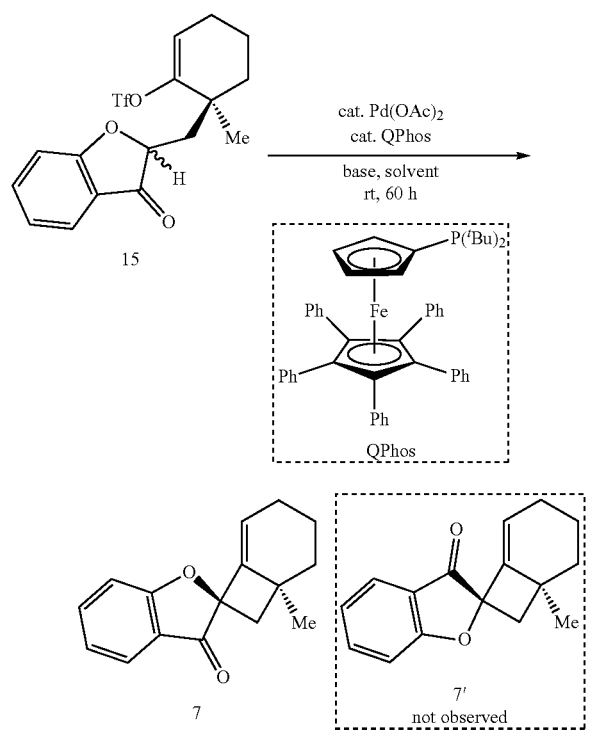

TABLE 1-continued

| Entry | Base (1.5 equiv) | Solvent | Yield (7)/% |
|---|---|---|---|
| 1 | LiHMDS | THF (0.05M) | 21 |
| 2 | KHMDS | THF (0.05M) | 34 |
| 3 | NaHMDS | THF (0.05M) | 20 |
| 4 | LiO$^t$Bu | THF (0.05M) | 44 |
| 5 | KO$^t$Bu | THF (0.05M) | 25 |
| 6 | NaO$^t$Bu | THF (0.05M) | 14 |
| 7 | Cs$_2$CO$_3$ | THF (0.05M) | 35 |
| 8[b] | LiO$^t$Bu | THF (0.05M) | 60 |
| 9[b] | LiO$^t$Bu | THF (0.10M) | 51 (2) |
| 10[b] | LiO$^t$Bu | THF (0.20M) | 39 (12) |
| 11[b,c] | LiO$^t$Bu | THF (0.05M) | 65 |
| 12[b,c] | LiO$^t$Bu | PhMe (0.05M) | Trace |

[a]Reactions were conducted on a 0.05 mmol scale in a 4 mL vial sealed with a PTFE lined cap. Unless otherwise noted, 10 mol % of Pd(OAc)$_2$ and 20 mol % of QPhos were used. The yields were determined by $^1$H NMR using 1,1,2,2-tetrachloroethane as the internal standard. Recovery of starting material is noted in parenthesis.
[b]Vials were flame-dried.
[c]5 mol % of Pd(OAc)$_2$ and 10 mol % of QPhos were used.

Figure 2:
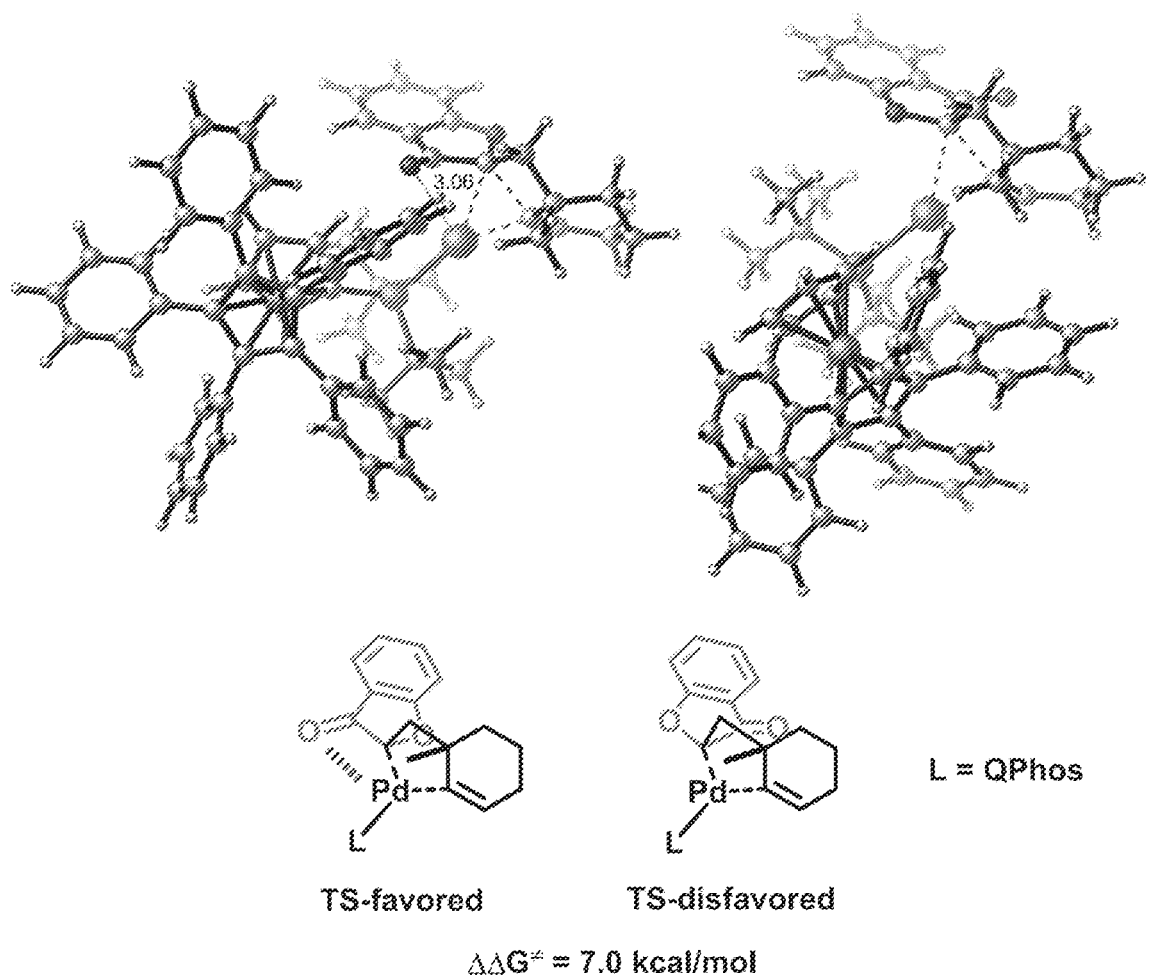
FIG. 2 is the density functional theory (DFT)-calculated diastereochemistry determining transition states (TS) for the palladium (Pd)-catalyzed intramolecular alkenylation reaction described in FIG. 1. Ligand (L) of the Pd atom is 1,2,3,4,5-pentaphenyl-1'-(di-tert-butylphosphino)-ferrocene (QPhos). The structures on the left represent the favored TS, while those on the right represent the disfavored TS. The difference in free energy of activation (ΔΔG$^≠$ between the two different TSs is about 7.0 kilocalories per mole (kcal/mol).

The other possible diastereomer of the product (7') was not observed during the intramolecular alkenylation. Accordingly, diastereoselectivities of at least 2:1, preferably at least 5:1, more preferably at least 10:1 and most preferably 50:1 are possible. To understand the origin of such a diastereoselectivity, computational studies via density functional theory (DFT) calculations were carried out. These calculations suggest that during the reductive elimination step, the transition state that forms the desired diastereomer is about 7.0 kcal/mol lower in energy than the undesired one. See FIG. 2. The stabilization is likely due to a favorable interaction between the carbonyl lone pair electrons and the palladium (the Pd—O distance is computed to be 3.06 Å).

To test the influence of adjacent stereocenters and fused-ring structures on the 4,5-spirocycle formation, a more complex model compound, phainanoid analog 8 (see Scheme 1, above) was prepared. Phainanoid analog 8 has a hexacyclic core structure that includes the benzofuranone-4,5-spirocycle motif of the natural phainanoids. A strategy employing a vinyl oxirane-mediated polyene cyclization (see Rajendar and Corey, J. Am. Chem. Soc. 2015, 137, 5837) was used to prepare the precursor for the intramolecular alkenylation. See Scheme 4. While aldehyde 19 has been synthesized previously (see Zhao et al., Chem. Commun. 2008, 1353), a modified route was developed from inexpensive geranyl acetate 17 through a three-step sequence involving a copper-catalyzed allylic coupling, chemoselective epoxidation and oxidative cleavage of the epoxide. See Zhao et al., Chem. Commun. 2008, 1353. Under Still's modified Horner-Wadsworth-Emmons olefination conditions (see Still and Gennari, Tett. Lett. 1983, 24, 4405. Z-olefin 21 was obtained selectively in 79% yield. Subsequent treatment of ester 21 with DIBAL-H led to allylic alcohol 22 in a quantitative yield. Directed epoxidation of the allylic alcohol followed by Parikh-Doering oxidation efficiently yielded the corresponding epoxy aldehyde 23. Basic alumina-promoted aldol condensation between aldehyde 23 and 3-coumaranone (13) smoothly delivered vinyl epoxide 24. All these reactions could be performed on gram scales.

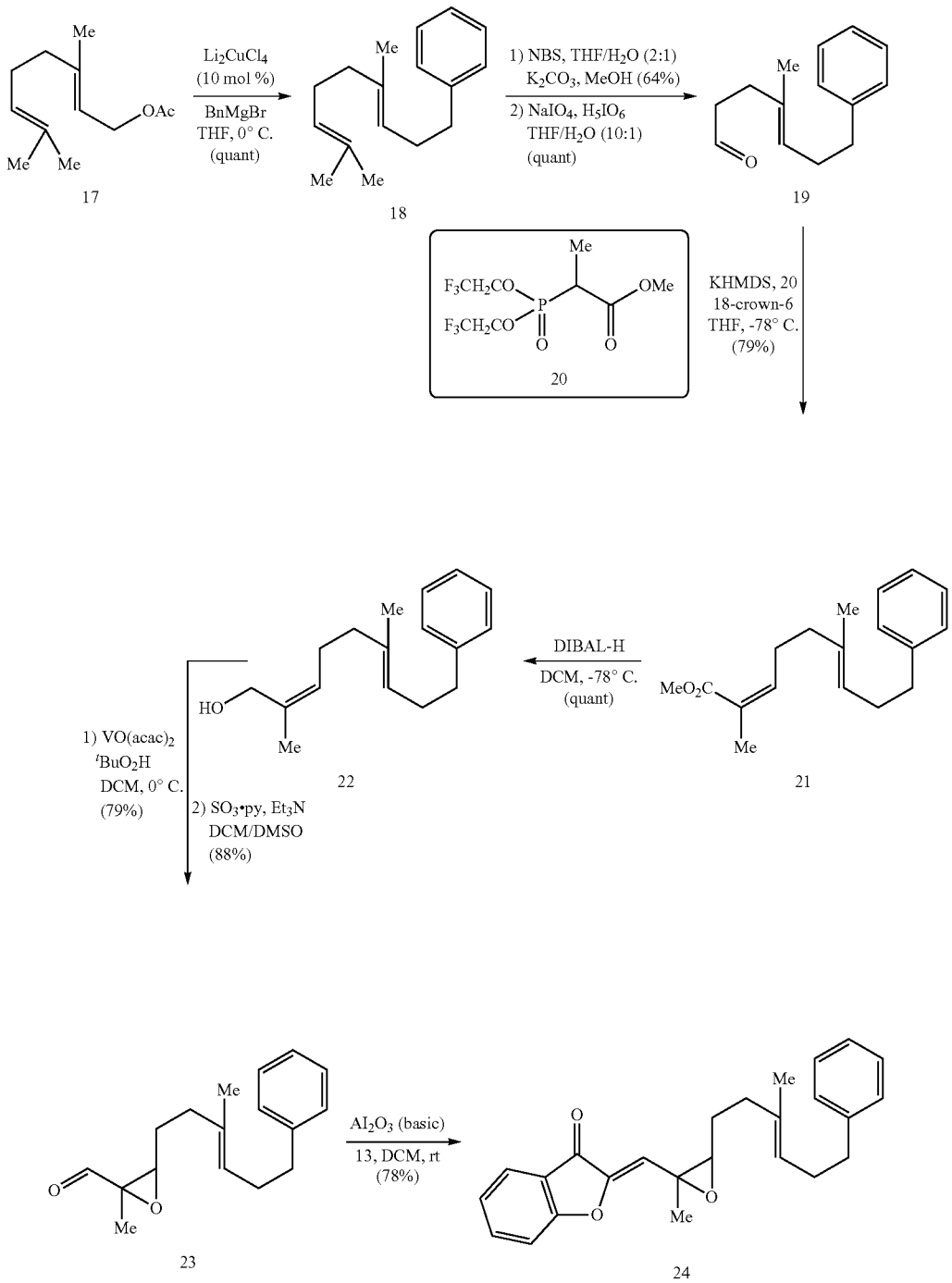

Scheme 4. Synthesis of Phainanoid Analog Intermediate 24.

Figure 3:
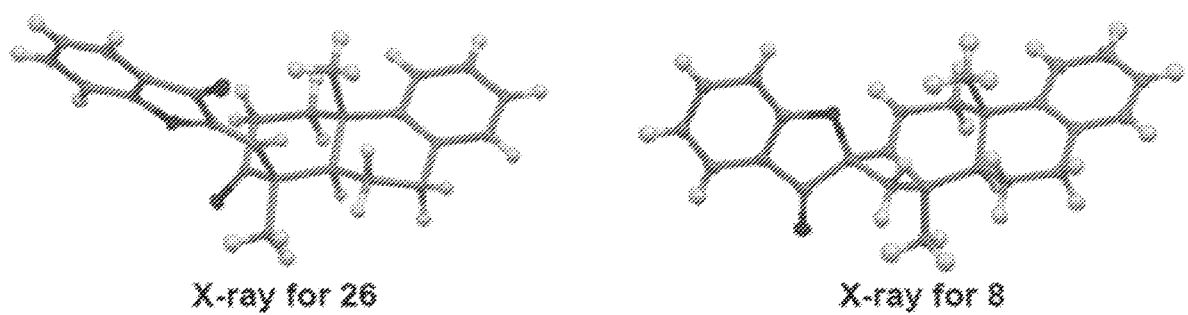
FIG. 3 is a schematic drawing showing the structures of (right) phainanoid analog 8 and (left) the 2,4-dinitrophenyl (DNP)-hydrazone derivative of phainanoid analog 8 (compound 26) as determined by X-ray crystallography.

With an effective route to 24, the Lewis acid-mediated polyene cyclization was then explored. See Scheme 5, below. The reaction occurred rapidly with SnCl₄ furnishing tricyclic 25 with a trans-decaline core in 70% yield. Treatment of alcohol 25 with Dess-Martin periodinane gave ketone 26, the structure of which was further confirmed by X-ray crystallography. Subsequent triflation of ketone 26, followed by the Pd/C-catalyzed chemoselective hydrogenation provided compound 28. The Pd(OAc)₂/QPhos-catalyzed intramolecular alkenylation of compound 28 was surprisingly found to be more effective in toluene than in THF. See Table 2, below. At an elevated reaction temperature (60° C.), 4,5-spirocycle 8 was ultimately isolated in 83% yield with >20:1 diastereomeric ratio. See Table 2, entry 5. The structure of 8 was also characterized by X-ray crystallography. See FIG. 3.

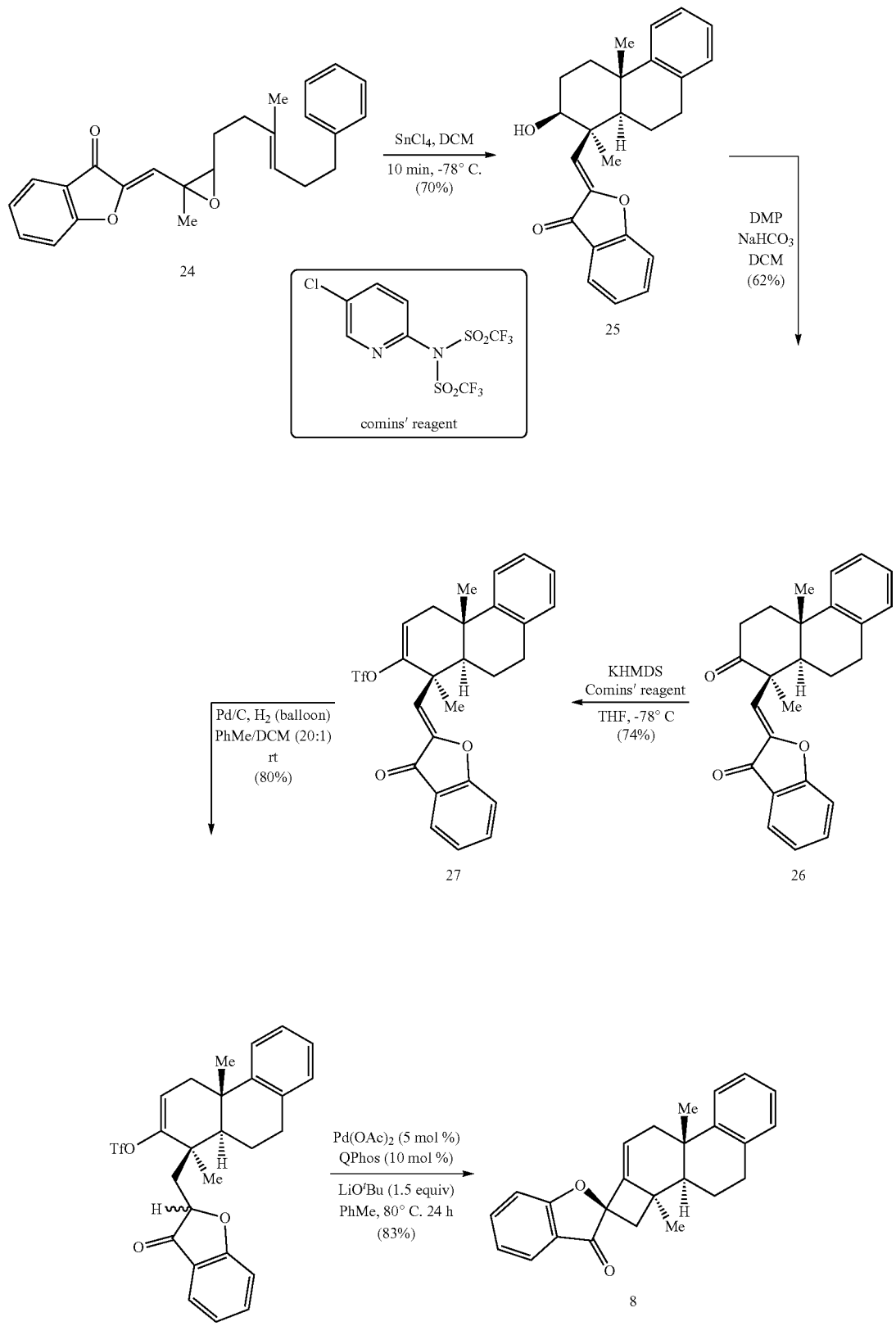
Scheme 5. Synthesis of Phainanoid Analog 8.

TABLE 2

Palladium Catalyzed Alkenylation of 28[a]

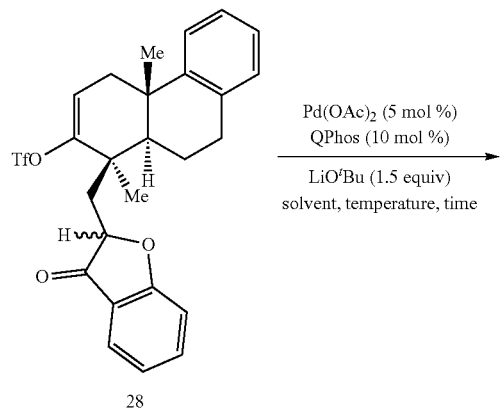 [SMILES: C[C@]1(CC2Oc3ccccc3C2=O)C(OS(=O)(=O)C(F)(F)F)=CC[C@]2(C)c3ccccc3CC[C@@H]12]

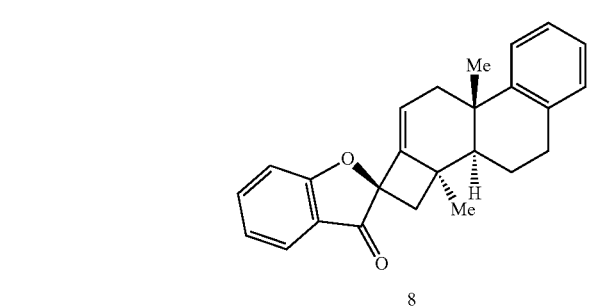 [SMILES: C[C@]12C[C@@]3(Oc4ccccc4C3=O)C1=CC[C@]1(C)c3ccccc3CC[C@@H]21]

| Entry | Solvent | Temperature | Time (h) | Yield (%) |
|---|---|---|---|---|
| 1 | THF | RT | 48 | 14 |
| 2[b] | THF | RT | 48 | 14 |
| 3 | PhMe | RT | 48 | 56 |
| 4 | PhMe | 50° C. | 24 | 62 |
| 5 | PhMe | 60° C. | 24 | 83 |
| 6 | PhMe | 70° C. | 24 | 76 |
| 7 | PhMe | 80° C. | 24 | 68 |
| 8[c] | PhMe | 60° C. | 24 | 67 |

[a]Unless otherwise noted, the reaction was conducted at 0.05 mmol scale and 0.05M concentration. Isolated yields were given.
[b]The reaction was conducted on 0.1M concentration. An NMR yield was given with 1,3,5-trimethoxybenzene as the internal standard.
[c]5 mol % of Pd(QPhos)₂ was used instead of Pd(OAc)₂ and QPhos.

Thus, the presently disclosed subject matter provides a general and practical route to access the western part of phainanoids, the part of the molecule that contains a unique 4,5-spirocyclic ether motif. In some embodiments, the presently disclosed synthesis features a highly diastereoselective metal-catalyzed intramolecular alkenylation to construct a highly strained system. While the syntheses described above employed a palladium metal catalyst system, other metal catalysts systems, such as nickel or platinum catalyst systems, can also be used.

Figure 4A:
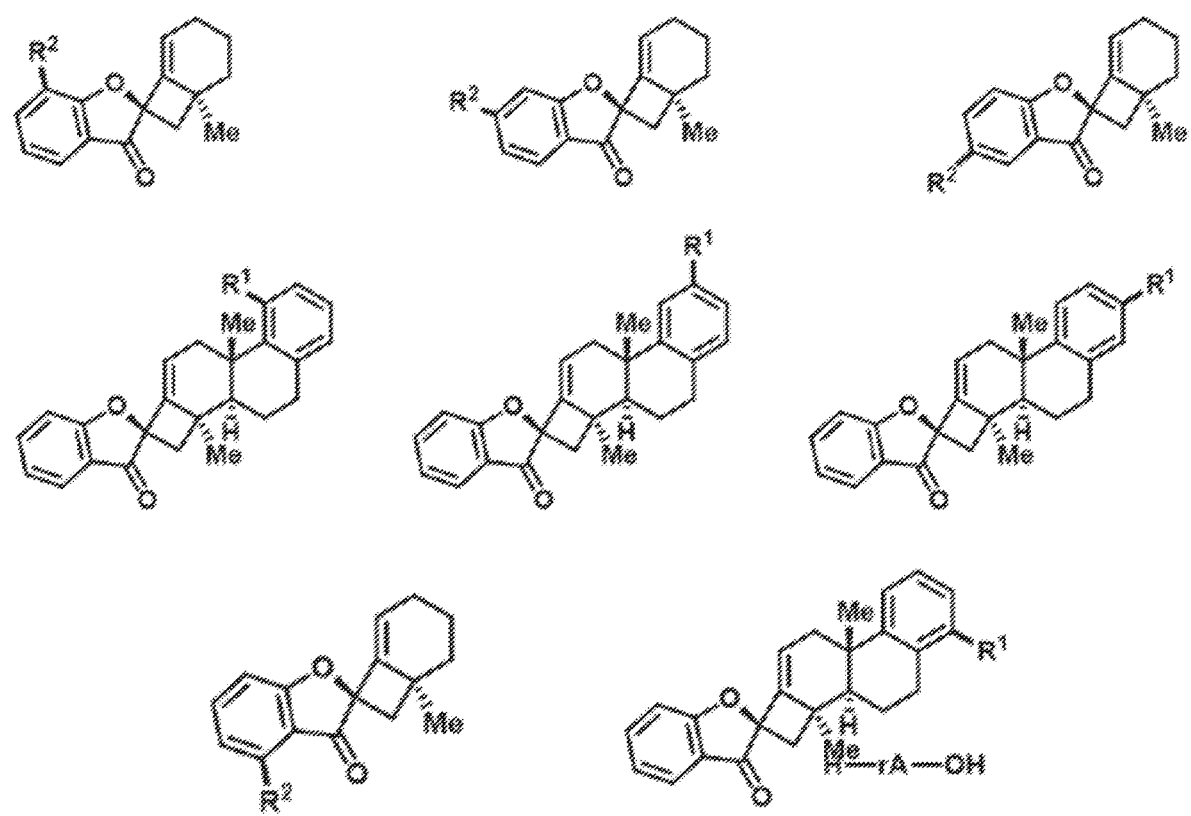
FIG. 4A is a schematic drawing showing chemical structures of exemplary phainanoid analogs of the presently disclosed subject matter.
Figure 4B:
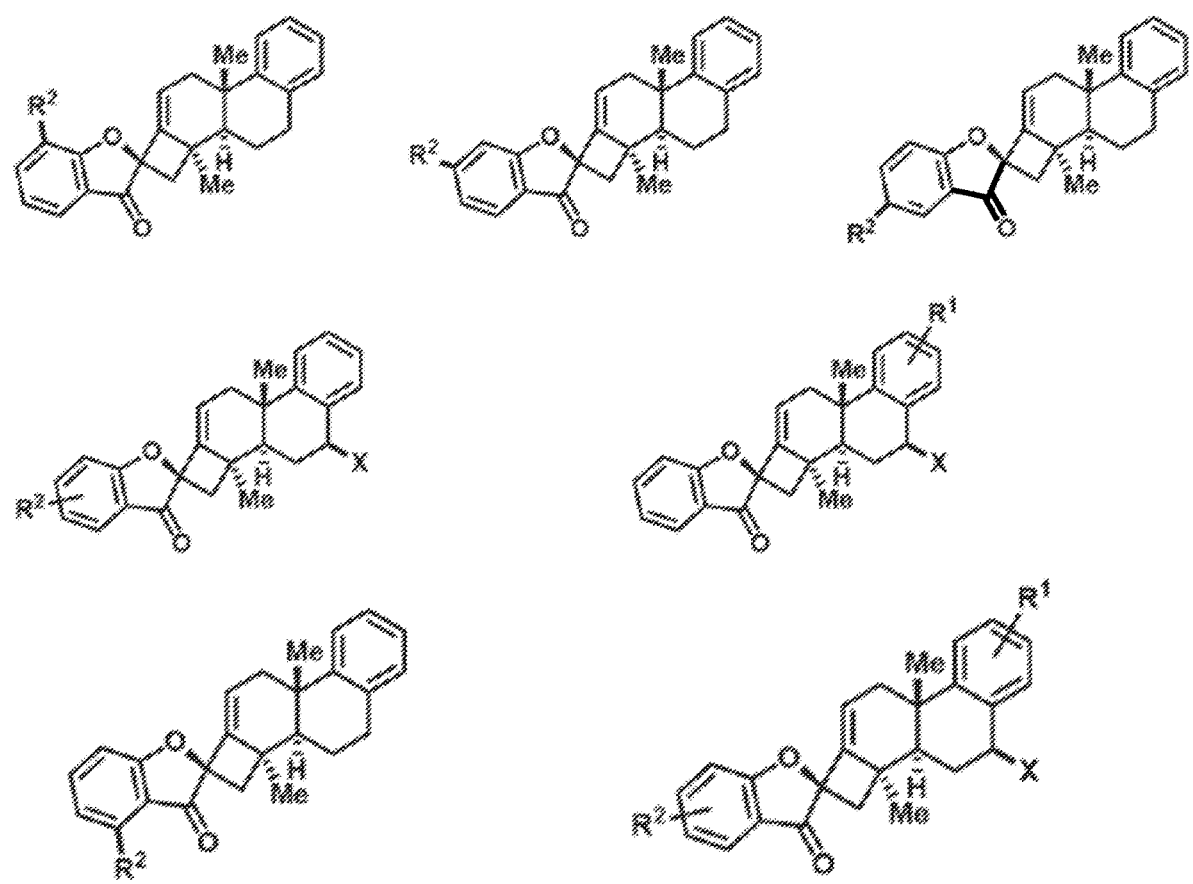
FIG. 4B is a schematic drawing showing chemical structures of additional exemplary phainanoid analogs of the presently disclosed subject matter.

Based on the exemplary synthetic routes to phainanoid analog compound 7 and phainanoid compound 8 described above, analogous syntheses can be performed to provide numerous phainanoid analogs with similar scaffolds. See Scheme 6, below and FIGS. 4A and 4B. For example, for Type I phainanoid analogues, based on compound 7, a variety of different substituents ($R^2$) can be incorporated at different locations on the benzene ring. See FIG. 4A. For Type II analogs, based on compound 8, different substituents can be introduced at different locations of the benzene ring of the benzofuranone moiety (ring A) and/or of the second benzene ring (ring B). See FIGS. 4A and 4B. Modification on both benzene rings in the Type II analogs (see FIG. 4B) can be used to extend the phainanoid analog scope by providing analogs with numerous combinations of benzene ring substituents, including compounds with multi-substituted benzene rings (i.e., compounds wherein either benzene ring can have more than one substituent). Moreover, considering the special reactivity of the benzylic position of second benzene ring present in the Type II analogs, a benzylic substituent (Z), such as a hydroxyl or oxo group, could be introduced to provide additional mimics of the natural phainanoids. See FIG. 4B. For instance, a Z substituent can be added through various benzylic oxidation and hydroxylation approaches as would be obvious to one or ordinary skill in the art in view of the present disclosure. A Z substituent could be added to the molecule after the intramolecular ketone alkenylation reaction (e.g., using reagents or reagent combinations such as, but not limited to, potassium permanganate ($KMnO_4$), pyridinium chlorochromate (PCC), chromium trioxide/acetic acid ($CrO_3$/HOAc), N-bromosuccinimide/calcium carbonate ($NBS/CaCO_3$), oxone/KBr, and $NaClO/Co(Ac)_2$/TEMPO). Alternatively, the Z substituent can be introduced prior to the poly-ene cyclization reaction (e.g., to compound 24 in Scheme 5) using suitable conditions for benzylic oxidation. For example, a hydroxyl or oxo group can be introduced prior to cyclization, protected with a protecting group, and deprotected following the intramolecular ketone alkenylation reaction.

Scheme 6. General Synthesis of Phainanoid analogs.

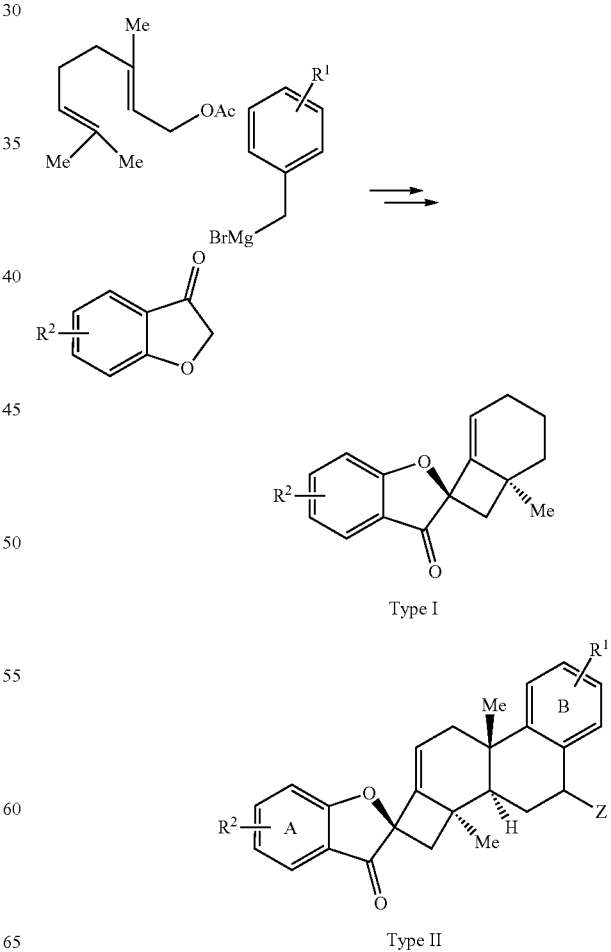

Type I

Type II

Further, additional analogs related to the Type II analogs can be prepared by substituting the benzyl magnesium bromide (BnMgBr) shown in Scheme 6 with a reagent comprising another type of aryl group. For example, the allylic coupling to geranyl acetate 17 in Scheme 4 can be performed using a reagent having the formula $ArCH_2M$, wherein Ar is substituted or unsubstituted aryl and M is Li or MgX where X is halide (i.e., wherein the $ArCH_2M$ reagent is used in place of the BnMgBr). Thus, the B ring of the Type II structure shown in Scheme 6 can also be varied, e.g., to incorporate, for example, a furan, pyrrole, benzofuran or indole moiety in place of the benzene moiety. These other types of B rings can optionally include one or more aryl group substituents (e.g., $R^1$ groups).

In some embodiments, the presently disclosed subject matter provides a method of preparing a method of preparing a phainanoid analog, the method comprising: (a) providing a compound of Formula (I) or Formula (II):

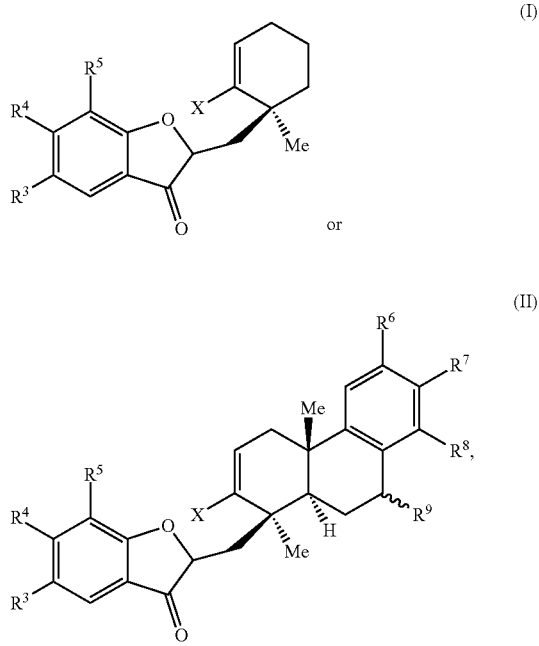

wherein:

X is a leaving group;

$R^3$, $R^4$, and $R^5$ are each independently selected H or an aryl group substituent (e.g., selected from the group comprising alkyl, substituted alkyl, aryl, substituted aryl, alkoxy, aryloxy, amino, and acetamido):

$R^6$, $R^7$, and $R^8$ are each independently selected from H and an aryl group substituent (e.g., selected from the group comprising H, alkyl, substituted alkyl, aryl, substituted aryl, alkoxy, aryloxy, amino, acetamido, and nitro); and $R^9$ is selected from the group consisting of H, hydroxyl, protected hydroxyl, and alkoxy; and (b) contacting the compound of Formula (I) or Formula (II) with a metal compound, a ligand precursor, and a non-nucleophilic base to perform an intramolecular ketone alkenylation; thereby providing a phainanoid analog having a structure of Formula (III) or Formula (IV):

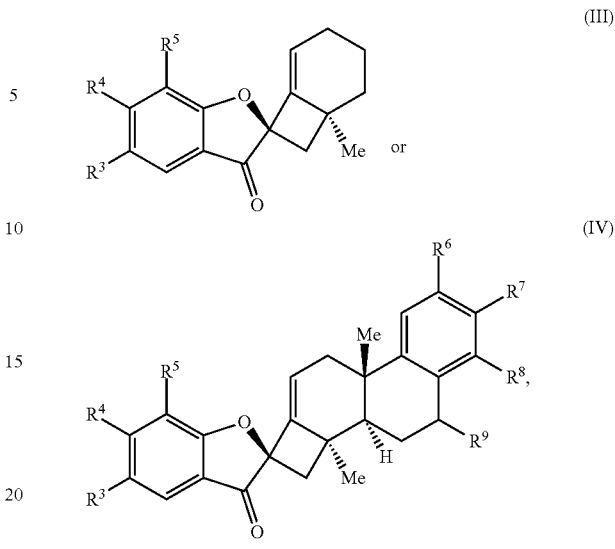

wherein $R^3$-$R^9$ are as defined for the compounds of Formulas (I) and (II).

X can be any suitable leaving group. In some embodiments, X is a halide (i.e., F, Cl, Br, or I) or an sulfonate ester such that X has the formula $-O-S(=O)_2-R$, wherein R is selected from alkyl, substituted alkyl, aryl, and substituted aryl. In some embodiments, R is a perfluoroalkyl group (e.g., $CF_3$ or $CF_2CF_2CF_3$). In some embodiments, R is $-CF_3$, $-CH_3$, $-C_6H_4CH_3$, or $C_nF_{2n+1}$, wherein n is an integer between 2 and 12. In some embodiments, n is an integer between 2 and 6 (i.e., 2, 3, 4, 5, or 6). Thus, in some embodiments, X is mesyl (-Ms), tosyl (-Ts) or triflate (—OTf). In some embodiments, X is triflate (—OTf) (i.e., having the formula $-O-S(=O)_2-CF_3$).

In some embodiments, one or more of $R^3$-$R^8$ is H. In some embodiments, $R^3$-$R^5$ are each H. In some embodiments, $R^6$-$R^8$ are each H.

The metal compound and the ligand precursor can form an active transition metal catalyst during the contacting step. The metal compound can be any suitable metal compound, e.g., any suitable transition metal compound. In some embodiments, the metal compound is a palladium (Pd), nickel (Ni), or platinum (Pt) compound. In some embodiments, the Pd, Ni, or Pt compound is selected from the group comprising a Pd(O) compound, a Pd(II) compound, a Ni(O) compound, a Ni(II) compound, a Pt(O) compound, and a Pt(II) compound. In some embodiments, the metal compound is a Pd compound or a Ni compound. In some embodiments, the metal compound is a Pd compound. In some embodiments, the Pd compound is a Pd(O) catalyst, such bis(dibenzylideneacetone) palladium ($Pd(dba)_2$). In some embodiments, the Pd compound is a Pd(II) compound. In some embodiments, the Pd(II) compound is palladium acetate ($Pd(OAc)_2$).

The metal compound can be a precatalyst compound that forms a catalyst for the alkenylation reaction when contacted by the ligand precursor during step (b). Any suitable amount of the metal compound (e.g., the Pd compound) can be used to form the catalyst for the intramolecular ketone alkenylation. In some embodiments, the contacting is performed using between about 0.5 mole percent (mol %) and about 10 mol % of the metal compound (e.g., about 0.5, 1, 1.5, 2, 2.5, 3, 3.5, 4, 4.5, 5, 5.5, 6, 6.5, 7, 7.5, 8, 8.5, 9, 9.5, or about 10 mol % of a Pd compound) as compared to an amount of the compound of Formula (I) or Formula (II). In some embodiments, the contacting is performed using between about 5 mol % and about 10 mol % of the metal compound (e.g., the Pd compound) as compared to an amount of the compound of Formula (I) or Formula (II). In some embodiments, the contacting is performed using about 5 mol % of the metal compound (e.g., the Pd compound).

The ligand precursor can comprise any suitable molecule that can bond to a metal ion in the metal compound to form a metal complex that can serve as a catalyst for the alkenylation reaction or that can provide a compound (e.g., by being deprotonated) that can bond to a metal ion in the metal compound to form a metal complex that can serve as a catalyst for the alkenylation reaction. In some embodiments, the ligand precursor is a compound that comprises one or more bulky substituent, such as a branched alkyl group, and/or one or more electron-rich substituent. In some embodiments, the ligand precursor is a phosphorous compound, such as, but not limited to a phosphine; or is an N-heterocyclic carbene (NHC) precursor. NHC precursors include, for example, imidazolium salts, such as N,N-diaryl substituted imidazolium salts wherein the N-aryl substituents can be further substituted with one or more alkyl, branched alkyl, substituted alkyl, or aralkyl groups. In some embodiments, each of the N-aryl substituents is substituted by two or three alkyl, branched alkyl, substituted alkyl, or aralkyl groups. For instance, various NHC precursors have been described in the art for use in the metal (e.g., Ni)-catalyzed intermolecular alkenylation of ketone enolates. See Grigalunas et al., J. Am. Chem. Soc. 2015, 137, 7019-7022. In some embodiments, the ligand precursor is a phosphine or a NHC precursor.

In some embodiments, the ligand precursor is a phosphine. Any suitable phosphine can be used in the contacting step (b). Generally, suitable phosphines for use in the presently disclosed subject matter include phosphines that comprise one or more bulky substituent (e.g., a tert-butyl group) and/or one or more electron-rich substituent. In some embodiments, the phosphine is a trialkylphosphine, a triarylphosphine or a dialkylarylphosphine. In some embodiments, the dialkylarylphosphine comprises a ferrocenyl group. Thus, in some embodiments, the phosphine is a dialkylferrocenyl phosphine (e.g., a dialkylferrocenyl monophosphine). In some embodiments, the dialkylarylphosphine includes a tert-butyl group. In some embodiments, the dialkylarylphosphine includes both a ferrocenyl group and a tert-butyl group. In some embodiments, the phosphine is 1,2,3,4,5-pentaphenyl-1'-(di-tert-butylphosphino)ferrocene (QPhos).

In some embodiments, the metal compound is a Pd compound and the ligand precursor is a phosphine.

Any suitable amount of the ligand precursor (e.g., the phosphine) can be used in step (b). Typically, the amount of ligand precursor (e.g., the phosphine) used is the same as or more than the amount of the metal compound (e.g., the Pd compound). In some embodiments, the amount of the ligand precursor (e.g., the phosphine) is about two times the mol % of the amount of the metal compound (e.g., the Pd compound). Thus, in some embodiments, the contacting is performed using between about 1 mol % and about 20 mol % (e.g., about 1, 2, 3, 4, 5, 6, 7, 8, 9, 10, 11, 12, 13, 14, 15, 16, 17, 18, 19, or about 20 mol %) of the ligand precursor (e.g., the phosphine) as compared to the compound of Formula (I) or Formula (II). In some embodiments, the contacting is performed using between about 10 mol % and about 20 mol % of the ligand precursor (e.g., the phosphine) as compared to the amount of the compound of Formula (I) or Formula (II). In some embodiments, the contacting is performed using about 10 mol % of the ligand precursor (e.g., the phosphine).

Any suitable non-nucleophilic base can be used. In some embodiments, the non-nucleophilic base is a non-nucleophilic base of a conjugate acid having a pKa of about 10 or greater. In some embodiments, the non-nucleophilic base is a base with a conjugate acid having a pKa of about 16 or greater. Suitable non-nucleophilic bases include, but are not limited to, lithium hexamethyldisilamide (LiHMDS), potassium hexamethyldisilamide (KHMDS), sodium hexamethyldisilamide (NaHMDS), cesium carbonate ($Cs_2CO_3$), lithium tert-butoxide (LiO$^t$Bu), potassium tert-butoxide (KO$^t$Bu), and sodium tert-butoxide (NaO$^t$Bu). In some embodiments, the base is an alkali metal tert-butoxide, such as LiO$^t$Bu, KO$^t$Bu, or NaO$^t$Bu. In some embodiments, the base is LiO$^t$Bu.

Generally the base is provided in a molar excess compared to the compound of Formula (I) or Formula (II). In some embodiments, the contacting is performed using between about 105 mol % and about 150 mol % (e.g., about 105, 110, 115, 120, 125, 130, 135, 140, 145, or about 150 mol %) of the base compared to the amount of the compound of Formula (I) or Formula (II). In some embodiments, the contacting is performed using about 150 mol % of the base compared to an amount of the compound of Formula (I) or Formula (II).

Step (b) can be performed in a suitable solvent. In some embodiments, the solvent is an aprotic solvent. Suitable aprotic solvents include for example, nonpolar aprotic solvents (i.e., aprotic organic solvents having a dielectric constant below about 5) and moderately polar aprotic solvents (e.g., aprotic organic solvents with a dielectric constant between about 5 and about 20). In some embodiments, the solvent is an aliphatic hydrocarbon solvent (e.g., pentane or hexanes), an aromatic solvent (e.g., benzene, toluene or xylene), an ether (THF or diethylether ($Et_2O$)), or a halogenated hydrocarbon (e.g., chloroform or dichloromethane).

The solvent, temperature, and reaction time used in step (b) can vary depending upon the solubility and/or reactivity of the substrate (i.e., the compound of Formula (I) or (II)). In some embodiments, the method comprises providing a compound of Formula (I) and the compound of Formula (I) is contacted with a Pd compound, a phosphine, and a non-nucleophilic base in the presence of an ether solvent, optionally wherein the ether solvent is THF. In some embodiments, the contacting is performed between about room temperature (e.g., 20° C.) and about 65° C. In some embodiments, the contacting is performed at about room temperature.

In some embodiments, the method comprises providing a compound of Formula (II), and the compound of Formula (II) is contacted with a Pd compound, a phosphine, and a non-nucleophilic base in the presence of an aromatic solvent. In some embodiments, the aromatic solvent is toluene. In some embodiments, the contacting is performed at between about room temperature and about 100° C. In some embodiments, the contacting is performed at a temperature between about 40 C and about 80° C. In some embodiments, the contacting is performed at about 60° C.

In some embodiments, the contacting is performed for between about 12 hours and about 80 hours (e.g., about 12, 16, 20, 24, 28, 32, 26, 40, 44, 48, 52, 56, 60, 64, 68, 72, 76, or about 80 hours). In some embodiments, the contacting is performed for between about 24 hours and about 60 hours. In some embodiments, the contacting is performed for between about 24 hours and about 48 hours.

In some embodiments, the contacting is performed where the compound of Formula (I) or Formula (II) is provided at a concentration of between about 0.05 molar (M) and about 0.1 M in a suitable solvent. In some embodiments, the compound of Formula (I) or Formula (II) is provided at a concentration of about 0.05 M.

In some embodiments, the contacting provides a compound of Formula (III) or Formula (IV in a yield of about 50% or more. In some embodiments, the yield is about 65% or more. In some embodiments, the yield is about 75% or more. In some embodiments, the yield is about 83%. In some embodiments, the contacting provides the compound of Formula (III) or Formula (IV in a diastereomeric ratio of at least about 2:1 (e.g., about 4:1, 8:1, 10:1, 12:1, 20:1, 30:1, 40:1 or 50:1) or greater. In some embodiments, the compound of Formula (III) or Formula (IV) is provided in a yield of about 65% or more and/or in a diastereomeric ratio of about 20:1 or greater.

In some embodiments, $R^9$ is H. In some embodiments, $R^9$ is hydroxyl and the method further comprises oxidizing the hydroxyl group to form a ketone. For example, the oxidation can be performed using manganese dioxide ($MnO_2$), pyridinium chlorochromate (PCC), Dess-Martin periodinane (DMP) (i.e., 1,1,1-triacetoxy-1,1-dihydro-1,2-benziodoxol-3(1H)-one), or using Swern oxidation conditions (e.g., oxalyl chloride, dimethylsulfoxide (DMSO) and a base, such as triethylamine). In some embodiments, $R^9$ is a protected hydroxyl and the method further comprises deprotecting the hydroxyl group. In some embodiments, the method comprises deprotecting the hydroxyl group and oxidizing the hydroxyl group to form a ketone.

In some embodiments, the compound of Formula (III) or (IV) is selected from the group comprising:

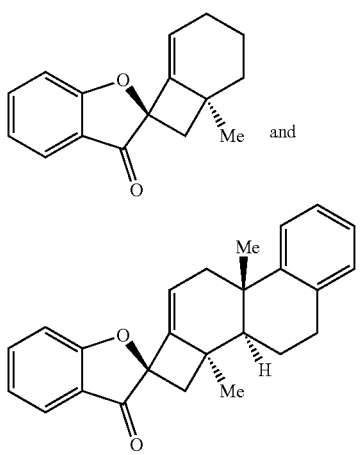

and

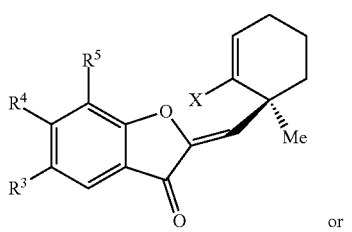

.

In some embodiments, the compound of Formula (I) or Formula (II) is provided via the selective reduction of a compound of Formula (VII) or Formula (VIII):

(VII)

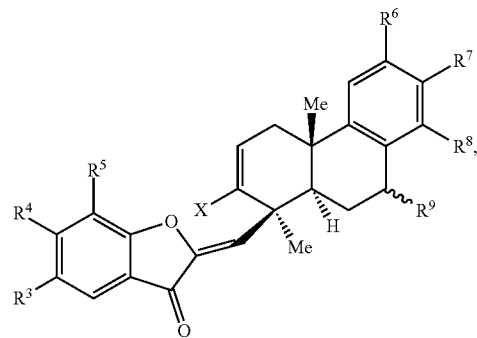

or (VIII)

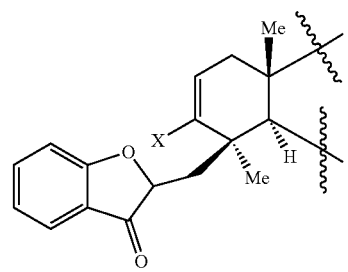

wherein $R^3$-$R^9$ and X are as defined for the compound of Formulas (I) and (II). In some embodiments, the selective reduction comprises contacting the compound of Formula (VII) or Formula (VIII) with a palladium on carbon catalyst (Pd/C) in the presence of hydrogen gas ($H_2$). The selective reduction can be performed in any suitable solvent, such as, but not limited to, toluene (PhMe), ethyl acetate (EA), dichloromethane (DCM), diethyl ether ($Et_2O$), tetrahydrofuran (THF), methanol (MeOH) or mixtures thereof. In some embodiments, the selective reduction is performed in a mixture comprising EA, $Et_2O$, THF, or PhMe as the major solvent (e.g., greater than about 75% by volume of the solvent mixture) and DCM. In some embodiments, the reduction is performed in a mixture of PhMe and DCM. In some embodiments, the mixture of PhMe and DCM comprises at least about 90% PhMe (e.g., about 90%, 92%, 94%, 95%, 96%, 97%, 98%, or about 99% PhMe). In some embodiments, the reduction is performed in a mixture comprising PhMe and DCM in a ratio of about 20:1 or about 50:1 (by volume).

In some embodiments, the presently disclosed subject matter provides a method of preparing a phainanoid (i.e., a synthetically prepared version of one of the natural product phainanoids, e.g., one of compounds 1-6) or a synthetic intermediate thereof, wherein the method comprises performing an intramolecular ketone alkenylation (e.g., a palladium-catalyzed intramolecular ketone alkenylation). In some embodiments, the method comprises (a) providing a compound comprising a moiety having the structure:

wherein X is a leaving group; and (b) contacting the compound provided in step (a) with a metal compound, a ligand precursor, and a non-nucleophilic base to perform an intramolecular ketone alkenylation; thereby providing a phainanoid or a synthetic intermediate thereof.

X can be any suitable leaving group. In some embodiments, X is a halide (i.e., F, Cl, Br, or I) or an sulfonate ester such that X has the formula —O—S(=O)$_2$—R, wherein R is selected from alkyl, substituted alkyl, aryl, and substituted aryl. In some embodiments, R is a perfluoroalkyl group (e.g., CF$_3$ or CF$_2$CF$_2$CF$_3$). In some embodiments, R is —CF$_3$, —CH$_3$, —C$_6$H$_4$CH$_3$, or C$_n$F$_{2n+1}$, wherein n is an integer between 2 and 12. In some embodiments, n is an integer between 2 and 6. Thus, in some embodiments, X is mesyl (-Ms), tosyl (-Ts) or triflate (—OTf). In some embodiments, X is —O—S(=O)$_2$—CF$_3$ (—OTf).

Any suitable transition metal compound can be used as the metal compound. In some embodiments, the metal compound is a Pd, Ni, or Pt compound. In some embodiments, the Pd, Ni, or Pt compound is selected from the group comprising a Pd(O) compound, a Pd(II) compound, a Ni(O) compound, a Ni(II) compound, a Pt(O) compound, and a Pt(II) compound. In some embodiments, the metal compound is a Pd compound or a Ni compound. In some embodiments, the metal compound is a Pd compound. Any suitable Pd compound can be used. In some embodiments, the Pd compound is a Pd(O) catalyst, such bis(dibenzylideneacetone) palladium (Pd(dba)$_2$). In some embodiments, the Pd compound is a Pd(II) compound. In some embodiments, the Pd(II) compound is palladium acetate (Pd(OAc)$_2$).

Any suitable amount of the metal compound (e.g., the Pd compound) can be used. In some embodiments, the contacting is performed using between about 0.5 mole percent (mol %) and about 10 mol % of the metal (e.g, Pd) compound (e.g., about 0.5, 1, 1.5, 2, 2.5, 3, 3.5, 4, 4.5, 5, 5.5, 6, 6.5, 7, 7.5, 8, 8.5, 9, 9.5, or about 10 mol % of the metal (e.g., Pd) compound) as compared to an amount of the compound provided in step (a). In some embodiments, the contacting is performed using between about 5 mol % and about 10 mol % of the metal (e.g., Pd) compound as compared to an amount of the compound of provided in step (a). In some embodiments, the contacting is performed using about 5 mol % of the metal (e.g., Pd) compound.

The ligand precursor can comprise any suitable ligand precursor that can be or that can provide a ligand for a metal ion in the metal compound. In some embodiments, the ligand precursor is a compound that comprises one or more bulky substituent, such as a branched alkyl group, and/or one or more electron-rich substituent. In some embodiments, the ligand precursor is a phosphorous compound, such as, but not limited to a phosphine; or is an N-heterocyclic carbene (NHC) precursor, e.g., a imidazolium salt, such as a N,N-diaryl substituted imidazolium salt wherein the N-aryl substituents can be further substituted with alkyl, branched alkyl, substituted alkyl, or aralkyl groups. In some embodiments, the ligand precursor is a phosphine or a NHC precursor.

In some embodiments, the ligand precursor is a phosphine. Any suitable phosphine can be used in the contacting step (b). Generally, suitable phosphines for use in the presently disclosed subject matter include phosphines that comprise one or more bulky substituent (e.g., a branched alkyl group such as a tert-butyl group) and/or one or more electron-rich substituent. In some embodiments, the phosphine is a trialkylphosphine, a triarylphosphine or a dialkylarylphosphine. In some embodiments, the dialkylarylphosphine comprises a ferrocenyl group. Thus, in some embodiments, the phosphine is a dialkylferrocenyl phosphine (e.g., a dialkylferrocenyl monophosphine). In some embodiments, the dialkylarylphosphine includes a tert-butyl group. In some embodiments, the dialkylarylphosphine includes both a ferrocenyl group and a tert-butyl group. In some embodiments, the phosphine is 1,2,3,4,5-pentaphenyl-1'-(di-tert-butylphosphino)ferrocene (QPhos).

In some embodiments, the metal compound is a Pd compound and the ligand precursor is a phosphine.

Any suitable amount of the ligand precursor (e.g., the phosphine) can be used in step (b). Typically, the amount of ligand precursor (e.g., the phosphine) used is the same as or more than the amount of the metal compound (e.g., the Pd compound). In some embodiments, the amount of ligand precursor (e.g., phosphine) used is about two times the mol % of the amount of the Pd compound. Thus, in some embodiments, the contacting is performed using between about 1 mol % and about 20 mol % (e.g., about 1, 2, 3, 4, 5, 6, 7, 8, 9, 10, 11, 12, 13, 14, 15, 16, 17, 18, 19, or about 20 mol %) of the ligand precursor (e.g., the phosphine) as compared to the compound provided in step (a). In some embodiments, the contacting is performed using between about 10 mol % and about 20 mol % of the ligand precursor (e.g., the phosphine) as compared to the amount of the compound provided in step (a). In some embodiments, the contacting is performed using about 10 mol % of the ligand precursor (e.g., the phosphine).

Any suitable non-nucleophilic base can be used. In some embodiments, the non-nucleophilic base is a non-nucleophilic base of a conjugate acid having a pKa of about 10 or greater. In some embodiments, the non-nucleophilic base is a base with a conjugate acid having a pKa of about 16 or greater. Suitable non-nucleophilic bases include, but are not limited to, lithium hexamethyldisilamide (LiHMDS), potassium hexamethyldisilamide (KHMDS), sodium hexamethyldisilamide (NaHMDS), cesium carbonate (Cs$_2$CO$_3$), lithium tert-butoxide (LiO$^t$Bu), potassium tert-butoxide (KO$^t$Bu), and sodium tert-butoxide (NaO$^t$Bu). In some embodiments, the base is an alkali metal tert-butoxide, such as LiO$^t$Bu, KO$^t$Bu, or NaO$^t$Bu. In some embodiments, the base is LiO$^t$Bu.

Generally the base is provided in a molar excess compared to the compound provided in step (a). In some embodiments, the contacting is performed using between about 105 mol % and about 150 mol % (e.g., about 105, 110, 115, 120, 125, 130, 135, 140, 145, or about 150 mol %) of the base compared to the amount of the compound provided in step (a). In some embodiments, the contacting is performed using about 150 mol % of the base compared to an amount of the compound provided in step (a).

Step (b) can be performed in a suitable solvent. In some embodiments, the solvent is an aprotic solvent. Suitable aprotic solvents include for example, nonpolar aprotic solvents (i.e., aprotic organic solvents having a dielectric constant below about 5) and moderately polar aprotic solvents (e.g., aprotic organic solvents with a dielectric constant between about 5 and about 20). In some embodiments, the solvent is an aliphatic hydrocarbon solvent (e.g., pentane or hexanes), an aromatic solvent (e.g., benzene, toluene or xylene), an ether (THF or diethylether), or a halogenated hydrocarbon (e.g., chloroform or dichloromethane). The solvent, temperature, and reaction time used in step (b) can vary depending upon the solubility and/or reactivity of the substrate (i.e., the compound provided in step (a). In some embodiments, the contacting is performed between about room temperature (e.g., 20° C.) and about 100° C. In some embodiments, the contacting is performed for between about 12 hours and about 80 hours (e.g., about 12, 16, 20, 24, 28, 32, 26, 40, 44, 48, 52, 56, 60, 64, 68, 72, 76, or about 80 hours). In some embodiments, step (b) is performed with the substrate (i.e., the compound provided in step (a)) present at a concentration of about 0.05 M to about 0.1 M in a suitable solvent. In some embodiments, the compound of step (a) is provided via the selective reduction of a corresponding α,β-unsaturated ketone performed using Pd/C and hydrogen gas.

In some embodiments, the method further comprises one or more additional steps, e.g., deprotecting steps and/or oxidation steps, to transform a phainanoid synthetic intermediate produced in step (b) into a phainanoid compound.

III. Phainanoid Analogs and Synthetic Intermediates Thereof

In some embodiments, the presently disclosed subject matter provides phainanoid analogs, as well as compounds that can be used as synthetic intermediates in preparing phainanoids and phainanoid analogs. In particular, the presently disclosed phainanoid analogs include the benzofuran-based 4,5-spirocycle with the strained exocyclic olefin motif present in the "western" part of the natural product phainanoids. Given the inclusion of this motif, it is believed that the presently disclosed phainanoid analogs can be useful as novel immunosuppressive agents, e.g., for the treatment of diseases characterized by an aberrant immune response, such as autoimmune and/or inflammatory diseases, as well as during transplant operations. In preliminary biological testing, phainanoid analog compounds 7 and 8, along with intermediate compound 25 showed immunosuppressive activity (i.e., suppression of interleukin-2 (IL-2) production) in a B cell lymphoma cell line. For all three compounds, complete suppression of IL-2 was observed using 100 micromolar (μM) concentrations of the compounds.

In some embodiments, the presently disclosed subject matter provides a compound of Formula (V'):

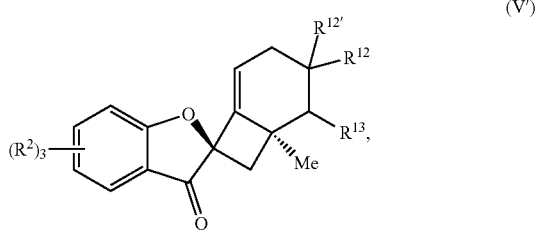

(V')

wherein: each $R^2$ is independently selected from the group comprising H, alkyl, substituted alkyl, aryl, substituted aryl, alkoxy, aryloxy, amino, and acetamido; $R^{12'}$ is selected from the group comprising H and alkyl; $R^{12}$ is selected from the group comprising alkyl, substituted alkyl, aralkyl, substituted aralkyl, and $R^{13}$ is alkyl or substituted alkyl; or where $R^{12}$ and $R^{13}$ together form an optionally substituted mono- or polycyclic structure; subject to the proviso that the compound of Formula (V') is other than a natural product phainanoid compound (e.g. other than one of compounds 1-6 of Scheme 1).

In some embodiments, the presently disclosed subject matter provides a compound of one of Formulas (V) or (VI):

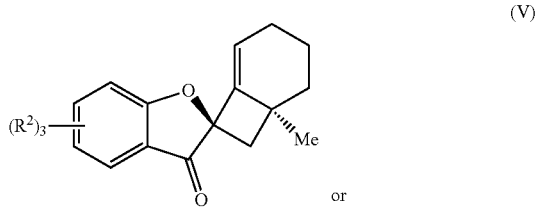

(V)

or

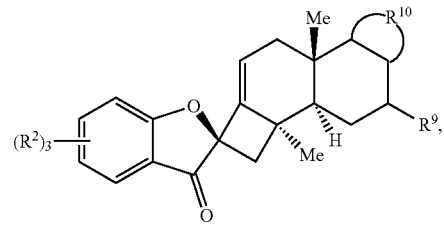

(VI)

wherein: each $R^2$ is independently selected from the group comprising H, alkyl, substituted alkyl, aryl, substituted aryl, alkoxy, aryloxy, amino, and acetamido; $R^9$ is selected from the group comprising H, =O, hydroxyl, protected hydroxyl, and alkoxy; and $R^{10}$ forms a substituted or unsubstituted monocyclic or bicyclic aromatic ring structure. In some embodiments, the monocyclic or bicyclic aromatic ring structure is selected from benzene, indole, furan, pyrrole, and benzofuran, which can optionally be substituted by one or more aryl group substituents.

In some embodiments, $R^{10}$ forms a substituted or unsubstituted benzene ring structure, and the compound of Formula (VI) is a compound of Formula (VIa):

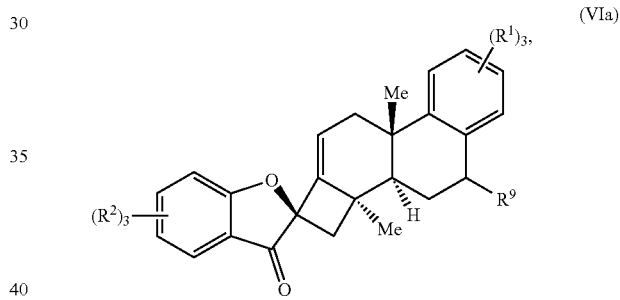

(VIa)

wherein each $R^1$ is independently selected from the group comprising H, alkyl, substituted alkyl, aryl, substituted aryl, alkoxy, aryloxy, amino, acetamido, and nitro; each $R^2$ is independently selected from the group comprising H, alkyl, substituted alkyl, aryl, substituted aryl, alkoxy, aryloxy, amino, and acetamido; and $R^9$ is selected from the group comprising H, =O, hydroxyl, protected hydroxyl, and alkoxy.

In some embodiments, the compound of Formula (V) or Formula (VI) is a compound of Formula (III) or Formula (IV):

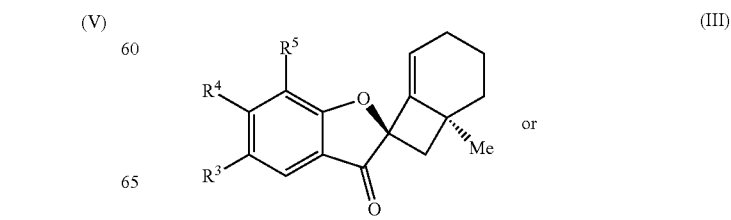

(III)

or

-continued

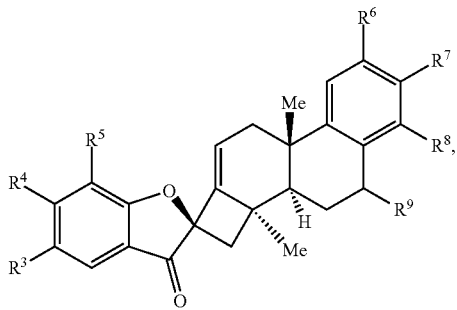

(IV)

wherein: $R^3$, $R^4$, and $R^5$ are each independently selected from the group comprising H, alkyl, substituted alkyl, aryl, substituted aryl, alkoxy, aryloxy, amino, and acetamido; $R^6$, $R^7$, and $R^8$ are each independently selected from the group comprising H, alkyl, substituted alkyl, aryl, substituted aryl, alkoxy, aryloxy, amino, acetamido, and nitro; and $R^9$ is selected from the group comprising H, =O, hydroxyl, protected hydroxyl, and alkoxy.

In some embodiments, $R^9$ is oxo (i.e., =O). Thus, in some embodiments, the compound of Formula (IV) is a compound of Formula (IVb):

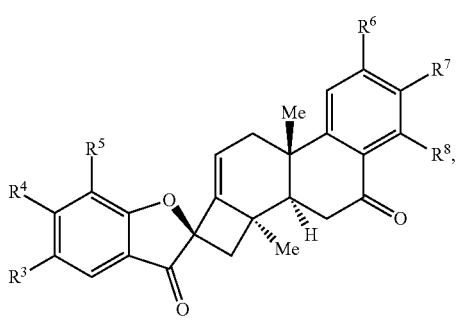

(IVb)

wherein $R^3$, $R^4$, and $R^5$ are each independently selected from the group comprising H, alkyl, substituted alkyl, aryl, substituted aryl, alkoxy, aryloxy, amino, and acetamido; and $R^6$, $R^7$, and $R^8$ are each independently selected from the group comprising H, alkyl, substituted alkyl, aryl, substituted aryl, alkoxy, aryloxy, amino, acetamido, and nitro. In some embodiments, each of $R^3$-$R^8$ is H.

In some embodiments, $R^9$ is selected from H, hydroxyl, protected hydroxyl, and alkoxy, and the compound of Formula (IV) is a compound of Formula (IVa):

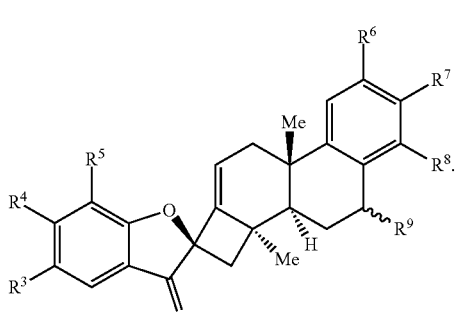

(IVa)

In some embodiments, $R^9$ is H. In some embodiments, one or more of $R^3$, $R^4$, and $R^5$ are H. In some embodiments, one or more of $R^6$, $R^7$, and $R^8$ are H. In some embodiments, $R^3$, $R^4$, and $R^5$ are each H. In some embodiments, $R^6$, $R^7$, and $R^8$ are each H.

In some embodiments, the compound is selected from the group comprising:

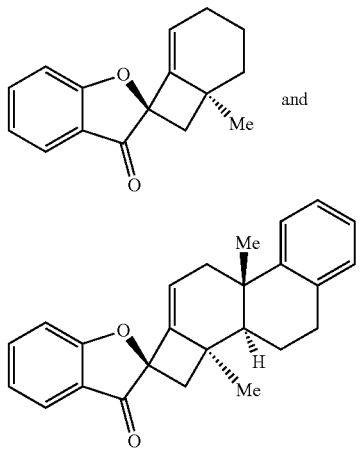

In some embodiments, the presently disclosed subject matter provides a pharmaceutical composition comprising a phainanoid analog as described herein. In some embodiments, the phainanoid analog is a compound of Formula (V), (VI), or (VIa). In some embodiments, the phainanoid analog is a compound of Formula (III) or (IV). In some embodiments, the phainanoid analog is a compound of Formula (IVa) or (IVb). In some embodiments, the pharmaceutical composition comprises compound 7 or compound 8.

Any suitable pharmaceutical formulation can be used to prepare the pharmaceutical compositions. In some embodiments, the pharmaceutical composition further comprises a pharmaceutically acceptable carrier and optionally one or more additional agents typically used in pharmaceutical formulations. In some embodiments, the pharmaceutically acceptable carrier can be pharmaceutically acceptable in humans.

For example, suitable pharmaceutical compositions can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS). It should be understood that in addition to the ingredients particularly mentioned above, the formulations of this presently disclosed subject matter can include other agents conventional in the art. For example, sterile pyrogen-free aqueous and non-aqueous solutions can be used.

In some embodiments, the presently disclosed subject matter provides a synthetic intermediate of a phainanoid analog. These compounds can also find use as potential immunosuppressive agents. In some embodiments, the synthetic intermediate is a compound of one of Formulas (I'), (II') or (II''):

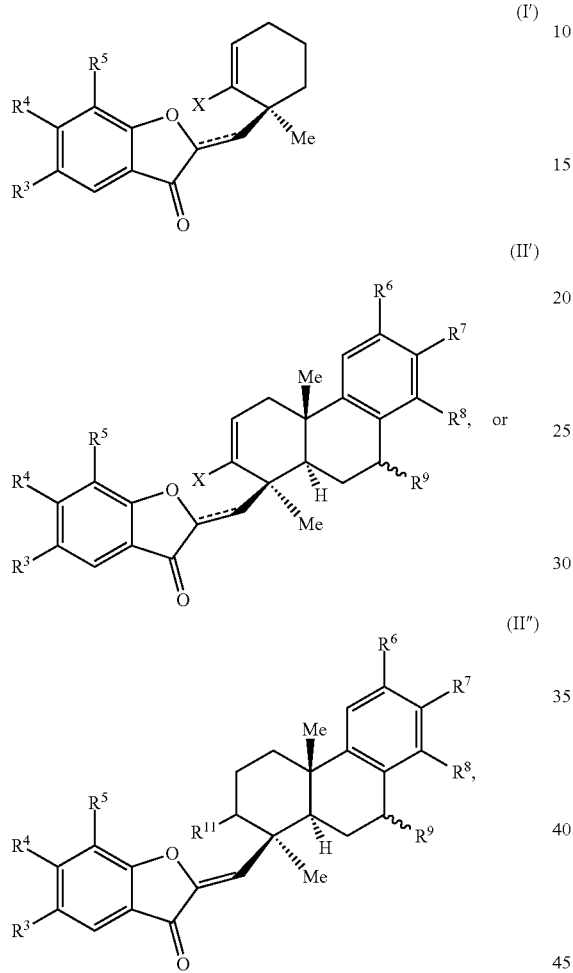

wherein:
≡≡≡≡ is a double or single bond;
X is selected from the group comprising a halide and —O—S(=O)$_2$—R, wherein R is selected from the group comprising alkyl, substituted alkyl, aryl, and substituted aryl, optionally wherein R is —CF$_3$, —CH$_3$, —C$_6$H$_4$CH$_3$, or —C$_n$F$_{2n+1}$ wherein n is an integer between 2 and 12, optionally wherein n is an integer between 2 and 6;
$R^3$, $R^4$, and $R^5$ are each independently selected from the group comprising H, alkyl, substituted alkyl, aryl, substituted aryl, alkoxy, aryloxy, amino, and acetamido;
$R^6$, $R^7$, and $R^8$ are each independently selected from the group comprising H, alkyl, substituted alkyl, aryl, substituted aryl, alkoxy, aryloxy, amino, acetamido, and nitro;
$R^9$ is selected from the group comprising H, hydroxyl, protected hydroxyl, and alkoxy; and
$R^{11}$ is selected from the group comprising =O, hydroxyl, and protected hydroxyl.

In some embodiments, X is -Ms, -Ts or —OTf. In some embodiments, X is —O—S(=O)$_2$—CF$_3$ (—OTf). In some embodiments, one or more of $R^3$, $R^4$, and $R^5$ are H. In some embodiments, $R^3$, $R^4$, and $R^5$ are each H. In some embodiments, one or more of $R^6$, $R^7$, and $R^8$ are H. In some embodiments, $R^6$, $R^7$, and $R^8$ are each H. In some embodiments, $R^9$ is H. In some embodiments, $R^{11}$ is =O. In some embodiments, $R^{11}$ is hydroxyl.

In some embodiments, the compound is selected from the group comprising:

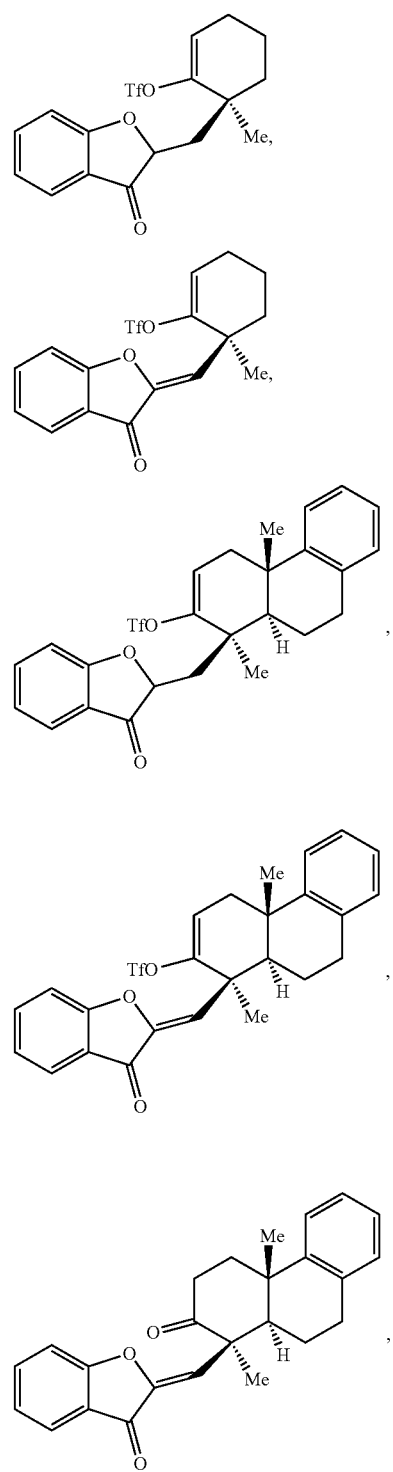

-continued

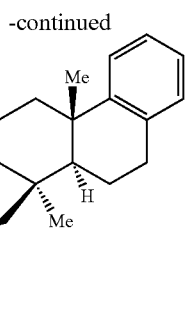

In some embodiments, the presently disclosed subject matter provides a synthetic intermediate of a phainanoid compound. In some embodiments, the presently disclosed subject matter provides a compound of Formula (IX):

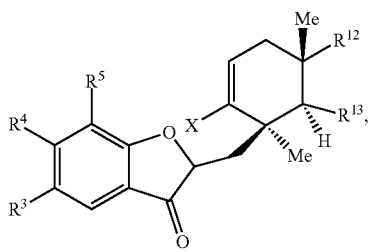

wherein:

X is selected from the group comprising a halide and —O—S(=O)$_2$—R, wherein R is selected from the group comprising alkyl, substituted alkyl, aryl, and substituted aryl, optionally wherein R is —CF$_3$, —CH$_3$, —C$_6$H$_4$CH$_3$, or —C$_n$F$_{2n+1}$, wherein n is an integer between 2 and 12, optionally wherein n is an integer between 2 and 6;

$R^3$, $R^4$, and $R^5$ are each independently selected from the group comprising H, alkyl, substituted alkyl, aryl, substituted aryl, alkoxy, aryloxy, amino, and acetamido;

$R^6$, $R^7$, and $R^8$ are each independently selected from the group comprising H, alkyl, substituted alkyl, aryl, substituted aryl, alkoxy, aryloxy, amino, acetamido, and nitro;

$R^{12}$ is selected from the group comprising alkyl, substituted alkyl, aralkyl, and substituted aralkyl, and $R^{13}$ is alkyl or substituted alkyl; or where $R^{12}$ and $R^{13}$ together form an optionally substituted mono- or polycyclic structure.

In some embodiments, $R^{12}$ and $R^{13}$ together form a cyclohexane or cyclohexanone ring structure. In some embodiments, the cyclohexane or cyclohexanone ring structure is fused to another ring structure, which can be substituted or unsubstituted.

IV. Methods of Treatment

In some embodiments, the presently disclosed subject matter provides a method of treating a disease characterized by an aberrant immune response in a subject in need of treatment thereof, wherein the method comprises administering a pharmaceutical composition as described herein (e.g., comprising a compound of one of Formula (V), (VI), (VIa), (III), (IV), (IVa), or (IVb)). In some embodiments, the disease characterized by an aberrant immune response is an autoimmune disorder or an inflammatory disease. In some embodiments, the subject is a subject undergoing a trans- plant operation. In some embodiments, the compositions can also be administered to in vitro samples (e.g., isolated cells or tissues), e.g., for research purposes or to assay the activity level of a particular compound described herein.

In some embodiments, the disease characterized by an aberrant immune response is an autoimmune and/or inflammatory disease selected from the group including, but not limited to, osteoarthritis, chronic obstructive pulmonary disease (COPD), atherosclerosis, hypertension, allograft rejection, pelvic inflammatory disease, ulcerative colitis, Crohn's disease, allergic inflammation in the lung, cachexia, stroke, congestive heart failure, pulmonary fibrosis, hepatitis, glioblastoma, Guillain-Barre Syndrome, systemic lupus, erythematosus viral myocarditis, post-transplantation organ protection, acute pancreatitis, irritable bowel disease (IBD), general inflammation, autoinflammatory disease, arterial stenosis, organ transplant rejection, burns, chronic lung injury and respiratory distress, insulin-dependent diabetes, non-insulin dependent diabetes, hypertension, obesity, arthritis, neurodegenerative disorders, lupus, Lyme's disease, gout, sepsis, hyperthermia, ulcers, enterocolitis, osteoporosis, viral or bacterial infections, cytomegalovirus, periodontal disease, glomerulonephritis, sarcoidosis, lung disease, lung inflammation, fibrosis of the lung, asthma, acquired respiratory distress syndrome, tobacco induced lung disease, granuloma formation, fibrosis of the liver, graft vs. host disease, postsurgical inflammation, coronary and peripheral vessel restenosis following angioplasty, stent placement or bypass graft, coronary artery bypass graft (CABG), acute and chronic leukemia, B lymphocyte leukemia, neoplastic diseases, arteriosclerosis, atherosclerosis, myocardial inflammation, psoriasis, immunodeficiency, disseminated intravascular coagulation, systemic sclerosis, amyotrophic lateral sclerosis, multiple sclerosis, Parkinson's disease, Alzheimer's disease, encephalomyelitis, edema, inflammatory bowel disease, hyper IgE syndrome, cancer metastasis or growth, adoptive immune therapy, reperfusion syndrome, radiation burns, alopecia areata, ischemia, myocardial infarction, arterial stenosis, rheumatoid arthritis, coronary restenosis, neurocognitive decline, and insulin resistance.

In some embodiments, the subject is a human subject, although it is to be understood that the principles of the presently disclosed subject matter indicate that the presently disclosed subject matter can be effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

Generally, an effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject (e.g., can be varied depending upon the species, gender, age, weight, and/or physical condition of the subject) and/or to treat a particular disease. The selected dosage level can also depend upon the activity of the composition and the route of administration.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods and Materials

Unless otherwise noted, all solvents were dried by filtration through a Pure-Solv MD-5 Solvent Purification System (Inert Corporation, Amesbury, Mass., United States of America). Reaction temperatures were reported as the temperatures of the bath surrounding the flasks or vials. Analytical thin-layer chromatography (TLC) was carried out using 0.2 mm commercial silica gel plates (silica gel 60, F254, EMD Chemical Inc., Gibbstown, N.J., United States of America). Vials (15×45 mm 1 dram (4 mL)/17×60 mm 3 dram (7.5 mL) with PTFE lined cap attached) were purchased from Qorpak (Bridgeville, Pa., United States of America). Mass spectra were recorded on an Agilent 6530 liquid chromatography (LC) quad-time of flight (Q-TOF) mass spectrometer (Agilent Technologies, Santa Clara, Calif., United States of America) using electrospray ionization with fragmentation voltage set at 100 V and processed with an Agilent MassHunter Operating System (Agilent Technologies, Santa Clara, Calif., United States of America). X-ray diffraction data were collected at 100(2) K on a Bruker-Nonius Kappa CCD diffractometer (Bruker Corporation, Billerica, Mass., United States of America) or Agilent SuperNova AtlasS2 CCD diffractometer (Agilent Technologies, Santa Clara, Calif., United States of America). Infrared spectra were recorded on a NICOLET™ 380 Fourier-transform infrared (FTIR) spectrometer (Thermo Fischer Scientific, Inc., Waltham, Mass., United States of America) using neat thin film technique. Nuclear magnetic resonance (NMR) spectra ($^1$H NMR and $^{13}$C NMR) were recorded with a Bruker Model DMX 500 spectrometer (500 MHz, $^1$H at 500 MHz, $^{13}$C at 126 MHz; Bruker Corporation, Billerica, Mass., United States of America). Chemical shifts were reported in parts per million (ppm, δ) and were referenced to residual solvent (CDCl$_3$, δ=7.26 ppm ($^1$H) and 77.00 ppm ($^{13}$C)). Coupling constants were reported in Hertz (Hz). Data for $^1$H NMR spectra were reported as follows: chemical shift (ppm, referenced to protium, s=singlet, d=doublet, t=triplet, q=quartet, quin=quintet, dd=doublet of doublets, td=triplet of doublets, dq=doublet of quartets, ddd=doublet of doublet of doublets, m=multiplet, coupling constant (Hz), and integration). All other materials were obtained from Aldrich Chemical Company (Milwaukee, Wis., United States of America), Fisher Scientific (Thermo Fischer Scientific, Inc., Waltham, Mass., United States of America) or Combi-Blocks (Combi-Blocks, Inc., San Diego, Calif., United States of America) and were used as received.

Density functional theory (DFT) calculations were performed with Gaussian 09 (Gaussian, Inc., Wallingford, Conn., United States of America). Geometry optimizations were performed in the gas phase with the B3YLP functional and a mixed basis set of Lanl2dz for Pd/Fe and 6-31(d) for other atoms. Single point energies were calculated with the M06 functional developed by Truhlar and coworkers (see Zhao and Truhlar, Theor. Chem. Acc. 2008, 120, 215; and Zhao and Truhlar, Acc. Chem. Res. 2008, 41, 157) and a mixed basis set of SDD for Pd/Fe and 6-311+Gd(d,p) for other atoms. Solvation energy corrections were calculated using the SMD model (see Marenich et al., J. Phys. Chem. B 2009, 113, 6378) with THF as the solvent.

Example 2

Preparation of Compound 7

Compound 7 was prepared by the metal-catalyzed intramolecular ketone alkenylation of compound 15, which was prepared as described hereinabove in Scheme 2. Further details of the synthesis of compound 7 and its synthetic intermediates are as follows:

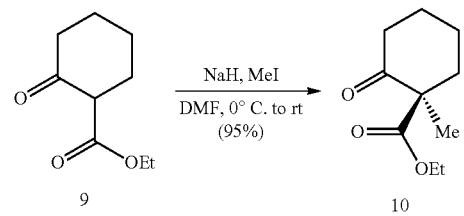 [SMILES: CCOC(=O)C1CCCCC1=O ; CCOC(=O)[C@]1(C)CCCCC1=O]

Ester 10: The title compound was prepared using the conditions reported by Hayashi and co-workers. See Hayashi et al., Tett. Lett. 2005, 46, 681. To a suspension of NaH (440 mg, 60% dispersion in mineral oil, 11 mmol) in DMF (20 mL) was added 9 (1.6 mL, 10 mmol) dropwise. The reaction mixture was stirred at 0° C. until a light yellow solution was obtained without any H$_2$ evolution. MeI (0.75 mL, 12 mmol) was then added at the same temperature dropwise. The reaction mixture was allowed to warm up to ambient temperature and keep stirring for 1 hour, after which it was quenched with saturated NH$_4$Cl solution and extracted with ether (20 mL×3). The combined extracts were dried over Na$_2$SO$_4$, filtered and concentrated in vacuo. Purification by flash chromatography (silica gel, hexanes/ethyl acetate=10:1) gave 10 as a colorless oil (1.75 g, 95% yield). The experimental NMR data of 10 recorded were consistent with those reported by Shneider and co-workers. See Shneider et al., Org. Lett. 2015, 17, 282.

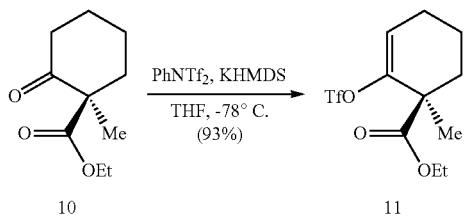 [SMILES: CCOC(=O)[C@]1(C)CCCCC1=O ; CCOC(=O)[C@]1(C)CCCC=C1OS(=O)(=O)C(F)(F)F]

Ester 11: To a flame-dried round bottle flask was charged with KHMDS (2.83 g, 14.2 mmol) and THF (20 mL). The clear solution was cooled down to −78° C., after which a solution of 10 (1.75 g, 9.5 mmol) in THF (10 mL) was added dropwise. The reaction mixture was stirred for 40 minutes, and then solid PhNTf$_2$ (4.07 g, 11.4 mmol) was added to the solution in one portion. The reaction mixture was stirred for another 60 minutes, then quenched with saturated NH$_4$Cl solution and extracted with ethyl acetate (20 mL×3). The combined extracts were dried over Na$_2$SO$_4$, filtered and concentrated in vacuo. Purification by flash chromatography (silica gel, hexanes/ethyl acetate=80:1) gave 11 as a pale yellow oil (2.81 g, 93% yield): R$_f$=0.6 (hexanes/ethyl acetate 4:1); $^1$H-NMR (500 MHz, CDCl$_3$) δ 5.85 (t, J=4.1 Hz, 1H), 4.19 (q, J=7.1 Hz, 2H), 2.31-2.18 (m, 3H), 1.70-1.60 (m, 3H), 1.42 (s, 3H), 1.28 (t, J=7.1 Hz, 3H) ppm; $^{13}$C-NMR (126 MHz, CDCl$_3$) δ 173.4, 149.5, 118.8, 118.3 (q, J=319.2 Hz), 61.5, 46.7, 35.9, 24.4, 22.0, 18.5, 13.9 ppm; IR (neat) v 2987, 2945, 1735, 1415, 1210, 1143, 1027, 901, 606 cm$^{-1}$; HRMS (ESI-TOF) m/z calcd for C$_{11}$H$_{15}$F$_3$NaO$_5$S$^+$ [M+Na]$^+$ 339.0484, found 339.0484.

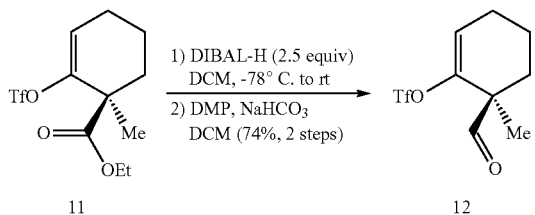 [SMILES: CCOC(=O)[C@]1(C)CCCC=C1OS(=O)(=O)C(F)(F)F ; C[C@@]1(C=O)CCCC=C1OS(=O)(=O)C(F)(F)F]

Aldehyde 12: To a solution of 11 (2.53 g, 8.00 mmol) in DCM (10 mL) at −78° C. was added DIBAL-H (1.0 M solution in hexane, 20 mL, 20 mmol) dropwise. Upon finishing addition, the reaction mixture was slowly warmed up to ambient temperature and stirred for another 2 hours, then quenched with saturated Rochelle salt solution and extracted with DCM (30 mL×3). Combined extracts were dried over Na$_2$SO$_4$, filtered and concentrated in vacuo. The crude alcohol was then dissolved in DCM (25 mL), followed by sequential addition of NaHCO$_3$ (6.72 g, 80 mmol) and Dess-Martin periodinane (3.39 g, 8.00 mmol) at ambient temperature. After 10 minutes, the reaction mixture was quenched by addition of saturated Na$_2$S$_2$O$_3$ solution, and extracted with DCM (30 mL×3). The combined extracts were dried over Na$_2$SO$_4$, filtered and concentrated in vacuo. Purification by flash chromatography (silica gel, hexanes/ethyl acetate=20:1) gave 12 as a colorless oil (1.62 g, 74% yield over 2 steps): R$_f$=0.4 (hexanes/ethyl acetate 4:1); $^1$H-NMR (500 MHz, CDCl$_3$) δ 9.49 (s, 1H), 6.06 (t, J=4.2 Hz, 1H), 2.28 (q, J=5.8 Hz, 2H), 2.10-2.04 (m, 1H), 1.72-1.55 (m, 3H), 1.33 (s, 3H) ppm; $^{13}$C-NMR (126 MHz, CDCl$_3$) δ 199.3, 148.0, 121.3, 118.3 (q, J=319.6 Hz), 50.7, 32.3, 24.4, 18.5, 18.0 ppm; IR (neat) v 2945, 1734, 1415, 1212, 1142, 1036, 873, 614 cm$^{-1}$; HRMS (ESI-TOF) m/z calcd for C$_9$H$_{11}$F$_3$NaO$_4$S$^+$ [M+Na]$^+$ 295.0222, found 295.0212.

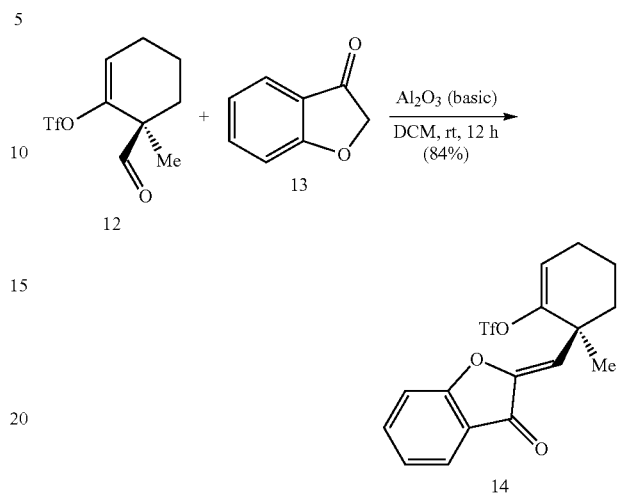

Enone 14: To a solution of 12 (1.36 g, 5.00 mmol) and 13 (738 mg, 5.50 mmol) in DCM (10 mL) was added activated basic alumina (10 g, 98 mmol). The mixture was stirred at ambient temperature overnight, and then filtered through a plug of silica gel to give pure 14 as an orange viscous oil (1.63 g, 84% yield): R$_f$=0.3 (hexanes/ethyl acetate 8:1); $^1$H-NMR (500 MHz, CDCl$_3$) δ 7.76 (br d, J=7.6 Hz, 1H), 7.68-7.57 (m, 1H), 7.21 (br d, J=8.4 Hz, 1H), 7.19 (t, J=7.8 Hz, 1H), 6.03 (s, 1H), 5.88 (t, J=4.1 Hz, 1H), 2.31-2.24 (m, 2H), 2.19 (ddd, J=13.4, 7.0, 3.2 Hz, 1H), 1.85 (ddd, J=13.4, 10.2, 3.3 Hz, 1H), 1.75-1.64 (m, 2H), 1.55 (s, 3H) ppm; $^{13}$C-NMR (126 MHz, CDCl$_3$) δ 184.5, 166.4, 151.9, 147.6, 137.3, 124.7, 123.3, 121.2, 118.4 (q, J=319.5 Hz), 118.1, 117.6, 112.9, 39.8, 37.9, 24.6, 24.5, 18.6 ppm; IR (neat) v 2942, 2874, 1717, 1668, 1606, 1477, 1413, 1210, 1141, 879, 759, 603 cm$^{-1}$; HRMS (ESI-TOF) m/z calcd for C$_{17}$H$_{15}$F$_3$NaO$_5$S$^+$ [M+Na]$^+$ 411.0484, found 411.0484.

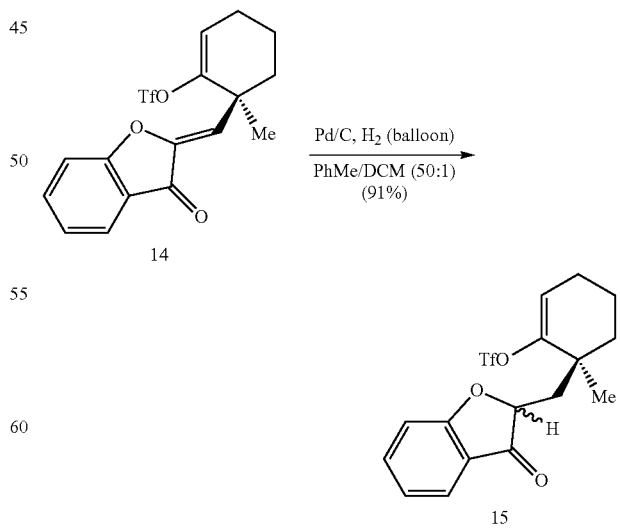

Ketone 15: To a mixture of 14 (422 mg, 1.09 mmol) and 5% Pd/C (40 mg) under H$_2$ atmosphere was charged with dry toluene (10 mL) and DCM (0.2 mL). The reaction mixture was stirred at ambient temperature for 2 hours, then filtered and concentrated in vacuo. Purification by flash chromatography (silica gel, hexanes/ethyl acetate=20:1) gave 15 as a yellow oil and an inseparable but inconsequential mixture of diastereomers (384 mg, 91% combined yield, d.r.=1.1:1). The synthesized 15 was always contaminated by a small amount of unknown impurities (purity ca. >95%). It should be noted that 15 is quite unstable in air, for which it was used in the next step of reaction right after isolation. $R_f$=0.3 (hexanes/ethyl acetate 8:1); $^1$H-NMR (500 MHz, CDCl$_3$) major: δ 7.66 (d, J=7.7 Hz, 1H), 7.62 (t, J=7.8 Hz, 1H), 7.15-7.04 (m, 2H), 5.81 (t, J=4.2 Hz, 1H), 4.55 (dd, J=10.3, 1.7 Hz, 1H), 2.28-2.19 (m, 2H), 2.14 (dd, J=15.1, 1.7 Hz, 1H), 2.07-1.99 (m, 1H), 1.76 (dd, J=15.3, 10.3 Hz, 1H), 1.79-1.64 (m, 3H), 1.32 (s, 3H) ppm; minor: δ 7.66 (d, J=7.7 Hz, 1H), 7.62 (t, J=7.8 Hz, 1H), 7.15-7.04 (m, 2H), 5.82 (t, J=4.3 Hz, 1H), 4.62 (dd, J=10.8, 1.9 Hz, 1H), 2.28-2.19 (m, 2H), 2.14 (dd, J=15.1, 1.9 Hz, 1H), 2.07-1.99 (m, 1H), 1.83 (dd, J=15.1, 10.8 Hz, 1H), 1.79-1.64 (m, 3H), 1.31 (s, 3H) ppm; $^{13}$C-NMR (126 MHz, CDCl$_3$) mixture: δ 201.7, 201.5, 172.6, 172.5, 154.1, 153.8, 138.1, 138.0, 124.4, 124.3, 122.2, 121.99, 121.97, 120.34, 120.25, 118.3 (q, J=319.4 Hz), 117.8, 117.1, 113.64, 113.58, 82.62, 82.58, 40.3, 40.2, 37.9, 37.6, 36.0, 35.7, 24.9, 24.73, 24.68, 18.2, 18.1 ppm; IR (neat) ν 2942, 1723, 1615, 1478, 1464, 1412, 1247, 1212, 1142, 1024, 874, 761, 606 cm$^{-1}$; HRMS (ESI-TOF) m/z calcd for $C_{17}H_{17}F_3NaO_5S^+$ [M+Na]$^+$ 413.0641, found 413.0640.

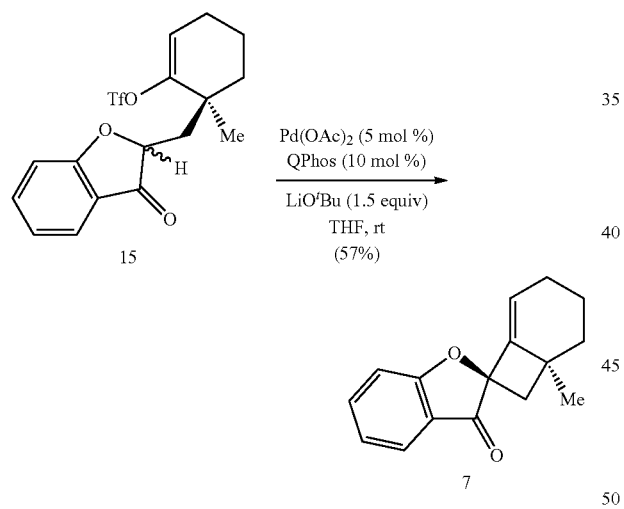

Ketone 7: In the glovebox, to a mixture of 15 (388 mg, 0.99 mmol) and LiO$^t$Bu (119 mg, 1.49 mmol) in a vial (25 mL) was added a solution of Pd(OAc)$_2$ (11.2 mg, 0.050 mmol) and QPhos (71.1 mg, 0.10 mmol) in THF (20 mL). The reaction mixture was divided and placed in 3 vials (ca. 6.7 mL for each vial). It was stirred at ambient temperature for 60 hours, then filtered through a plug of silica gel and concentrated in vacuo. Purification by flash chromatography (silica gel, hexanes/ethyl acetate=20:1) gave 7 as a yellow oil and a single diastereomer (137 mg, 57% yield). It should be noted that in practice, this reaction is very sensitive to reaction scales. $R_f$=0.6 (hexanes/ethyl acetate 4:1); $^1$H-NMR (500 MHz, CDCl$_3$) δ 7.66 (br d, J=7.6 Hz, 1H), 7.61-7.55 (m, 1H), 7.09-7.05 (m, 2H), 5.63 (dd, J=4.3, 2.8 Hz, 1H), 2.56 (d, J=11.4 Hz, 1H), 2.37 (d, J=11.4 Hz, 1H), 2.24-2.03 (m, 2H), 1.80-1.75 (m, 3H), 1.59 (s, 3H), 1.42-1.33 (m, 1H) ppm; $^{13}$C-NMR (126 MHz, CDCl$_3$) δ 199.0, 170.8, 142.6, 137.7, 124.8, 121.8, 120.6, 119.4, 112.8, 93.1, 46.5, 38.8, 36.5, 24.5, 21.6, 19.0 ppm; IR (neat) ν 2931, 2869, 1720, 1610, 1463, 1301, 895, 756 cm$^{-1}$; HRMS (ESI-TOF) m/z calcd for $C_{16}H_{17}O_2^+$ [M+H]$^+$ 241.1223, found 241.1211.

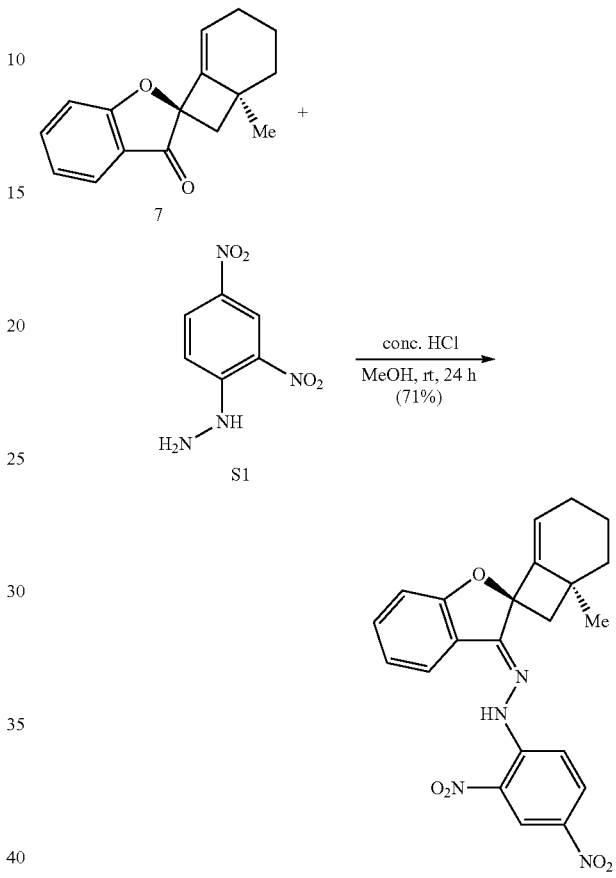

DNP hydrazone of 7 (16): To a mixture of 7 (24 mg, 0.1 mmol) and S1 (21 mg, 0.11 mmol) in MeOH (4 mL) was added concentrated hydrochloric acid (ca. 2 μL). The reaction mixture was stirred at ambient temperature for 24 hours. The solvent was removed under reduced pressure and the residue was purified by flash chromatography (silica gel, hexanes/ethyl acetate=25:1) to give 16 as an orange solid (30 mg, 71% yield): $R_f$=0.55 (hexanes/ethyl acetate 4:1); $^1$H-NMR (500 MHz, CDCl$_3$) δ 11.82 (s, 1H), 9.19 (d, J=2.5 Hz, 1H), 8.40 (dd, J=9.5, 2.4 Hz, 1H), 8.10 (br d, J=7.8 Hz, 1H), 8.08 (d, J=9.6 Hz, 1H), 7.51 (br t, J=7.6 Hz, 1H), 7.15 (t, J=7.6 Hz, 1H), 7.06 (br d, J=8.2 Hz, 1H), 5.75 (dd, J=4.3, 2.7 Hz, 1H), 2.69 (d, J=11.8 Hz, 1H), 2.56 (d, J=11.9 Hz, 1H), 2.28-2.12 (m, 2H), 1.86-1.77 (m, 3H), 1.68 (s, 3H), 1.43 (td, J=13.0, 6.0 Hz, 1H) ppm; $^{13}$C-NMR (126 MHz, CDCl$_3$) δ 164.6, 156.7, 145.27, 145.26, 138.3, 134.8, 130.2, 129.6, 124.7, 123.5, 121.9, 121.1, 117.2, 116.5, 112.1, 93.2, 49.9, 38.7, 36.7, 24.5, 22.9, 19.0 ppm; IR (neat) ν 3338, 2925, 2851, 1617, 1590, 1501, 1465, 1336, 1318, 1085, 741 cm$^{-1}$; HRMS (ESI-TOF) m/z calcd for $C_{22}H_{21}N_4O_5^+$ [M+H]$^+$421.1506, found 421.1509.

53

Example 3

Optimization of the Reduction of Enone 14

A variety of reaction conditions were investigated for use in the selective reduction of the trisubstituted enone olefin in 14. See Table 3, below. Due to the presence of the vinyl triflate moiety in 14, this transformation proved to be somewhat challenging. At least Under the conditions used, copper or manganese-hydride-mediated conjugate reduction methods (see Lipshutz et al., Synlett 1989, 64; Moser et al., J. Am. Chem. Soc. 2010, 132, 7852; Magnus et al., Tett. Lett. 2000, 41, 9731; and Iwasaki et al., J. Am. Chem. Soc. 2014, 136, 1300) gave no reaction or provided no desired product. Without being bound to any one theory, these results are likely due to the α-oxygen substitution reducing the electrophilicity of the enone C=C bond. Results using homogeneous palladium-catalyzed reduction (see Keinan and Greenspoon, J. Am. Chem. Soc. 1986, 108, 7314) were also poor. Again without being bound to any one theory, this result is believed to be due to the competing reactivity of the vinyl triflate towards oxidative addition with a Pd(O) species. However, Pd/C catalyzed hydrogenation was found to chemoselectively reduce the enone olefin to compound 15. Under the optimal solvent conditions (PhMe/DCM (50:1)), compound 15 was obtained in 91% yield.

TABLE 3

Optimization of the Reduction of Enone 14[a]

| Entry | Reducing Agent Combinations | Solvent | Time (h) | Results |
|---|---|---|---|---|
| 1[b] | Cu(OAc)$_2$, P(iPrO)$_3$, Me(EtO)$_2$SiH | PhMe | 12 | N.R. |
| 2[c] | (Ph$_3$PCuH)$_6$ | PhMe | 24 | N.R. |
| 3[c] | Mn(dpm)$_3$, Me(EtO)$_2$SiH | iPrOH/DCM (1:8) | 12 | N.D. |
| 4 | Pd(OAc)$_2$, PPh$_3$, Ph$_2$SiH$_2$ | THF | 2 | 12% |
| 5 | Rh(PPh$_3$)$_3$Cl, H$_2$ | PhMe | 12 | N.R. |
| 6 | PtO$_2$, H$_2$ | EA | 5 | N.D. |
| 7 | Pd/C, H$_2$ | MeOH | 1 | 5% |
| 8 | Pd/C, H$_2$ | EA | 14 | 30-46%[d] |
| 9 | Pd/C, H$_2$ | EA/DCM (50:1) | 2 | 60%[d] |
| 10 | Pd/C, H$_2$ | Et$_2$O/DCM (50:1) | 2 | 53% |
| 11 | Pd/C, H$_2$ | THF/DCM (50:1) | 2 | 24% |
| 12 | Pd/C, H$_2$ | PhMe/DCM (50:1) | 2 | 96% (91%) |

[a]Unless otherwise noted, the yields were determined by NMR using 1,3,5-trimethoxybenzene as the internal standard. Isolated yield was given in parenthesis. 5% Pd/C was used according to the mass of starting material (ca. 10 wt %).
N.R. = no reaction.
N.D. = no desired product.
Mn(dpm)$_3$ = Tris(dipivaloylmethanato)manganese.
[b]Results remained the same regardless of equivalents of copper, phosphite, and silane.
[c]Stoichiometric amount of copper or manganese were used.
[d]Isolated yields.

54

Example 4

Preparation of Compound 8

Compound 8 was prepared as described hereinabove in Schemes 4 and 5. More particular details of the synthesis of compound 8 and its synthetic intermediates are as follows:

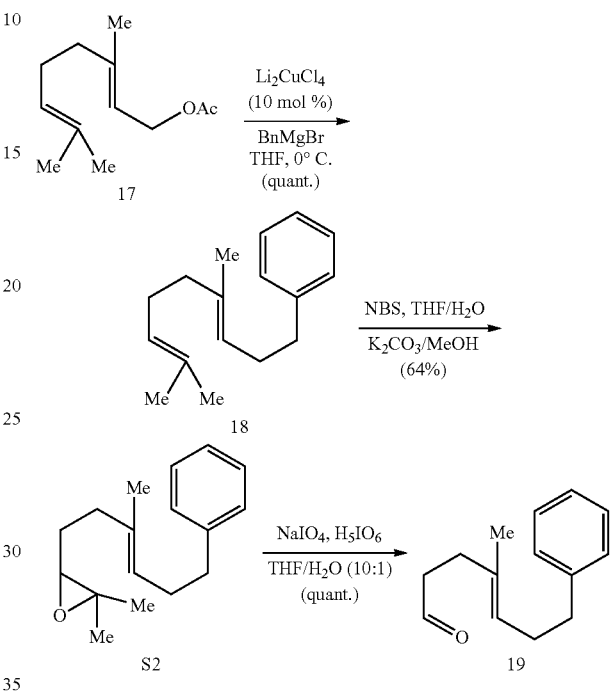

Aldehyde 19: To a solution of 17 (1.96 g, 10.0 mmol) in THF (20 mL) at 0° C. was added a solution of Li$_2$CuCl$_4$ (CuCl$_2$: 134 mg, 1.0 mmol; LiCl: 85 mg, 2.0 mmol) in THF (10 mL). The resulting red solution was stirred at 0° C. while benzyl magnesium bromide solution (1 M in Et$_2$O, 20 mL, 20 mmol) was added dropwise, after which the reaction mixture was quenched with saturated NH$_4$Cl solution and extracted with ether (30 mL×3). The combined extracts were dried over Na$_2$SO$_4$, filtered and concentrated in vacuo to give 18 as a colorless oil (ca. 2.28 g based on NMR analysis, quantitative yield, contaminated by bibenzyl). The experimental NMR data of 18 recorded were consistent with those reported by Loh and co-workers.

To a cooled solution of 18 (2.28 g, 10 mmol) in THF/H$_2$O (2:1 v/v, 300 mL) at 0° C. was slowly added a solution of NBS (1.96 g, 11.0 mmol) in THF/H$_2$O (2:1 v/v, 30 mL) dropwise over a period of 60 minutes. The reaction mixture was stirred at 0° C. until TLC indicated full consumption of 18, after which saturated Na$_2$S$_2$O$_3$ solution (10 mL) was added, followed by addition of MeOH (50 mL) and K$_2$CO$_3$ (6.91 g, 50 mmol). The reaction mixture was allowed to warm up to ambient temperature and stir for another 3 hours. The majority of organic solvents was evaporated under reduced pressure and the aqueous media was extracted with ether (100 mL×3). The combined extracts were dried over Na$_2$SO$_4$, filtered and concentrated in vacuo. Purification by flash chromatography (silica gel, hexanes/ethyl acetate=25:1) gave S2 as a light yellow oil (1.57 g, 64% yield). The experimental NMR data of S2 recorded were consistent with those reported by Loh and co-workers. See Zhao et al., Chem. Commun. 2008, 1353.

To a solution of S2 (1.57 g, 6.4 mmol) in THF/H$_2$O (10:1 v/v, 20 mL) at 0° C. was sequentially added NaIO$_4$ (834 mg, 3.9 mmol) and H$_5$IO$_6$ (1.62 g, 7.1 mmol). The reaction mixture was allowed to warm up to ambient temperature and stir for another 60 minutes, after which it was quenched with saturated NaHCO$_3$ solution and extracted with ethyl acetate (20 mL×3). The combined extracts were dried over Na$_2$SO$_4$, filtered and concentrated in vacuo. Purification by flash chromatography (silica gel, hexanes/ethyl acetate=20:1) gave 19 as a light yellow oil (1.27 g, quantitative yield). The experimental NMR data of 19 recorded were consistent with those reported by Loh and co-workers. See Zhao et al., Chem. Commun. 2008, 1353.

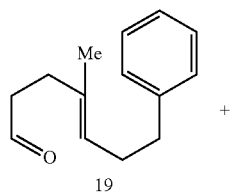

19

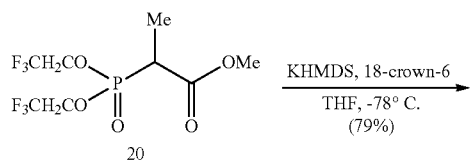

20

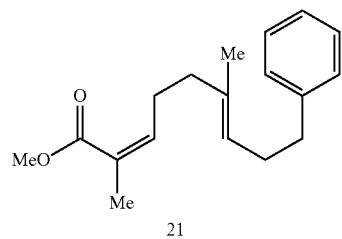

21

Ester 21: To a solution of 20 (2.19 g, 6.6 mmol) and 18-crown-6 (8.3 g, 31.4 mmol) in THF (30 mL) at −78° C. was added a solution of KHMDS (1.32 g, 6.6 mmol) in THF (10 mL) dropwise. The reaction mixture was stirred for 10 minutes, after which a solution of 19 (1.27 g, 6.3 mmol) in THF (10 mL) was added dropwise. The reaction mixture was stirred at the same temperature for another 20 minutes, then quenched with saturated NH$_4$Cl solution and extracted with ether (30 mL×3). The combined extracts were dried over Na$_2$SO$_4$, filtered and concentrated in vacuo. Purification by flash chromatography (silica gel, hexanes/ethyl acetate=20:1) gave 21 as a colorless oil (1.36 g, 79% yield, Z/E>19:1): R$_f$=0.7 (hexanes/ethyl acetate 4:1); $^1$H-NMR (500 MHz, CDCl$_3$) δ 7.30-7.25 (m, 2H), 7.21-7.15 (m, 3H), 5.94-5.87 (m, 1H), 5.20 (br t, J=6.8 Hz, 1H), 3.74 (s, 3H), 2.67-2.60 (m, 2H), 2.59-2.52 (m, 2H), 2.31 (q, J=7.5 Hz, 2H), 2.07 (t, J=7.5 Hz, 2H), 1.90-1.86 (m, 3H), 1.55 (s, 3H) ppm; $^{13}$C-NMR (126 MHz, CDCl$_3$) δ 168.5, 143.1, 142.3, 135.0, 128.4, 128.2, 126.8, 125.7, 124.3, 51.2, 39.1, 36.1, 29.9, 28.0, 20.6, 15.8 ppm; IR (neat) v 3026, 2926, 2856, 1718, 1453, 1435, 1243, 1197, 1128, 748, 699 cm$^{-1}$; HRMS (ESI-TOF) m/z calcd for C$_{18}$H$_{25}$O$_2^+$ [M+H]$^+$ 273.1849, found 273.1851.

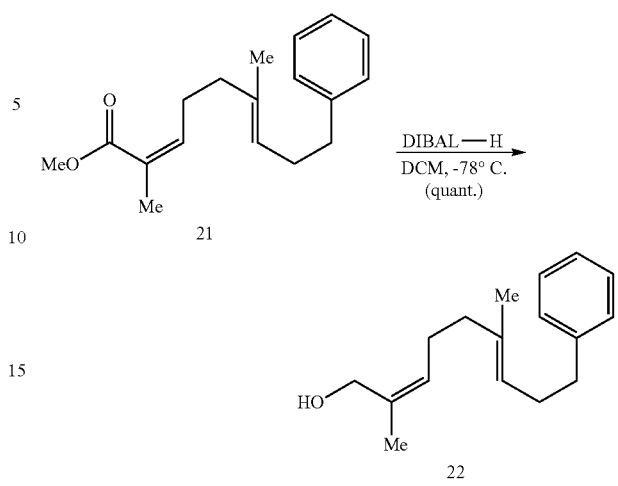

Alcohol 22: To a solution of 21 (1.04 g, 3.84 mmol) in DCM (10 mL) at −78° C. was added DIBAL-H (1.0 M solution in hexane, 8.4 mL, 8.4 mmol) dropwise. Upon finishing addition, the reaction mixture was slowly warmed up to ambient temperature and stirred for another 10 minutes, then quenched with saturated Rochelle salt solution and extracted with DCM (10 mL×3). The combined extracts were dried over Na$_2$SO$_4$, filtered and concentrated in vacuo. Purification by flash chromatography (silica gel, hexanes/DCM/ethyl acetate=5:1:1) gave 22 as a colorless oil (935 mg, quantitative yield): R$_f$=0.7 (hexanes/ethyl acetate 2:1); $^1$H-NMR (500 MHz, CDCl$_3$) δ 7.32-7.26 (m, 2H), 7.22-7.17 (m, 3H), 5.30-5.24 (m, 1H), 5.22-5.15 (m, 1H), 4.12 (s, 2H), 2.67-2.62 (m, 2H), 2.32 (q, J=7.4 Hz, 2H), 2.14 (q, J=7.4 Hz, 2H), 2.01 (t, J=7.6 Hz, 2H), 1.82-1.78 (m, 3H), 1.56 (s, 3H), 1.29 (br s, 1H) ppm; $^{13}$C-NMR (126 MHz, CDCl$_3$) δ 142.3, 135.2, 134.4, 128.4, 128.18, 128.15, 125.7, 124.1, 61.6, 39.8, 36.1, 29.8, 26.1, 21.2, 16.0 ppm; IR (neat) v 3328, 3026, 2922, 2855, 1496, 1453, 1379, 1004, 748, 699 cm$^{-1}$; HRMS (ESI-TOF) m/z calcd for C$_{17}$H$_{25}$O$^+$ [M+H]$^+$ 245.1900, found 245.1900.

Alcohol S4: To a stirred solution of 22 (92 mg, 0.38 mmol) in DCM (2 mL) at 0° C. was added VO(acac)$_2$ (5 mg, 0.02 mmol), followed by addition of TBHP solution (~5.5 M in decane, 0.1 mL, ~0.55 mmol) dropwise. The reaction mixture was stirred at 0° C. until TLC (hexanes/ethyl acetate=2:1) indicated complete consumption of 22. It was then quenched with saturated Na₂S₂O₃ solution and saturated NaHCO₃ solution and extracted with DCM (5 mL×3). The combined extracts were dried over Na₂SO₄, filtered and concentrated in vacuo. Purification by flash chromatography (silica gel, hexanes/DCM/ethyl acetate=4:1:1→2:1:1) gave S3 as a colorless oil (78 mg, 79% yield): $R_f$=0.2 (hexanes/ethyl acetate 4:1); ¹H-NMR (500 MHz, CDCl₃) δ 7.30-7.24 (m, 2H), 7.21-7.14 (m, 3H), 5.23 (t, J=7.0 Hz, 1H), 3.73-3.60 (m, 2H), 2.82 (t, J=6.3 Hz, 1H), 2.65 (t, J=7.8 Hz, 2H), 2.32 (q, J=7.4 Hz, 2H), 2.17 (dt, J=14.6, 7.4 Hz, 1H), 2.09 (dt, J=14.4, 7.7 Hz, 1H), 1.75-1.62 (m, 3H), 1.57 (s, 3H), 1.37 (s, 3H) ppm; ¹³C-NMR (126 MHz, CDCl₃) δ 142.1, 134.6, 128.4, 128.2, 125.7, 124.6, 64.5, 64.0, 60.8, 36.4, 36.0, 29.9, 26.7, 20.2, 15.9 ppm; IR (neat) v 3432, 2968, 2926, 2856, 1452, 1031, 749, 699 cm⁻¹; HRMS (ESI-TOF) m/z calcd for $C_{17}H_{24}NaO_2^+$ [M+Na]⁺ 283.1669, found 283.1669.

Aldehyde 23: To a stirred solution of S3 (664 mg, 2.55 mmol) in DCM (10 mL) at 0° C. was added DMSO (2 mL) and Et₃N (2.1 mL, 15.3 mmol), followed by addition of SO₃·py (1.22 g, 7.65 mmol) in one portion. The reaction mixture was stirred at 0° C. and naturally warmed up to ambient temperature until TLC (hexanes/ethyl acetate=4:1) indicated complete consumption of S3. It was then quenched with saturated NH₄Cl solution and extracted with DCM (10 mL×3). The combined extracts were dried over Na₂SO₄, filtered and concentrated in vacuo. Purification by flash chromatography (silica gel, hexanes/ethyl acetate=20:1) gave 23 as a colorless oil (578 mg, 88% yield): $R_f$=0.7 (hexanes/ethyl acetate 4:1); ¹H-NMR (500 MHz, CDCl₃) δ 9.37 (s, 1H), 7.31-7.24 (m, 2H), 7.20-7.15 (m, 3H), 5.25-5.19 (m, 1H), 3.03 (t, J=6.5 Hz, 1H), 2.64 (t, J=7.8 Hz, 2H), 2.31 (q, J=7.5 Hz, 2H), 2.20 (dt, J=14.4, 7.4 Hz, 1H), 2.10 (dt, J=14.3, 7.6 Hz, 1H), 1.93-1.69 (m, 2H), 1.54 (s, 3H), 1.40 (s, 3H) ppm; ¹³C-NMR (126 MHz, CDCl₃) δ 200.5, 142.1, 133.7, 128.4, 128.2, 125.8, 125.2, 65.3, 62.7, 36.3, 35.8, 29.8, 26.4, 15.9, 15.8 ppm; IR (neat) v 3026, 2973, 2931, 2855, 1723, 1496, 1453, 1383, 750, 700 cm⁻¹; HRMS (ESI-TOF) m/z calcd for $C_{17}H_{23}O_2^+$ [M+H]⁺ 259.1693, found 259.1690.

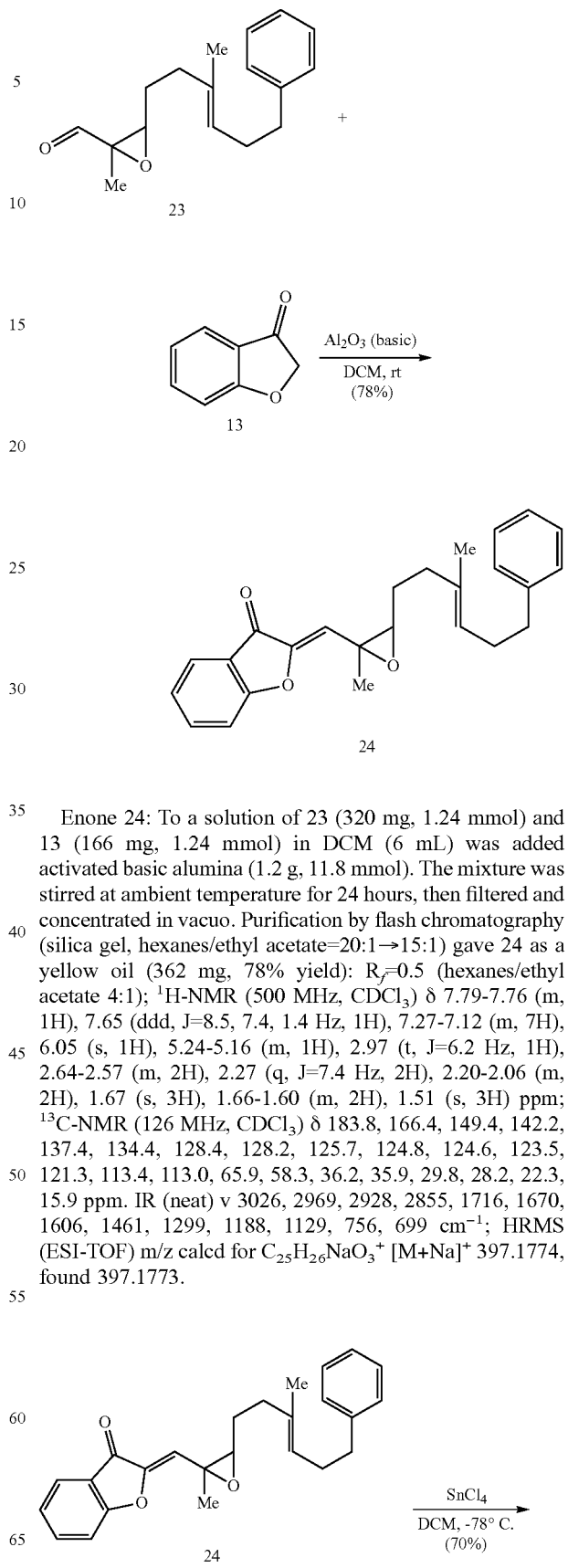

Enone 24: To a solution of 23 (320 mg, 1.24 mmol) and 13 (166 mg, 1.24 mmol) in DCM (6 mL) was added activated basic alumina (1.2 g, 11.8 mmol). The mixture was stirred at ambient temperature for 24 hours, then filtered and concentrated in vacuo. Purification by flash chromatography (silica gel, hexanes/ethyl acetate=20:1→15:1) gave 24 as a yellow oil (362 mg, 78% yield): $R_f$=0.5 (hexanes/ethyl acetate 4:1); ¹H-NMR (500 MHz, CDCl₃) δ 7.79-7.76 (m, 1H), 7.65 (ddd, J=8.5, 7.4, 1.4 Hz, 1H), 7.27-7.12 (m, 7H), 6.05 (s, 1H), 5.24-5.16 (m, 1H), 2.97 (t, J=6.2 Hz, 1H), 2.64-2.57 (m, 2H), 2.27 (q, J=7.4 Hz, 2H), 2.20-2.06 (m, 2H), 1.67 (s, 3H), 1.66-1.60 (m, 2H), 1.51 (s, 3H) ppm; ¹³C-NMR (126 MHz, CDCl₃) δ 183.8, 166.4, 149.4, 142.2, 137.4, 134.4, 128.4, 128.2, 125.7, 124.8, 124.6, 123.5, 121.3, 113.4, 113.0, 65.9, 58.3, 36.2, 35.9, 29.8, 28.2, 22.3, 15.9 ppm. IR (neat) v 3026, 2969, 2928, 2855, 1716, 1670, 1606, 1461, 1299, 1188, 1129, 756, 699 cm⁻¹; HRMS (ESI-TOF) m/z calcd for $C_{25}H_{26}NaO_3^+$ [M+Na]⁺ 397.1774, found 397.1773.

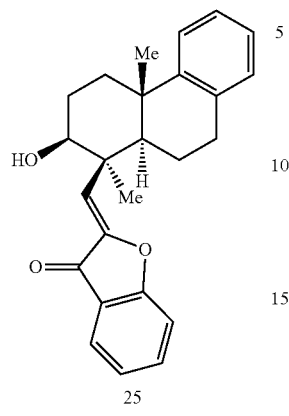

25

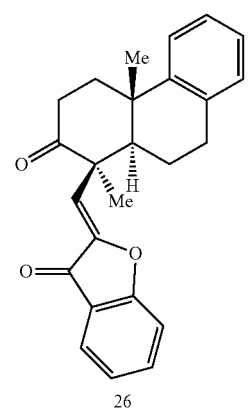

26

Enone 25: To a solution of 24 (604 mg, 1.61 mmol) in DCM (10 mL) at −78° C. was added SnCl₄ (1.0 M in heptane, 1.6 mL, 1.6 mmol) dropwise. The mixture was stirred at −78° C. for 15 minutes, then quenched with saturated NaHCO₃ solution, and extracted with DCM (10 mL×3). The combined extracts were dried over Na₂SO₄, filtered and concentrated in vacuo. Flash chromatography (silica gel, hexanes/DCM/ethyl acetate=4:1:1) gave 25 as a pale yellow solid (425 mg, 70% yield): $R_f$=0.1 (hexanes/ethyl acetate 4:1); MP=224-225° C.; ¹H-NMR (500 MHz, CDCl₃) δ 7.79 (br d, J=7.6 Hz, 1H), 7.64 (br t, J=7.8 Hz, 1H), 7.29-7.22 (m, 2H), 7.20 (br t, J=7.4 Hz, 1H), 7.13 (br t, J=7.4 Hz, 1H), 7.09 (br t, J=7.2 Hz, 1H), 7.05 (br d, J=7.4 Hz, 1H), 6.37 (s, 1H), 3.44 (dd, J=11.8, 4.3 Hz, 1H), 3.00-2.87 (m, 2H), 2.39 (br d, J=13.3 Hz, 1H), 2.31 (dd, J=13.0, 6.6 Hz, 1H), 2.19 (br s, 1H), 2.15-1.98 (m, 2H), 1.82-1.59 (m, 3H), 1.62 (s, 3H), 1.14 (s, 3H) ppm; ¹³C-NMR (126 MHz, CDCl₃) δ 183.7, 165.9, 148.3, 147.9, 136.9, 134.7, 129.0, 125.9, 125.6, 124.9, 124.6, 123.3, 121.6, 118.3, 112.9, 79.1, 53.1, 45.6, 37.7, 37.0, 30.5, 28.2, 25.2, 24.2, 19.8 ppm; IR (neat) v 3449, 2935, 2872, 1706, 1655, 1601, 1477, 1460, 1300, 1192, 1174, 1100, 757, 728 cm⁻¹; HRMS (ESI-TOF) m/z calcd for $C_{25}H_{26}NaO_3^+$ [M+Na]⁺ 397.1774, found 397.1781.

Enone 26: Alcohol 25 (37.4 mg, 0.10 mmol) was dissolved in DCM (1 mL), followed by sequential addition of NaHCO₃ (84 mg, 1.0 mmol) and Dess-Martin periodinane (46.7 mg, 0.11 mmol) at ambient temperature. After 15 minutes, the reaction mixture was quenched by addition of saturated Na₂S₂O₃ solution, and extracted with DCM (10 mL×3). The combined extracts were dried over Na₂SO₄, filtered and concentrated in vacuo. Purification by flash chromatography (silica gel, hexanes/ethyl acetate=10:1) gave 26 as a white solid (23 mg, 62% yield): $R_f$=0.3 (hexanes/ethyl acetate 4:1); MP=215-217° C.; ¹H-NMR (500 MHz, CDCl₃) δ 7.77-7.73 (m, 1H), 7.63 (ddd, J=8.6, 7.4, 1.4 Hz, 1H), 7.26-7.06 (m, 6H), 6.41 (s, 1H), 3.11-2.90 (m, 3H), 2.65-2.52 (m, 2H), 2.15 (ddt, J=18.3, 11.9, 6.2 Hz, 1H), 2.08-2.00 (m, 1H), 1.95-1.87 (m, 2H), 1.44 (s, 3H), 1.42 (s, 3H) ppm; ¹³C-NMR (126 MHz, CDCl₃) δ 211.0, 183.9, 166.3, 146.6, 146.5, 137.3, 134.4, 129.2, 126.14, 126.07, 124.8, 124.7, 123.4, 121.5, 116.5, 113.2, 54.6, 52.5, 39.9, 38.0, 36.6, 30.6, 24.0, 22.0, 20.0 ppm; IR (neat) v 2928, 2863, 1712, 1664, 1602, 1460, 1299, 1189, 758 cm⁻¹; HRMS (ESI-TOF) m/z calcd for $C_{25}H_{25}O_3^+$ [M+H]⁺ 373.1798, found 373.1796.

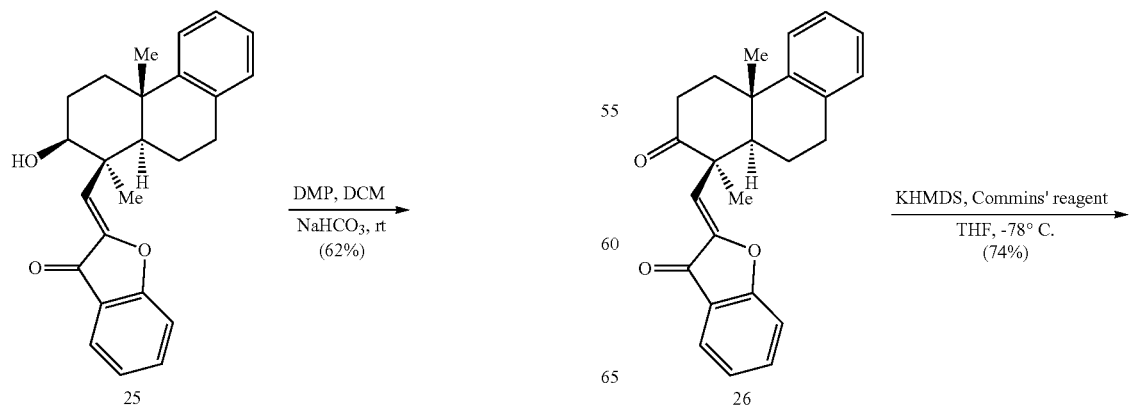

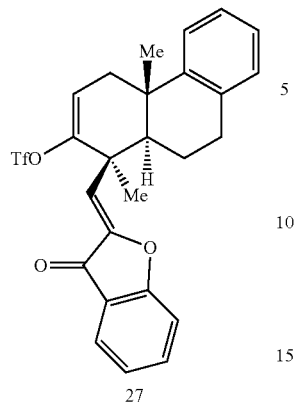

27

Enone 27: To a flame-dried round bottle flask was charged with KHMDS (296 mg, 1.48 mmol) and THF (2 mL). The clear solution was cooled down to −78° C., after which a solution of 26 (460 mg, 1.24 mmol) in THF (20 mL) was added dropwise. The reaction mixture was stirred for 15 minutes, and then solid Comins' reagent (582 mg, 1.48 mmol) was added to the solution in one portion. The reaction mixture was stirred for another 3 hours, quenched with saturated NH$_4$Cl solution and extracted with ethyl acetate (30 mL×3). The combined extracts were dried over Na$_2$SO$_4$, filtered and concentrated in vacuo. Purification by flash chromatography (silica gel, hexanes/ethyl acetate=20:1) gave 27 as a white solid (466 mg, 74% yield): R$_f$=0.5 (hexanes/ethyl acetate 4:1); MP=140-142° C.; $^1$H-NMR (500 MHz, CDCl$_3$) δ 7.76 (br d, J=7.6 Hz, 1H), 7.67-7.63 (m, 1H), 7.29-7.15 (m, 4H), 7.12 (br t, J=6.9 Hz, 1H), 7.06 (br d, J=7.5 Hz, 1H), 6.02 (s, 1H), 5.98 (dd, J=6.5, 2.0 Hz, 1H), 2.99-2.87 (m, 2H), 2.85 (dd, J=17.3, 6.6 Hz, 1H), 2.40 (br d, J=17.1 Hz, 1H), 2.13 (dd, J=13.0, 5.5 Hz, 1H), 2.03 (dd, J=12.6, 1.5 Hz, 1H), 1.77 (dq, J=12.6, 5.9 Hz, 1H), 1.67 (s, 3H), 1.29 (s, 3H) ppm; $^{13}$C-NMR (126 MHz, CDCl$_3$) δ 184.0, 166.4, 151.8, 147.8, 145.2, 137.3, 134.5, 129.0, 126.4, 126.0, 125.8, 124.8, 123.4, 121.2, 118.4 (q, J=319.6 Hz), 114.6, 114.2, 113.0, 52.5, 43.0, 38.5, 36.6, 30.8, 25.3, 24.7, 20.6 ppm; IR (neat) v 2940, 1718, 1668, 1605, 1413, 1299, 1210, 1141, 881, 758, 604 cm$^{-1}$; HRMS (ESI-TOF) m/z calcd for C$_{26}$H$_{23}$F$_3$NaO$_5$S$^+$ [M+Na]$^+$ 527.1111, found 527.1110.

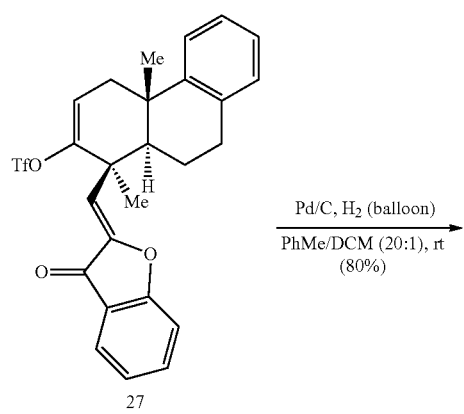

27 → Pd/C, H$_2$ (balloon) / PhMe/DCM (20:1), rt (80%)

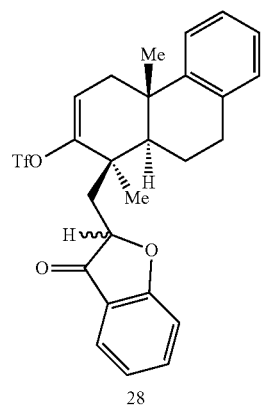

28

Ketone 28: To a mixture of 27 (25 mg, 0.050 mmol) and 5% Pd/C (25 mg) under H$_2$ atmosphere was charged with dry toluene (1 mL) and DCM (0.05 mL). The reaction mixture was stirred at ambient temperature for 12 hours, then filtered through a plug of silica gel, washed with ether and concentrated in vacuo. Purification by flash chromatography (silica gel, hexanes/ethyl acetate=20:1) gave 28 as a white solid and an inseparable but inconsequential mixture of diastereomers (20 mg, 80% combined yield, d.r.=2:1). The synthesized 28 was always contaminated by a small amount of unknown impurities (purity ca. >95%) that did not influence the next step of reaction. In practice, the crude 28 was pure enough to be directly used for the next step without further purification: R$_f$=0.5 (hexanes/ethyl acetate 4:1); $^1$H-NMR (500 MHz, CDCl$_3$) major: δ 7.69-7.60 (m, 2H), 7.25-7.03 (m, 6H), 5.90 (dd, J=4.0, 2.3 Hz, 1H), 4.73 (dd, J=10.6, 1.4 Hz, 1H), 3.03-2.83 (m, 2H), 2.77 (dd, J=17.4, 6.3 Hz, 1H), 2.38 (d, J=17.7 Hz, 1H), 2.16 (dd, J=15.6, 1.3 Hz, 1H), 2.07 (dd, J=15.6, 10.7 Hz, 1H), 2.02 (dd, J=12.7, 5.8 Hz, 1H), 1.94 (d, J=11.1 Hz, 1H), 1.80 (dd, J=12.6, 5.3 Hz, 1H), 1.50 (s, 3H), 1.32 (s, 3H) ppm; minor: δ 7.69-7.60 (m, 2H), 7.25-7.03 (m, 6H), 5.91 (dd, J=4.0, 2.2 Hz, 1H), 4.80 (dd, J=11.2, 1.4 Hz, 1H), 3.03-2.83 (m, 2H), 2.80 (dd, J=17.4, 6.6 Hz, 1H), 2.40 (d, J=16.7 Hz, 1H), 2.55 (d, J=15.5 Hz, 1H), 1.95-1.90 (m, 1H), 1.92 (dd, J=15.4, 1.4 Hz, 1H), 1.83 (dd, J=12.6, 5.2 Hz, 1H), 1.70 (dd, J=15.4, 11.2 Hz, 1H), 1.55 (s, 3H), 1.39 (s, 3H) ppm; $^{13}$C-NMR (126 MHz, CDCl$_3$) major: δ 201.79, 172.63, 153.86, 145.64, 138.16, 134.59, 128.97, 126.38, 125.96, 125.89, 124.28, 121.90, 120.38, 118.42 (q, J=319.8 Hz), 114.32, 113.79, 82.88, 50.98, 39.63, 38.88, 36.66, 35.59, 31.11, 25.78, 24.38, 20.14 ppm; minor: δ 201.43, 172.45, 154.56, 145.77, 138.04, 134.64, 128.95, 126.40, 125.97, 125.94, 124.40, 121.92, 120.36, 118.36 (q, J=319.6 Hz), 115.39, 113.69, 83.80, 51.61, 40.62, 38.88, 36.63, 35.59, 31.22, 26.03, 25.06, 20.38 ppm; IR (neat) v 3060, 2973, 2942, 1718, 1615, 1477, 1464, 1412, 1212, 1142, 999, 908, 760, 734, 605 cm$^{-1}$; HRMS (ESI-TOF) m/z calcd for C$_{26}$H$_{26}$F$_3$O$_5$S$^+$ [M+H]$^+$ 507.1448, found 507.1448.

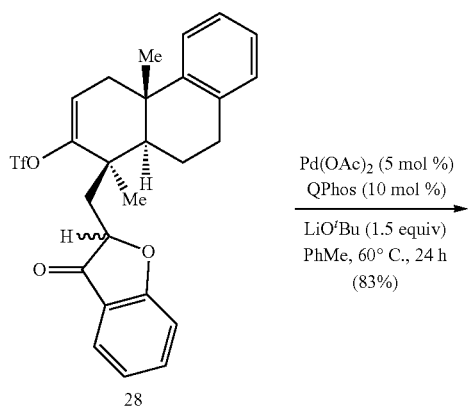

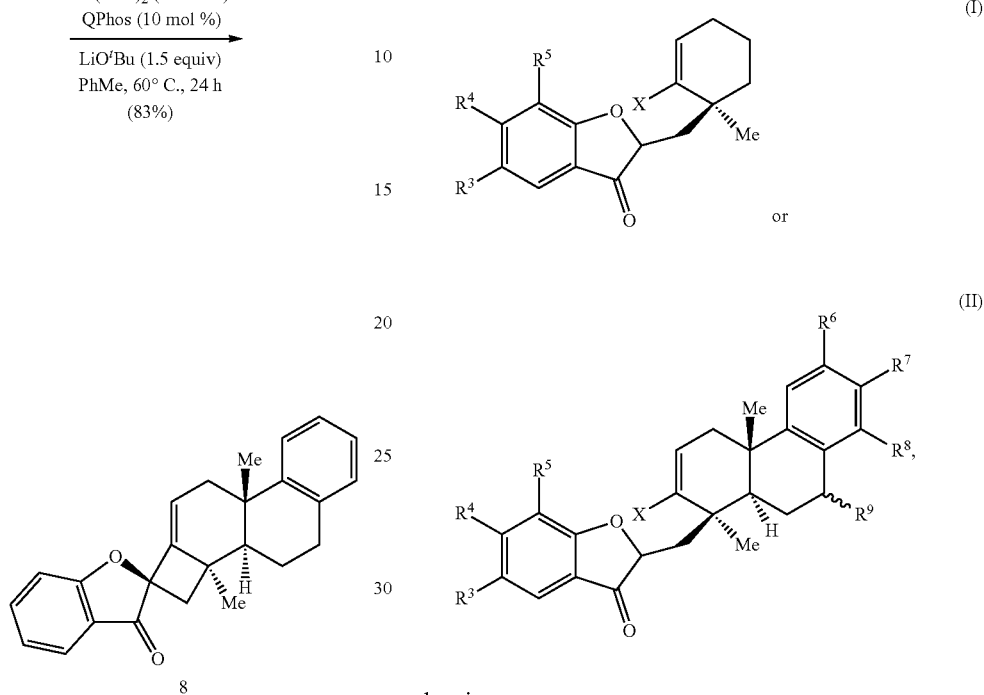

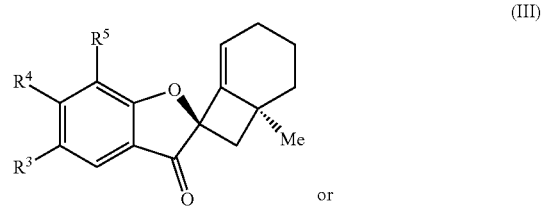

Ketone 8: In the glovebox, 0.1 mL of a 1-mL stock solution of Pd(OAc)$_2$ (5.2 mg, 0.023 mmol) and QPhos (32.6 mg, 0.046 mmol) in dry toluene was added to LiO$^t$Bu (5.4 mg, 0.068 mmol), followed by addition of a solution of 28 (24 mg, 0.047 mmol) in dry toluene (0.8 mL). The reaction mixture was then heated to 60° C. for 24 hours, after which it was cooled down, filtered through a plug of silica gel, washed with ether, and concentrated in vacuo. Purification by flash chromatography (silica gel, hexanes/ethyl acetate=20:1) gave 8 as a white solid (14 mg, 83% yield): R$_f$=0.7 (hexanes/ethyl acetate 4:1); MP=174-177° C.; $^1$H-NMR (500 MHz, CDCl$_3$) δ 7.68 (br d, J=7.3 Hz, 1H), 7.64-7.58 (m, 1H), 7.30-7.25 (m, 1H), 7.17-7.12 (m, 3H), 7.11-7.06 (m, 2H), 5.93 (dd, J=8.6, 4.3 Hz, 1H), 3.11-2.98 (m, 2H), 2.76 (dd, J=14.4, 8.6 Hz, 1H), 2.61 (d, J=11.2 Hz, 1H), 2.31 (d, J=11.2 Hz, 1H), 2.07 (dd, J=14.3, 4.2 Hz, 1H), 1.88-1.80 (m, 3H), 1.72 (s, 3H), 1.19 (s, 3H) ppm; $^{13}$C-NMR (126 MHz, CDCl$_3$) δ 198.9, 170.8, 147.6, 144.6, 137.8, 135.9, 129.4, 125.8, 125.6, 124.8, 123.5, 121.8, 120.8, 120.5, 112.8, 92.6, 49.7, 44.6, 41.8, 40.2, 35.5, 29.5, 25.9, 22.7, 18.7 ppm; IR (neat) v 2930, 2869, 1717, 1612, 1476, 1463, 1300, 1253, 754, 728 cm$^{-1}$; HRMS (ESI-TOF) m/z calcd for C$_{25}$H$_{25}$O$_2$$^+$ [M+H]$^+$ 357.1849, found 357.1855.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of preparing a phainanoid analog, the method comprising:

(a) providing a compound of Formula (I) or Formula (II):

wherein:

X is selected from the group consisting of a halide and —O—S(=O)$_2$—R, wherein R is selected from alkyl, substituted alkyl, aryl, and substituted aryl;

R$^3$, R$^4$, and R$^5$ are each independently selected from the group consisting of H, alkyl, substituted alkyl, aryl, substituted aryl, alkoxy, aryloxy, amino, and acetamido;

R$^6$, R$^7$, and R$^8$ are each independently selected from the group consisting of H, alkyl, substituted alkyl, aryl, substituted aryl, alkoxy, aryloxy, amino, acetamido, and nitro; and R$^9$ is selected from the group consisting of H, hydroxyl, and alkoxy; and (b) contacting the compound of Formula (I) or Formula (II) with a metal compound, a ligand precursor, and a non-nucleophilic base to perform an intramolecular ketone alkenylation reaction; thereby providing the phainanoid analog, wherein the phainanoid analog has a structure of Formula (III) or Formula (IV):

(IV)

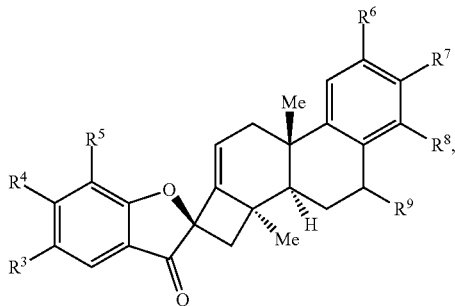

wherein R³—R⁹ are as defined for the compounds of Formulas (I) and (II).

2. The method of claim 1, wherein X is —O—S(=O)₂—CF₃ (—OTf).

3. The method of claim 1, wherein the metal compound is a Pd compound.

4. The method of claim 1, wherein the ligand precursor is a phosphine.

5. The method of claim 1, wherein the base is selected from the group consisting of lithium hexamethyldisilamide (LiHMDS), potassium hexamethyldisilamide (KHMDS), sodium hexamethyldisilamide (NaHMDS), cesium carbonate (Cs₂CO₃), lithium tert-butoxide (LiO^tBu), potassium tert-butoxide (KO^tBu), and sodium tert-butoxide (NaO^tBu).

6. The method of claim 1, wherein the method comprises providing a compound of Formula (I), and wherein the compound of Formula (I) is contacted with a Pd compound, a phosphine, and the non-nucleophilic base in the presence of an ether solvent.

7. The method of claim 1, wherein the method comprises providing a compound of Formula (II), and wherein the compound of Formula (II) is contacted with a Pd compound, a phosphine, and the non-nucleophilic base in the presence of an aromatic solvent.

8. The method of claim 1, wherein the compound of Formula (III) or Formula (IV) is provided in a yield of about 65% or more and/or in a diastereomeric ratio of about 20:1 or greater.

9. A method of preparing a phainanoid analog, the method comprising:

(a) providing a compound of Formula (I) or Formula (II):

(I)

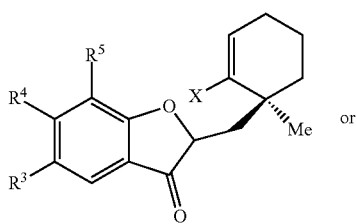

or (II)

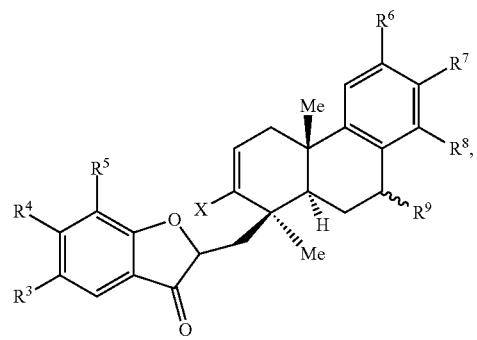

wherein:

X is selected from a halide and —O—S(=O)₂—R, wherein R is selected from alkyl, substituted alkyl, aryl, and substituted aryl; and R³, R⁴, R⁵ R⁶, R⁷, R⁸, and R⁹ are each H; and (b) contacting the compound of Formula (I) or Formula (II) with a metal compound, a ligand precursor, and a non-nucleophilic base to perform an intramolecular ketone alkenylation reaction; thereby providing the phainanoid analog selected from the group consisting of:

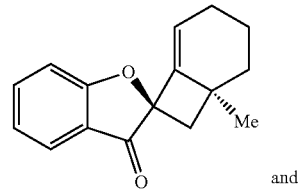

and

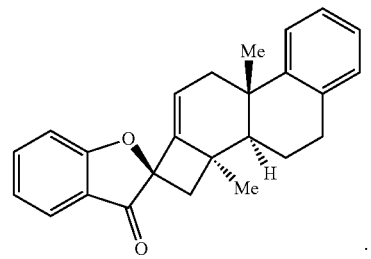

10. A compound of one of Formulas (V) or (VI):

(V)

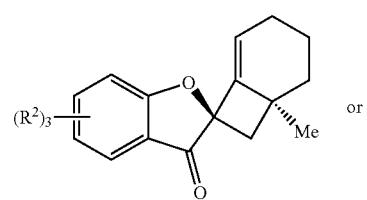

or

-continued (VI)

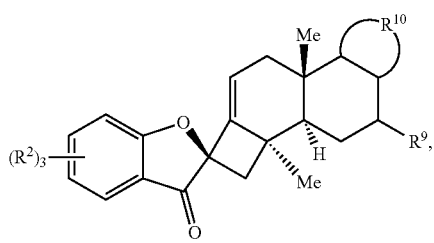

wherein:
- each $R^2$ is independently selected from the group consisting of H, alkyl, substituted alkyl, aryl, substituted aryl, alkoxy, aryloxy, amino, and acetamido;
- $R^9$ is selected from the group consisting of H, =O, hydroxyl, protected hydroxyl, and alkoxy; and
- $R^{10}$ forms a substituted or unsubstituted monocyclic or bicyclic aromatic ring structure selected from the group consisting of benzene, indole, furan, pyrrole and benzofuran.

11. The compound of claim 10, wherein $R^{10}$ forms a substituted or unsubstituted benzene ring structure, and wherein the compound of Formula (VI) is a compound of Formula (VIa):

(VIa)

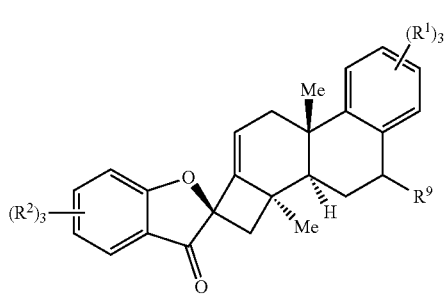

wherein;
- each $R^1$ is independently selected from the group consisting of H, alkyl, substituted alkyl, aryl, substituted aryl, alkoxy, aryloxy, amino, acetamido, and nitro;
- each $R^2$ is independently selected from the group consisting of H, alkyl, substituted alkyl, aryl, substituted aryl, alkoxy, aryloxy, amino, and acetamido; and
- $R^9$ is selected from the group consisting of H, =O, hydroxyl, protected hydroxyl, and alkoxy.

12. The compound of claim 10, wherein the compound of Formula (V) or Formula (VI) is a compound of Formula (III) or Formula (IV):

(III)

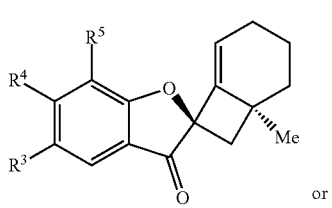

or

-continued (IV)

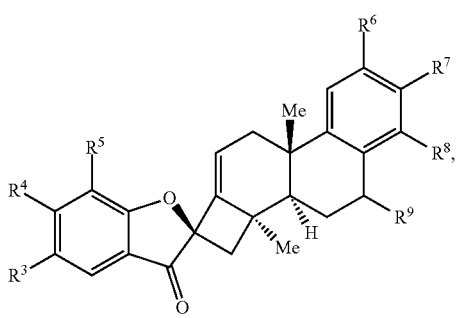

wherein:
- $R^3$, $R^4$, and $R^5$ are each independently selected from the group consisting of H, alkyl, substituted alkyl, aryl, substituted aryl, alkoxy, aryloxy, amino, and acetamido;
- $R^6$, $R^7$, and $R^8$ are each independently selected from the group consisting of H, alkyl, substituted alkyl, aryl, substituted aryl, alkoxy, aryloxy, amino, acetamido, and nitro; and
- $R^9$ is selected from the group consisting of H, =O, hydroxyl, protected hydroxyl, and alkoxy.

13. The compound of claim 12, wherein $R^9$ is =O and the compound of Formula (IV) is a compound of Formula (IVb):

(IVb)

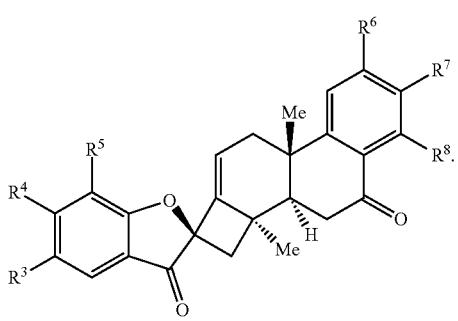

14. The compound of claim 12, wherein $R^9$ is selected from H, hydroxyl, protected hydroxyl, and alkoxy, and the compound of Formula (IV) is a compound of Formula (IVa):

(IVa)

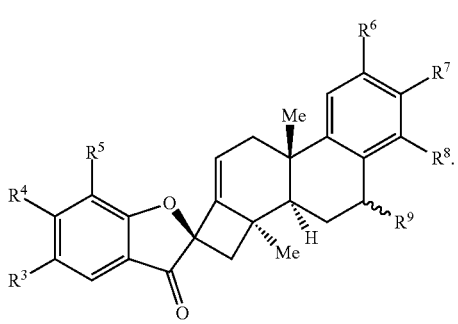

15. A compound selected from the group consisting of:

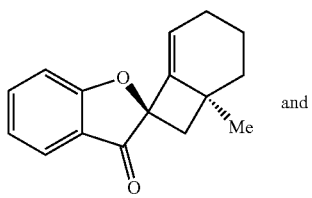
and

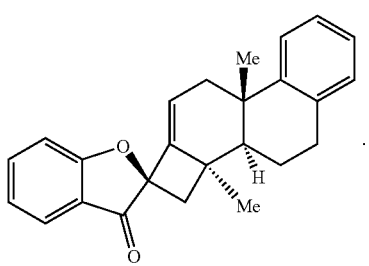

16. A pharmaceutical composition comprising a compound of claim 10.

17. A compound of one of Formulas (I'), (II') or (II"):

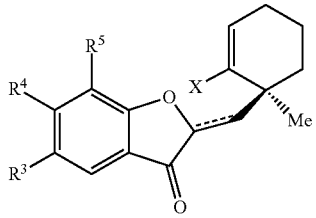
(I')

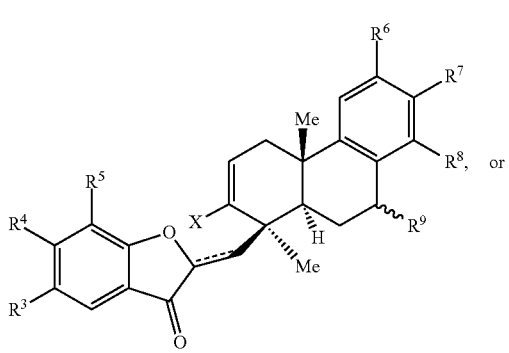
(II')

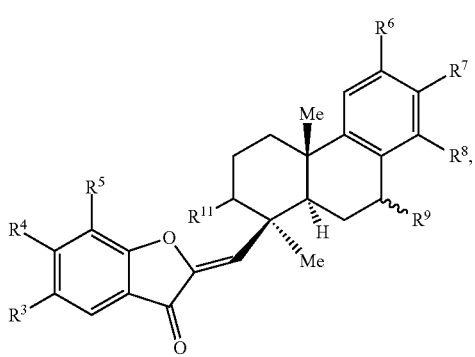
(II")

wherein:

- ≡≡≡ is a double or single bond;
- X is selected from the group consisting of a halide and —O—S(=O)$_2$—R, wherein R is selected from the group consisting of alkyl, substituted alkyl, aryl, and substituted aryl;
- $R^3$, $R^4$, and $R^5$ are each independently selected from the group consisting of H, alkyl, substituted alkyl, aryl, substituted aryl, alkoxy, aryloxy, amino, and acetamido;
- $R^6$, $R^7$, and $R^8$ are each independently selected from the group consisting of H, alkyl, substituted alkyl, aryl, substituted aryl, alkoxy, aryloxy, amino, acetamido, and nitro;
- $R^9$ is selected from the group consisting of H, hydroxyl, and alkoxy; and
- $R^{11}$ is selected from the group consisting of =O, hydroxyl, and protected hydroxyl.

18. The compound of claim 17, wherein X is —O—S(=O)$_2$—CF$_3$ (—OTf).

19. A compound selected from the group consisting of:

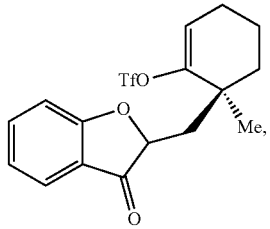

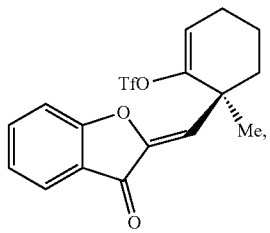

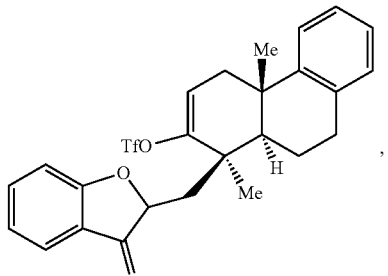

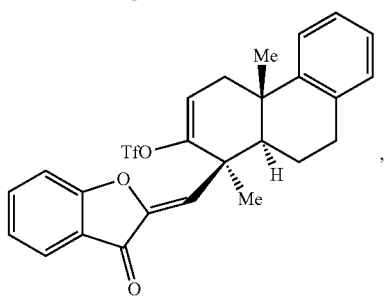

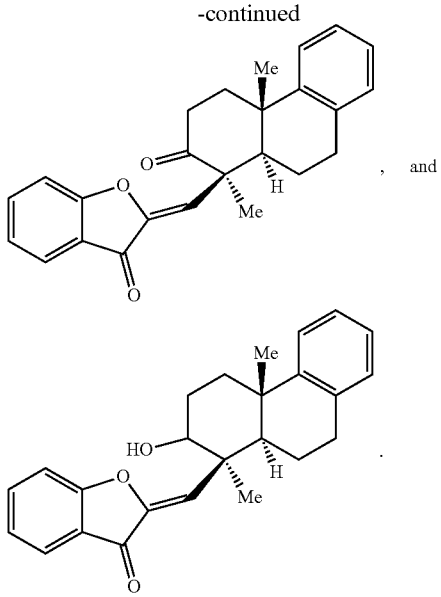

wherein —OTf is —O—S(=O)$_2$—CF$_3$.

20. The method of claim 1, wherein R is —CF$_3$, —CH$_3$, —C$_6$H$_4$CH$_3$, or —C$_n$F$_{2n+1}$, where n is an integer between 2 and 12.

21. The method of claim 20, where n is an integer between 2 and 6.

22. The method of claim 1, wherein the metal compound is a palladium (Pd), nickel (Ni) or platinum (Pt) compound and wherein the ligand precursor is a N-heterocyclic carbene (NHC) precursor or a phosphine.

23. The method of claim 3, wherein the Pd compound is a Pd(II) compound.

24. The method of claim 23, wherein the Pd(II) compound is palladium acetate (Pd(OAc)$_2$).

25. The method of claim 4, wherein the phosphine is a dialkylarylphosphine.

26. The method of claim 25, wherein the dialkylarylphosphine comprises one or both of a ferrocenyl group and a tert-butyl group.

27. The method of claim 6, wherein the ether solvent is tetrahydrofuran (THF).

28. The method of claim 7, wherein the aromatic solvent is toluene.

29. The compound of claim 17, wherein R is —CF$_3$, —CH$_3$, —C$_6$H$_4$CH$_3$, or —C$_n$F$_{2n+1}$, wherein n is an integer between 2 and 12.

30. The compound of claim 29, wherein n is an integer between 2 and 6.

* * * * *